United States Patent [19]
Barbas et al.

[11] Patent Number: 6,110,462
[45] Date of Patent: Aug. 29, 2000

[54] ENZYMATIC DNA MOLECULES THAT CONTAIN MODIFIED NUCLEOTIDES

[75] Inventors: Carlos F. Barbas, Del Mar; Gerald Joyce, Encinitas; Stephen W. Santoro; Sakthivel Kandasamy, both of San Diego, all of Calif.

[73] Assignee: The Scripps Research Institute, La Jolla, Calif.

[21] Appl. No.: 09/262,142

[22] Filed: Mar. 3, 1999

[51] Int. Cl.[7] .............................. C07H 21/04; C12Q 1/68; A61K 38/46; C12N 9/22; C12P 19/34

[52] U.S. Cl. .................... 424/94.6; 435/91.1; 435/91.31; 435/183; 435/196; 435/199; 435/91.53; 424/94.1; 424/94.61; 536/23.1; 536/24.5

[58] Field of Search ................................ 435/91.1, 91.31, 435/91.3; 536/23.1, 24.1; 514/44

[56] References Cited

PUBLICATIONS

Barbas & Sakthivel, Expanding the potential of DNA for binding and catalysis: Delineation of a class of highly functionalized dUTP derivatives that are substrates for thermostable DNA polymerases, Angewandte Chemie, vol. 37. No. 20, pp. 2872–2875, Oct. 1998.

Yu, et al., "Cyanine dye dUTP analogs for enzymatic labeling of DNA probes", *Nucleic Acids Research 22 (15)*: 3226–3232 (1994).

Kovács, et al., "Simple Synthesis of 5–Vinyl– and 5–Ethynyl–2'–Triphosphates", *Tetrahedron Letters 29 (36)*: 4525–4528 (1998).

Langer, et al., "Enzymatic synthesis of biotin–labeled polynucleotides: Novel nucleic acid affinity probes", *Proc. Natl. Acad. Sci. USA 78*: USA 78: 6633–6637 (1981).

Cook, et al., "Synthesis and hybridization of a series of biotinylated oligonucleotides", *Nucleic Acids Research 16 (9)*: 4077–4095 (1988).

Aurup, et al., 2'–Fluoro– and 2'–Amino–2'–deoxynucleoside 5'–Triphosphates as Substrates for T7 RNA Polymerase, *Biochemistry 31 (40)*: 9636–9641 (1992).

Limbach, et al., "Summary: the modified nucleosides of RNA", *Nucleic Acids Research 22 (12)*: 2183–2196 (1994).

Dewey, et al., "The RNA World: Functional Diversity in a Nucleoside by Carboxyamidation of Uridine", *Nucleosides& Nucleotides l5 (10)*: 1611–1617 (1996).

Dewey, et al., "New Uridine Derivatives for Systematic Evolution of RNA Ligands by Exponential Enrichment", *J. Am. Chem. Soc. 117*: 8474–8475 (1995).

Crouch, et al., "Synthesis of 2'–Deoxyuridine Nucleosides with Appended 5–Position Carbonyl Cross–Linking Groups", *Nucleosides & Nucleotides 13 (4)*: 939–944 (1994).

Eaton, et al., "Ribonucleosides and RNA", *Annu. Rev. Biochem. 64*: 837–863 (1995).

Lorsch, et al., "Chance and Necessity in the Selection of Nucleic Acid Catalysts", *Acc. Chem. Res. 29*: 103–110 (1996).

Breaker, "In Vitro Selection of Catalytic Polynucleotides", *Chem. Rev. 97*: 371–390 (1997).

Jäschke, et al., "In Vitro Selected Oligonucleotides as Tools in Organic Chemistry", *Synlett 6*: 825–833 (1999).

Tarasow, et al., "Characteristics of an RNA Diels—Alderase Active Site", *J. Am. Chem. Soc. 121*: 3614–3617 (1999).

Rawls, "Catalytic DNAs", *C&EN* (Feb. 3, 1997) Science/Technology, pp. 33–35.

Eaton, et al., "Let's get specific: the relationship between specificity and affinity", *Chemistry & Biology 2 (10)*: 633–638 (1995).

Williams, et al., "Function of specific 2'–hydroxyl groups of guanosines in a hammerhead ribozyme probed by 2' modifications", *Proc. Natl. Acad. Sci. USA 89*: 918–921 (1992).

Santoro, et al., "Mechanism and Utility of an RNA–Cleaving DNA Enzyme", *Biochemistry 37*: 13330–13342 (1998).

Sakthivel, et al., "Expanding the Potential of DNA for Binding and Catalysis: Highly Functionalized dUTP Derivatives That Are Substrates for Thermostable DNA Polymerase", *Angew. Chem. Int. Ed. 37 (20): 2872–2875* (1998).

Santoro, et al., "A general purpose RNA–cleaving DNA enzyme", *Proc. Natl. Acad. Sci. USA 94*: 4262–4266 (1997).

Breaker, et al., "A DNA enzyme that cleaves RNA", *Chemistry & Biology 1*: 223–229 (1994).

Joyce, "Nucleic acid enzymes: Playing with a fuller deck", *Proc. Natl. Acad. Sci. USA 95*: 5845–5847 (1988).

delCardayrè, et al., "Structural Determinants of Enzymatic Processivity", *Biochemistry 33 (20)*: 6031–6037 (1994).

Pyle, "Ribozymes: A Distinct Class of Metalloenzymes", *Science 261*: 709–714 (1993).

Symons, "Ribozymes", *Current Opinion in Structural Biology 4*: 322–330 (1994).

Joyce, "In vitro evolution of nucleic acids", *Current Opinion in Structural Biology 4*: 331–336 (1994).

Breaker, et al., "Inventing and improving ribozyme function: rational design versus iterative selection methods", *Tibtech 12*: 268–275 (1994).

Joyce, "Amplification, mutation and selection of catalytic RNA", *Gene 82*: 83–87 (1989).

*Primary Examiner*—George C. Elliott
*Assistant Examiner*—Janet Epps
*Attorney, Agent, or Firm*—Thomas E. Northrup

[57] ABSTRACT

The present invention discloses catalytic or enzymatic DNA molecules that contain a modified nucleotide and that are capable of cleaving nucleic acid sequences or molecules, particularly RNA, in a site-specific manner, as well as compositions including same. Methods of making and using the disclosed enzymes and compositions are also disclosed.

18 Claims, 16 Drawing Sheets

FIG. 2

| Clone | Sequence | Activity |
|---|---|---|
| 16.2-3 | 5'-....CCCGAGGCACCAATCCTTCGTTGAGCTCT-TAGTCGGTGAAACGGCCGCTA....-3' | ++ |
| 16.2-11 | 5'-....CCCAGAAGGCCGAAACCGCTTCGTTGACCCCT-TGCTCTAGGGTTACTAGG....-3' | ++++ |
| 16.2-12 | 5'-....GACAGCAATATCTTCGTTGACCCT-TGCTCTATATAGCCTTCAGGCCCCC....-3' | ++ |
| 16.3-4 | 5'-....CACACGGGACGCATCGGACTTCGTTGAGCACT-TACTCTAGCCGCGCCAT....-3' | +++ |
| 16.4-3 | 5'-....CCACACCGTACACCAGCTCGAGGTTGGGCACC-TACTCTAACACCAGCGGT....-3' | + |
| 16.4-4 | 5'-....GGGACAAAATTGGCCATTAGCCGCGCCTTCGTTGAGCAGGTACACTAGGCCCA....-3' | ++ |
| Consensus | 5'-....CTTCGTTGAGCNCT-TACTCTA....-3' | |

FIG. 9

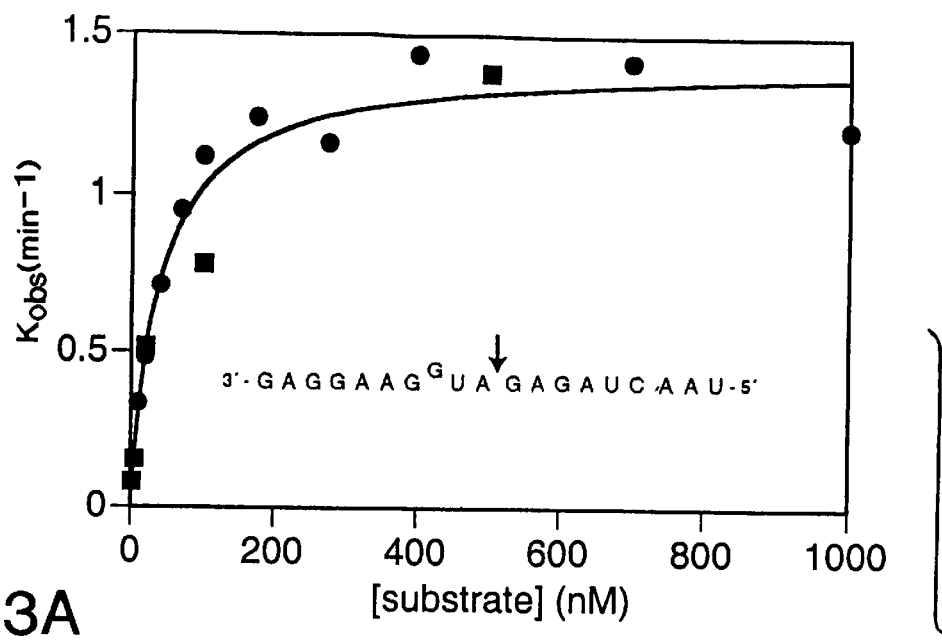
FIG. 13A
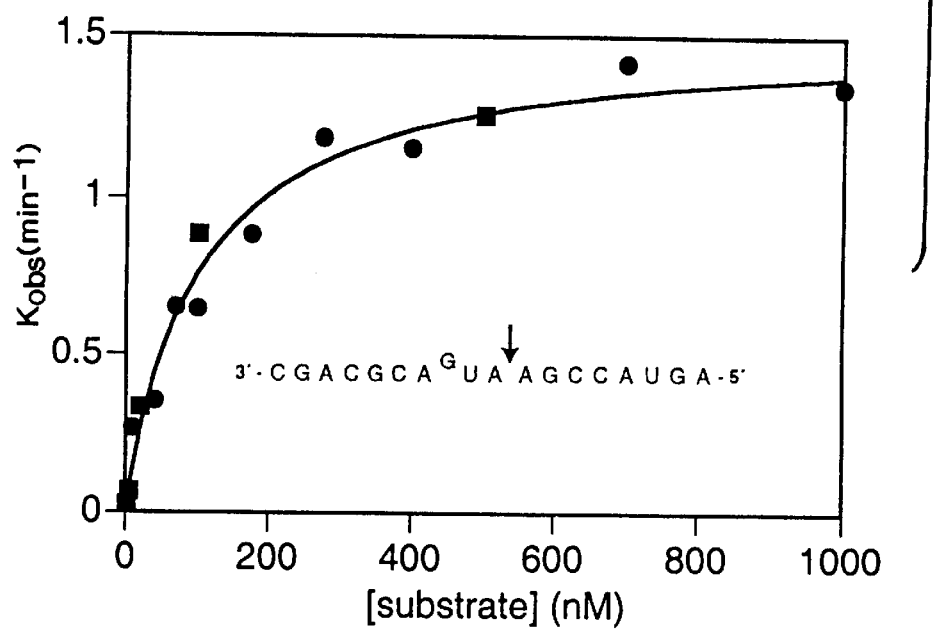
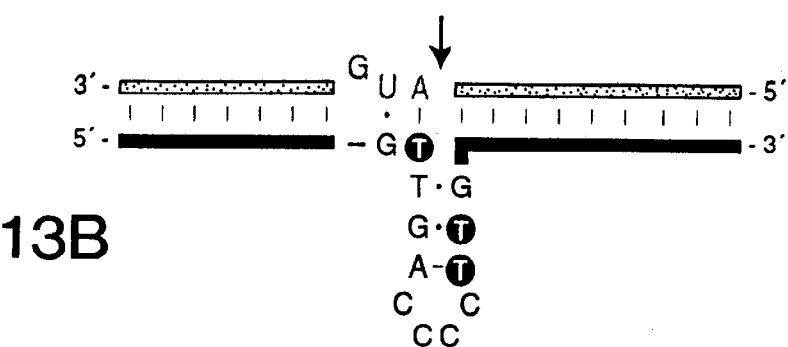
FIG. 13B

ENZYMATIC DNA MOLECULES THAT CONTAIN MODIFIED NUCLEOTIDES

TECHNICAL FIELD

The present invention relates to nucleic acid enzymes or catalytic (enzymatic) DNA molecules that are capable of cleaving RNA and which DNA molecules contain a modified nucleotide. The present invention also relates to compositions containing the disclosed enzymatic DNA molecules and to methods of making and using such enzymes and compositions.

BACKGROUND

The need for catalysts that operate outside of their native context or which catalyze reactions that are not represented in nature has resulted in the development of "enzyme engineering" technology. The usual route taken in enzyme engineering has been a "rational design" approach, relying upon the understanding of natural enzymes to aid in the construction of new enzymes. Unfortunately, the state of proficiency in the areas of protein structure and chemistry is insufficient to make the generation of novel biological catalysts routine.

Recently, a different approach for developing novel catalysts has been applied. This method involves the construction of a heterogeneous pool of macromolecules and the application of an in vitro selection procedure to isolate molecules from the pool that catalyze the desired reaction. Selecting catalysts from a pool of macromolecules is not dependent on a comprehensive understanding of their structural and chemical properties. Accordingly, this process has been dubbed "irrational design" (Brenner and Lerner, *PNAS USA* 89: 5381–5383 (1992)).

Most efforts to date involving the rational design of enzymatic RNA molecules or ribozymes have not led to molecules with fundamentally new or improved catalytic function. However, the application of irrational design methods via a process we have described as "directed molecular evolution" or "in vitro evolution", which is patterned after Darwinian evolution of organisms in nature, has the potential to lead to the production of DNA molecules that have desirable functional characteristics.

This technique has been applied with varying degrees of success to RNA molecules in solution (see, e.g., Mills, et al., *PNAS USA* 58: 217 (1967); Green, et al., *Nature* 347: 406 (1990); Chowrira, et al., *Nature* 354: 320 (1991); Joyce, *Gene* 82: 83 (1989); Beaudry and Joyce, *Science* 257: 635–641 (1992); Robertson and Joyce, *Nature* 344: 467 (1990)), as well as to RNAs bound to a ligand that is attached to a solid support (Tuerk, et al., *Science* 249: 505 (1990); Ellington, et al., *Nature* 346: 818 (1990)). It has also been applied to peptides attached directly to a solid support (Lam, et al., *Nature* 354: 82 (1991)); and to peptide epitopes expressed within a viral coat protein (Scott, et al., *Science* 249: 386 (1990); Devlin, et al., *Science* 249: 249 (1990); Cwirla, et al., *PNAS USA* 87: 6378 (1990)).

It has been more than a decade since the discovery of catalytic RNA (Kruger, et al., *Cell* 31: 147–157 (1982); Guerrier-Takada, et al., Cell 35: 849–857 (1983)). The list of known naturally-occurring ribozymes continues to grow (see Cech, in *The RNA World*, Gesteland & Atkins (eds.), pp. 239–269, Cold Spring Harbor Laboratory Press, Cold Spring Harbor, N.Y. (1993); Pyle, Science 261: 709–714 (1993); *Symons, Curr. Opin. Struct. Biol.* 4: 322–330 (1994)) and, in recent years, has been augmented by synthetic ribozymes obtained through in vitro evolution. (See, e.g., *Joyce, Curr. Opin. Struct. Biol.* 4: 331–336 (1994); Breaker & Joyce, *Trends Biotech.* 12: 268–275 (1994); Chapman & Szostak, *Curr. Opin. Struct. Biol.* 4: 618–622 (1994).)

U.S. Pat. No. 5,807,718 (the disclosure of which is incorporated herein by reference) discloses a synthetic (i.e., non-naturally-occurring) catalytic DNA molecule (or enzymatic DNA molecule) capable of cleaving a substrate nucleic acid sequence at a defined cleavage site. That patent also discloses an enzymatic DNA molecule having an endonuclease activity. In various preferred embodiments, the catalytic DNA molecules of that patent are single-stranded. These catalytic DNA molecules can assume a variety of shapes consistent with their catalytic activity. Thus, in one variation, a catalytic DNA molecule includes one or more hairpin loop structures. In yet another variation, a catalytic DNA molecule may assume a shape similar to that of "hammerhead" ribozymes. An enzymatic DNA molecule of that patent can include a conserved core flanked by one or more substrate binding regions.

In another embodiment, the invention of that patent disclosed a non-naturally-occurring enzymatic DNA molecule comprising a nucleotide sequence defining a conserved core flanked by recognition domains, variable regions, and spacer regions.

Thus, in one preferred embodiment, the nucleotide sequence defined a first variable region contiguous or adjacent to the 5'-terminus of the molecule, a first recognition domain located 3'-terminal to the first variable region, a first spacer region located 3'-terminal to the first recognition domain, a first conserved region located 3'-terminal to the first spacer region, a second spacer region located 3'-terminal to the first conserved region, a second conserved region located 3'-terminal to the second spacer region, a second recognition domain located 3'-terminal to the second conserved region, and a second variable region located 3'-terminal to the second recognition domain.

The invention of that patent further disclosed methods of generating, selecting, and isolating enzymatic DNA molecules. In one variation, a method of selecting enzymatic DNA molecules that cleaved a nucleic acid sequence (e.g., RNA) at a specific site, included the following steps: (a) obtaining a population of synthetic, single-stranded DNA molecules; (b) admixing nucleotide-containing substrate sequences with the population of single-stranded DNA molecules to form an admixture; (c) maintaining the admixture for a sufficient period of time and under predetermined reaction conditions to allow single-stranded DNA molecules in the population to cause cleavage of the substrate sequences, thereby producing substrate cleavage products; (d) separating the population of single-stranded DNA molecules from the substrate sequences and substrate cleavage products; and (e) isolating single-stranded DNA molecules that cleave substrate nucleic acid sequences (e.g., RNA) at a specific site from the population.

Proteins and nucleic acids each have properties that offer unique advantages in performing catalytic transformations (Narlikar & Flerschlag, *Ann. Rev. Biochem.* 66: 19–59, 1997). Proteins possess a wide variety of functional groups that are suited to a broad range of chemical tasks, enabling protein enzymes to achieve extraordinary catalytic rate enhancements. Pancreatic ribonuclease A (RNase A), for example, catalyzes the cleavage of a dinucleotide substrate with a turnover rate of 1400 $s^{-1}$ (delCardayr & Raines, *Biochemistry* 33: 6031–6037, 1994). Nucleic acids, although not endowed with the functional diversity of protein enzymes, are uniquely well suited for the sequence-specific recognition of nucleic acids through Watson-Crick base pairing. This capability allows nucleic acid enzymes to carry out chemical transformations on nucleic acid substrates with high sequence specificity and catalytic efficiency. In *The RNA World*. (Eds. R. F. Gesteland & J. F. Atkins), pp. 271–302. Cold Spring Harbor Laboratory Press, Cold Spring Harbor, N.Y. addition, the substrate-recognition domains of some nucleic acid enzymes can be altered without affecting catalytic activity, allowing them to operate in a general-purpose manner with nucleic acid substrates of almost any desired sequence.

Although nucleic acids are not endowed with diverse functional groups, their functional capabilities can be supplemented by the use of various metal and small-molecule cofactors. The activity of almost all known nucleic acid enzymes is dependent upon or greatly enhanced by divalent metal cations. In most cases, the metal is thought to participate directly in catalysis (for reviews, see Pan et al., 1993; Yarus, *FASEB* 7, 31–39, 1993; Steitz & Steitz, *Proc Natl. Acad. Sci. USA* 90: 6498–6502, 1993; Pyle, *Science* 261: 709–714, 1993; Joyce, *Proc. Natl. Acad. Sci. USA* 95: 5845–5847, 1998). In some cases, however, the metal appears to play an indirect role, perhaps increasing positive charge density within the active site or contributing to the structural integrity of the enzyme (Hampel & Cowan, *Chem. Biol.* 4: 513–517, 1997; Nesbitt et al., *Chem. Biol.* 4: 619–630, 1997; Young et al., *Nucleic Acids Res.* 25: 3760–3766, 1997; Suga et al., *Biochemistry* 37: 10118–10125, 1998; Murray et al., *Chem. Biol.* 5: 587–595, 1998).

The activity of one nucleic acid catalyst developed by in vitro selection is not dependent upon or even affected by the presence of divalent metal ions (Geyer & Sen, *Chem. Biol.* 4: 579–593, 1997). This metal-independent enzyme, however, exhibits a catalytic rate that is substantially lower than that of many of its metal-dependent counterparts. Another in vitro selected DNA enzyme operates without divalent metal in the presence of millimolar concentrations of histidine. The histidine cofactor is thought to serve as a general base in promoting the cleavage of an RNA phosphodiester (Roth & Breaker, *Proc. Natl. Acad. Sci. USA* 95: 6027–6031, 1997). The development of the latter catalyst suggests that nucleic acid enzymes could be made to utilize a wide variety of small-molecule cofactors, greatly expanding their functional capacity. On the other hand, the small molecule cofactor must be bound and correctly positioned for catalysis, which might require an enzyme of greater size and complexity.

The selection of nucleic acid catalysts that contain extended chemical functionality already built into the molecule has been made possible by the development of functionalized NTP analogues that are efficiently incorporated by polymerases. For example, replacement of UTP with a C5-imidazole-substituted UTP analogue enabled the in vitro selection of an imidazole-containing RNA enzyme that catalyzes amide bond formation (Wiegand et al., *Chem. Biol.* 4: 677–683, 1997). In another study, in vitro selection was used to develop a pyridine-functionalized RNA enzyme that catalyzes a Diels-Alder cycloaddition reaction (Tarasow et al., *Nature* 389: 54–57, 1997). Both the amide synthase and Diels-Alderase ribozymes require the functionally-enhanced nucleotides for their catalytic activity. In both cases, however, the role that the added functional groups play in catalysis has not yet been defined.

There are a variety of naturally-occurring RNA enzymes that have the ability to cleave RNA in a sequence-specific manner. These molecules have been used as "catalytic antisense" agents that can be directed to cleave target RNAs both in vitro and in vivo (for reviews, see Christoffersen & Marr, *J. Med. Chem.* 38: 2023–2037, 1995; Rossi, *Biodrugs* 9: 1–10, 1998). RNA enzymes obtained by in vitro evolution might also be used for this purpose (Vaish et al., *Proc. Natl. Acad. Sci. USA* 95: 2158–2162, 1998). Several years ago, the first example of a DNA enzyme was reported; a single-stranded DNA molecule obtained by in vitro selection that cleaves an RNA phosphodiester (Breaker & Joyce, *Chem. Biol.* 1: 223–229, 1994). More recently, a highly efficient, general-purpose RNA-cleaving DNA enzyme was developed (Santoro & Joyce, *Proc. Natl. Acad. Sci. USA* 94: 4262–4265, 1997). This molecule, composed of only ~30 deoxynucleotides requires millimolar concentrations of a divalent metal cation for its catalytic activity. Compared to analogous RNA enzymes, the DNA enzyme is easier to prepare, is more resistant to chemical and enzymatic degradation, and exhibits more favorable kinetic properties (Santoro & Joyce, *Biochemistry* 37: 13330–13342, 1998). It has been applied to the cleavage of a variety of target RNAs, both in vitro (Unrau & Bartel, *Nature* 395: 260–263, 1998) and in vivo.

The lack of a 2' hydroxyl in DNA compared to RNA does not seem to be an impediment to efficient catalytic activity. It is intriguing to speculate, however, what catalytic functions DNA might be able to accomplish if it were endowed with some of the chemical groups that occur in proteins. The development of a family of dNTP derivatives that can be incorporated efficiently into DNA by polymerases (Sakthivel & Barbas, Aizgew. *Chem. Int. Ed.* 37: 2872–2875, 1998) has made it possible to address this question experimentally. As a test case, functionally enhanced DNAs were directed to cleave a target RNA substrate, withholding high concentrations of divalent metal cations, and instead providing imidazole-containing deoxyuridine residues and micromolar amounts of $Zn^{2+}$. An imidazole moiety was chosen in order to confer the same chemical functionality that occurs in the amino acid histidine. Histidine residues are known to play a prominent role in the catalytic mechanism of many protein enzymes, especially ribonucleases and other phosphoesterases (for reviews, see Gerit, In *Nucleases,* 2nd Edition [Eds. S. M. Linn, R. S. Lloyd, & R. J. Roberts], pp. 1–34. Cold Spring Harbor Laboratory Press, Plainview, N.Y., 1993; Lipscomb & Sträter, *Chem. Rev.* 96: 2375–2433, 1996). The $Zn^{2+}$ cofactor was chosen because of its propensity to coordinate to imidazole nitrogens, in both a structural and functional capacity. The resulting imidazole-containing DNA enzyme is a small, but highly efficient general-purpose endoribonuclease. This provides an experimental demonstration of a DNA enzyme that embodies the chemical functionality of a protein enzyme.

BRIEF SUMMARY OF THE INVENTION

In vitro selection techniques were applied to the development of a DNA enzyme that contains three catalytically-essential imidazole groups and catalyzes the cleavage of RNA with a mechanism resembling that of a class of zinc peptidase proteins. Pools for selection were constructed by polymerase-catalyzed incorporation of C5-imidazole-functionalized deoxyuridine in place of thymidine. The catalytic core of the minimized enzyme is composed of only 12 residues, making this one of the smallest nucleic acid catalysts known. The catalytic core forms a compact hairpin structure displaying the three imidazole-containing residues. The enzyme can be made to cleave RNAs of almost any sequence by simple alteration of the two substrate-recognition domains that surround the catalytic core. The enzyme operates with multiple turnover in the presence of micromolar concentrations of $Zn^{2+}$, exhibiting saturation kinetics and a catalytic rate enhancement of $\sim 10^7$-fold compared to the uncatalyzed reaction. The imidazole-containing DNA enzyme combines the substrate-recognition properties of nucleic acid enzymes and the chemical functionality of protein enzymes in a molecule that is small in size, yet versatile and catalytically efficient.

Thus, the resent invention provides a catalytic DNA molecule that specifically cleaves a substrate nucleic acid at a defined cleavage site. The catalytic DNA molecule includes at least one pyrimidine nucleotide of the structure below

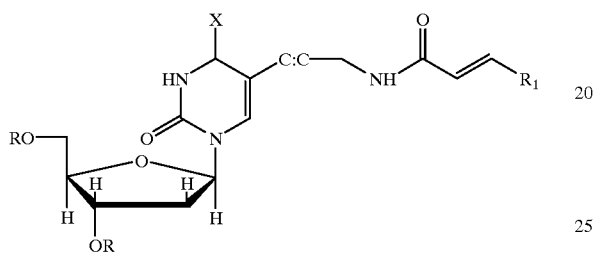

X is $NH_2$ or O, C:C is a carbon-carbon double bond or a carbon-carbon triple bond and each R is independently a cation or

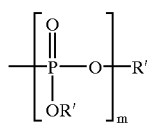

wherein each R' is absent or a cation and m is 1, 2 or 3. $R_1$ is

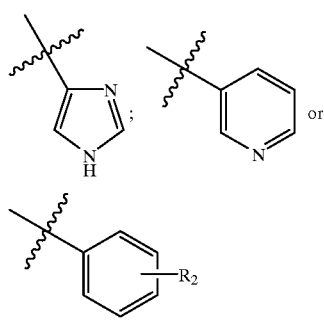

wherein $R_2$ is

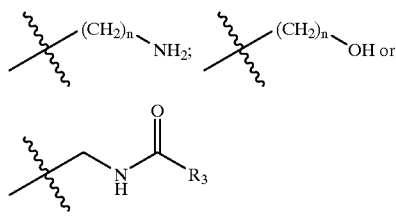

wherein $R_3$ is $(CH_2)_n COOH$ or

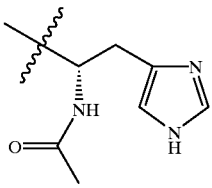

and n is an integer from 0 to 6.

In one preferred embodiment, n is 0, 1 or 2 and at least one R is a cation such as hydrogen or an alkali metal. In another preferred embodiment X is O and C:C is a carbon-carbon double bond. An exemplary and preferred value of R1 is

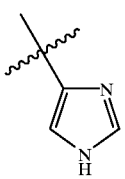

Preferably, the defined cleavage site comprises a single-stranded nucleic acid and the substrate is RNA, DNA, modified RNA, modified DNA, nucleotide analogs, or composites thereof. In one embodiment, the substrate nucleic acid is attached to said catalytic DNA molecule. In a preferred embodiment, the DNA is single-stranded and includes a conserved nucleotide core having one or more conserved nucleotide sequences.

In a particular embodiment, the DNA molecule of this invention includes the nucleotide sequence 5'-GN(N/T)GRSCHCNNR-3'(SEQ ID NO 8) where N is imidazole-deoxyuridylate (Im-dU), R is A or G, S is C or G and H is A, C or T. Preferably, R is A, S is G and H is C. More preferably, S and H are both C.

BRIEF DESCRIPTION OF THE DRAWINGS

FIG. 2 illustrates the sequence alignment of individual variants isolated from the population after five rounds of selection. The fixed substrate domain is shown at the top, with the target riboadenylate identified via an inverted triangle (SEQ ID NO 13). Substrate nucleotides that are commonly involved in presumed base-pairing interactions are indicated by vertical bars. Sequences corresponding to the 50 initially-randomized nucleotides are aligned antiparallel to the substrate domain (SEQ ID NO 14–22). All of the variants are 3'-terminated by the fixed sequence 5'-CGGTAAGCTTGGCAC-3'(SEQ ID NO 1). Nucleotides within the initially-randomized region that are presumed to form base pairs with the substrate domain are indicated on the right and left sides of the Figure; the putative base-pair-forming regions of the enzymatic DNA molecules are individually boxed in each sequence shown. Conserved regions are illustrated via the two large, centrally-located boxes.

FIG. 4A illustrates an exemplary molecule from the starting pool, showing the overall configuration of the molecules represented by SEQ ID NO 23. As illustrated, various complementary nucleotides flank the random ($N_{40}$) region. FIG. 4B is a diagrammatic representation of one of the $Mg^{2+}$-dependent catalytic DNA molecules (or "DNAzymes") generated via the within-described procedures. The location of the ribonucleotide in the substrate nucleic acid is indicated via the arrow in both FIGS. 4A and 4B.

FIGS. 5-1 and 5-2 show the structure of the twenty naturally occurring amino acid residues.

FIG. 9 shows a typical clone from each of the six families obtained following the 16th round of in vitro selection. The designation for each representative corresponds to the round of in vitro selection after which it was cloned (16), the lineage from which it was derived (1–4), and the order in which it was sequenced (SEQ ID NO 48–54). Lineages 1 and 2 were randomly mutagenized prior to the 11th and 14th rounds. Lineages 3 and 4 were not mutagenized. Lineages 1 and 3 were allowed to react in the presence of 1 $\mu$M $Zn^{2+}$ and lineages 2 and 4 in the presence of 10 $\mu$M $Zn^{2+}$. Activity corresponds to the relative rate of self cleavage in the presence of 10 $\mu$M $Zn^{2+}$.

FIGS. 13A–13B show catalytic activity and generalizability of the 16.2-11 imidazone-functionalized DNA enzyme (a) Kinetics of multiple-turnover cleavage by the original form of the enzyme (Residues 3–12 of SEQ ID NO 56 ) or an enzyme designed to cleave an RNA substrate of a different sequence (SEQ ID NO 58) (inset). Reaction conditions: 10 $\mu$M $Zn^{2+}$, 1 mM $Mg^{2+}$, 150 mM NaCl (pH 7.5). (b) Composition of the minimal 16.2-11 catalytic motif (Residues 10–12 of SEQ ID NO 57).

DETAILED DESCRIPTION

A. Definitions

Figure 1:
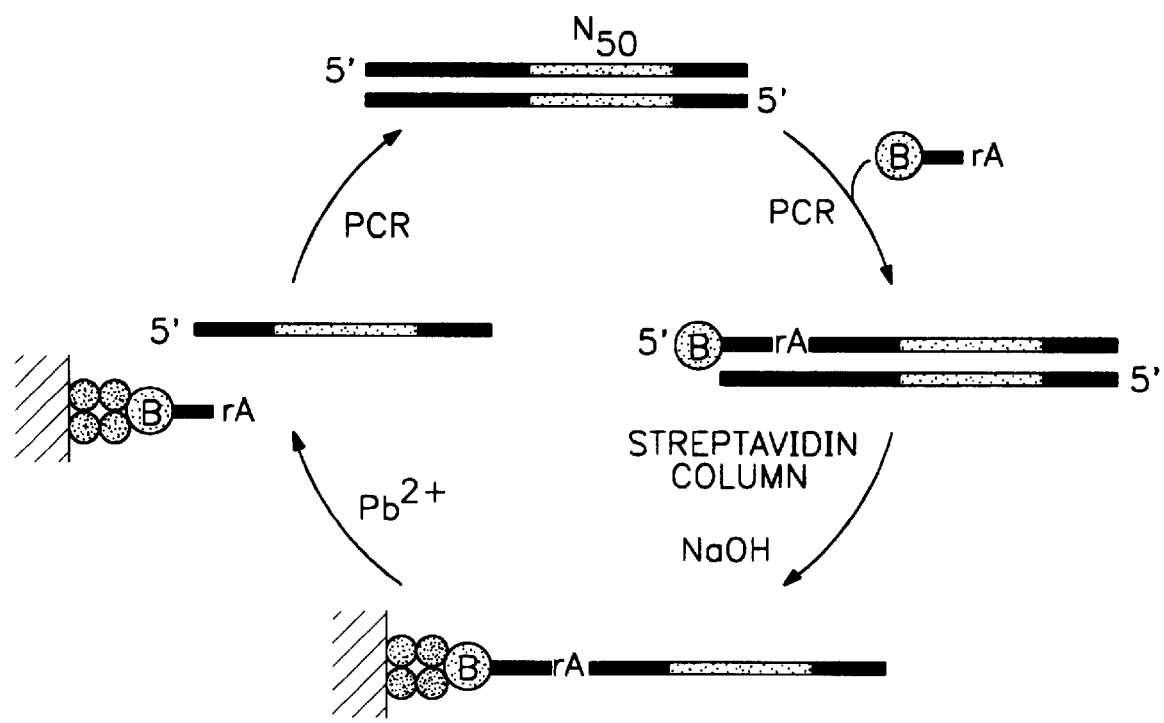
FIG. 1 illustrates a selective amplification scheme for isolation of DNAs that cleave a target RNA phosphoester. As shown, double-stranded DNA that contains a stretch of 50 random nucleotides (the molecule with "$N_{50}$" indicated above it) is amplified by PCR, employing a 5'-biotinylated DNA primer that is terminated at the 3' end by an adenosine ribonucleotide (rA). (The biotin label is indicated via the encircled letter "B".) This primer is extended by Taq polymerase to yield a DNA product that contains a single embedded ribonucleotide. The resulting double-stranded DNA is immobilized on a streptavidin matrix and the unbiotinylated DNA strand is removed by washing with 0.2 N NaOH. After re-equilibrating the column with a buffered solution, the column is washed with the same solution with added 1 mM PbOAc. DNAs that undergo $Pb^{2+}$-dependent self-cleavage are released from the column, collected in the eluant, and amplified by PCR. The PCR products are then used to initiate the next round of selective amplification.

As used herein, the term "deoxyribozyme" is used to describe a DNA-containing nucleic acid that is capable of functioning as an enzyme. In the present disclosure, the term "deoxyribozyme" includes endoribonucleases and endodeoxyribonucleases, although deoxyribozymes with endoribonuclease activity are particularly preferred. Other terms used interchangeably with deoxyribozyme herein are "enzymatic DNA molecule" or "catalytic DNA molecule", which should be understood to include enzymatically active portions thereof, whether they are produced synthetically or derived from organisms or other sources.

The term "enzymatic DNA molecules" also includes DNA molecules that have complementarity in a substrate-binding region to a specified oligonucleotide target or substrate; it also has an enzymatic activity which is active to specifically cleave the oligonucleotide substrate. Stated in another fashion, the enzymatic DNA molecule is capable of cleaving the oligonucleotide substrate intermolecularly. This complementarity functions to allow sufficient hybridization of the enzymatic DNA molecule to the substrate oligonucleotide to allow the intermolecular cleavage of the substrate to occur. While one-hundred percent (100%) complementarity is preferred, complementarity in the range of 75–100% is also useful and contemplated by the present invention. Enzymatic DNA molecules of the present invention may alternatively be described as having nuclease or ribonuclease activity. These terms may be used interchangeably herein.

The term "enzymatic nucleic acid" as used herein encompasses enzymatic RNA or DNA molecules, enzymatic RNA-DNA polymers, and enzymatically active portions or derivatives thereof, although enzymatic DNA molecules are a particularly preferred class of enzymatically active molecules according to the present invention.

The term "endodeoxyribonuclease", as used herein, is an enzyme capable of cleaving a substrate comprised predominantly of DNA. The term "endoribonuclease", as used herein, is an enzyme capable of cleaving a substrate comprised predominantly of RNA.

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G may occasionally participate in base pairings. Nucleotides that normally pair up when DNA or RNA adopts a double stranded configuration may also be referred to herein as "complementary bases".

"Complementary nucleotide sequence" generally refers to a sequence of nucleotides in a single-stranded molecule of DNA or RNA that is sufficiently complementary to that on another single oligonucleotide strand to specifically hybridize to it with consequent hydrogen bonding.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a "nucleoside". When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

"Oligonucleotide or polynucleotide" generally refers to a polymer of single- or double-stranded nucleotides. As used herein, "oligonucleotide" and its grammatical equivalents will include the full range of nucleic acids. An oligonucleotide will typically refer to a nucleic acid molecule comprised of a linear strand of ribonucleotides. The exact size will depend on many factors, which in turn depends on the ultimate conditions of use, as is well known in the art.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35–40° C., with 37° C. being particularly preferred, as well as a pH of about 7.0–8.0, with 7.5 being particularly preferred, and further comprise the availability of cations, preferably divalent and/or monovalent cations, with a concentration of about 2–15 mM $Mg^{2+}$ and 0–1.0 M Na+ being particularly preferred. "Physiologic conditions", as used herein, may optionally include the presence of free nucleoside cofactor. As noted previously, preferred conditions are described in greater detail below.

B. Enzymatic DNA Molecules

In various embodiments, an enzymatic DNA molecule of the present invention may combine one or more modifications or mutations including additions, deletions, and substitutions. In alternative embodiments, such mutations or modifications may be generated using methods which produce random or specific mutations or modifications. These mutations may, for example, change the length of, or alter the nucleotide sequence of, a loop, a spacer region or the recognition sequence (or domain). One or more mutations within one catalytically active enzymatic DNA molecule may be combined with the mutation(s) within a second catalytically active enzymatic DNA molecule to produce a new enzymatic DNA molecule containing the mutations of both molecules.

In other preferred embodiments, an enzymatic DNA molecule of the present invention may have random mutations introduced into it using a variety of methods well known to those skilled in the art. For example, the method described by Cadwell and Joyce (*PCR Methods and Applications* 2: 28–33 (1992)) is particularly preferred for use as disclosed herein, with some modifications, as described in the Examples that follow. (Also see Cadwell and Joyce, *PCR Methods and Applications* 3 (*Suppl.*): St36–S140 (1994).) According to this modified PCR method, random point mutations may be introduced into cloned genes.

The method has been used, for example, to mutagenize the gene encoding the ribozyme with a mutation rate of 0.66% ±0.13% (95% confidence interval) per position, as determined by sequence analysis, with no strong preferences observed with respect to the type of base substitution. This allows the introduction of random mutations at any position in the molecule.

Another method useful in introducing defined or random mutations is disclosed in Joyce and Inoue, *Nucleic Acids Research* 17: 711–722 (1989). This latter method involves excision of a template (coding) strand of a double-stranded DNA, reconstruction of the template strand with inclusion of mutagenic oligonucleotides, and subsequent transcription of the partially-mismatched template. This allows the introduction of defined or random mutations at any position in the molecule by including polynucleotides containing known or random nucleotide sequences at selected positions. Enzymatic DNA molecules of the present invention may be of varying lengths and folding patterns, as appropriate, depending on the type and function of the molecule. For example, enzymatic DNA molecules may be about 15 to about 400 or more nucleotides in length, although a length not exceeding about 250 nucleotides is preferred, to avoid limiting the therapeutic usefulness of molecules by making them too large or unwieldy. In various preferred embodiments, an enzymatic DNA molecule of the present invention is at least about 20 nucleotides in length, and is preferably not more than about 100 nucleotides in length.

In various therapeutic applications, enzymatic DNA molecules of the present invention comprise the enzymatically active portions of deoxyribozymes. In various embodiments, enzymatic DNA molecules of the present invention preferably comprise not more than about 200 nucleotides. In other embodiments, a deoxyribozyme of the present invention comprises not more than about 100 nucleotides, more preferably, not more than about 50 nucleotides in length.

In other applications, enzymatic DNA molecules may assume configurations similar to those of "hammerhead"

ribozymes. Such enzymatic DNA molecules are preferably no more than about 100 nucleotides in length, with a length of about 20–50 nucleotides being particularly preferred.

In general, if one intends to synthesize molecules for use as disclosed herein, the larger the enzymatic nucleic acid molecule is, the more difficult it is to synthesize. Those of skill in the art will certainly appreciate these design constraints.

It is also to be understood that an enzymatic DNA molecule of the present invention may comprise enzymatically active portions of a deoxyribozyme or may comprise a deoxyribozyme with one or more mutations, e.g., with one or more base-pair-forming sequences or spacers absent or modified, as long as such deletions, additions or modifications do not adversely impact the molecule's ability to perform as an enzyme.

The recognition domain of an enzymatic DNA molecule of the present invention typically comprises two nucleotide sequences flanking a catalytic domain, and typically contains a sequence of at least about 3 to about 30 bases, preferably about 6 to about 15 bases, which are capable of hybridizing to a complementary sequence of bases within the substrate nucleic acid giving the enzymatic DNA molecule its high sequence specificity. Modification or mutation of the recognition site via well-known methods allows one to alter the sequence specificity of an enzymatic nucleic acid molecule. (See, e.g, Joyce et al., *Nucleic Acids Research*, 17:711–712 (1989.))

Enzymatic nucleic acid molecules of the present invention include those with altered recognition sites or domains. In various embodiments, these altered recognition domains confer unique sequence specificities on the enzymatic nucleic acid molecule including such recognition domains. The exact bases present in the recognition domain determine the base sequence at which cleavage will take place. Cleavage of the substrate nucleic acid occurs within the recognition domain. This cleavage leaves a 2', 3', or 2',3'-cyclic phosphate group on the substrate cleavage sequence and a 5' hydroxyl on the nucleotide that was originally immediately 3' of the substrate cleavage sequence in the original substrate. Cleavage can be redirected to a site of choice by changing the bases present in the recognition sequence (internal guide sequence). See Murphy et al., *Proc. Natl. Acad. Sci. USA* 86: 9218–9222 (1989).

Moreover, it may be useful to add a polyamine to facilitate recognition and binding between the enzymatic DNA molecule and its substrate. Examples of useful polyamines include spermidine, putrescine or spermine. A spermidine concentration of about 1 mM may be effective in particular embodiments, while concentrations ranging from about 0.1 mM to about 10 mM may also be useful.

In various alternative embodiments, an enzymatic DNA molecule of the present invention has an enhanced or optimized ability to cleave nucleic acid substrates, preferably RNA substrates. As those of skill in the art will appreciate, the rate of an enzyme-catalyzed reaction varies depending upon the substrate and enzyme concentrations and, in general, levels off at high substrate or enzyme concentrations. Taking such effects into account, the kinetics of an enzyme-catalyzed reaction may be described in the following terms, which define the reaction.

The enhanced or optimized ability of an enzymatic DNA molecule of the present invention to cleave an RNA substrate may be determined in a cleavage reaction with varying amounts of labeled RNA substrate in the presence of enzymatic DNA molecule. The ability to cleave the substrate is generally defined by the catalytic rate ($k_{cat}$) divided by the Michaelis constant ($K_M$). The symbol $k_{cat}$ represents the maximal velocity of an enzyme reaction when the substrate approaches a saturation value. $K_M$ represents the substrate concentration at which the reaction rate is one-half maximal.

For example, values for $K_M$ and $k_{cat}$ may be determined in this invention by experiments in which the substrate concentration [S] is in excess over enzymatic DNA molecule concentration [E]. Initial rates of reaction ($v_o$) over a range of substrate concentrations are estimated from the initial linear phase, generally the first 5% or less of the reaction. Data points are fit by a least squares method to a theoretical line given by the equation: $v=-K_M(v_o/[S])+V_{max}$. Thus, $k_{cat}$ and $K_M$ are determined by the initial rate of reaction, $v_o$, and the substrate concentration [S].

In various alternative embodiments, an enzymatic DNA molecule of the present invention has an enhanced or optimized ability to cleave nucleic acid substrates, preferably RNA substrates. In preferred embodiments, the enhanced or optimized ability of an enzymatic DNA molecule to cleave RNA substrates shows about a $10^3$- to $10^9$-fold improvement over the uncatalyzed rate. In more preferred embodiments, an enzymatic DNA molecule of the present invention is able to cleave RNA substrates at a rate that is about $10^3$- to $10^7$-fold improved over "progenitor" species. In even more preferred embodiments, the enhanced or optimized ability to cleave RNA substrates is expressed as a $10^4$- to $10^6$-fold improvement over the progenitor. One skilled in the art will appreciate that the enhanced or optimized ability of an enzymatic DNA molecule to cleave nucleic acid substrates may vary depending upon the selection constraints applied during the in vitro evolution procedure of the invention.

Various preferred methods of modifying deoxyribozymes and other enzymatic DNA molecules and nucleases of the present invention are further described in the Examples hereinbelow.

C. Modified Nucleotide

A nucleotide (e.g., pyrimidine) is modified at the C5-position. More particularly, the C5-position is derivatized to contain a side chain. The side chain at the C5-position is designed and prepared to mimic the chemical and biological properties of an amino acid residue. FIG. x shows the structure of the twenty naturally occurring amino acid residues. In a preferred embodiment, the side chain mimics the properties of a polar amino acid residue. Thus, it is preferred that the side chain on the pyrimidine imparts a positive or negative charge onto the base.

In accordance with this embodiment, a nucleotide containing the modified base, when incorporated into a DNA molecule, imparts an electrostatic charge into the DNA. The functional groups of the natural nucleic acids have $pK_a$'s far removed from neutral pH and are therefore not suited for general acid-base catalysis in this pH range. Use of the modified nucleotides described herein provides potential for covalent, electrostatic, and an expanded potential for metal ion catalysis. This charge enhances the aptameric nature of the DNA (i.e., ability of DNA to interact with and bind polypeptides). The amino acid residue functional group is appended to the C5 position of the pyrimidine by means of a linker moiety. The linker moiety is an unsaturated hydrocarbon chain that includes an amide bond and a ketone group. A linker moiety shown to be suitable for linking a pyrimidine to functional groups has the structure shown below.

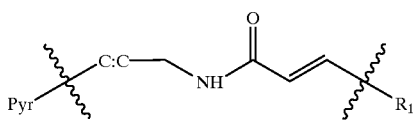

where Pyr is pyrimidine, $R_1$ is a functional group and C:C represents a carbon-carbon double bond or a carbon-carbon triple bond. In a preferred embodiment, C:C is a carbon-carbon double bond. Thus, a modified pyrimidine of the present invention has the structure I, shown below

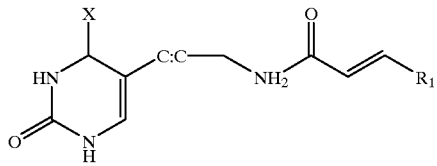

where X is NH2 or O, C:C is an unsaturated carbon bond and $R_1$ is

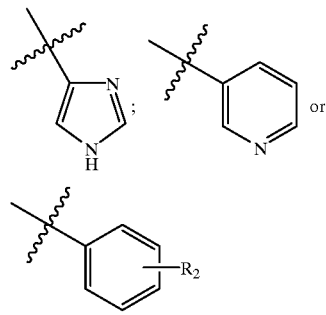

wherein $R_2$ is

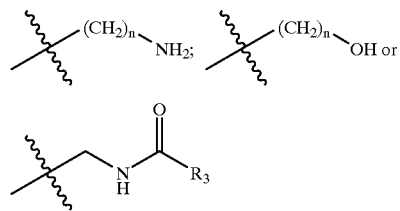

wherein $R_3$ is
$(CH_2)_n COOH$ or

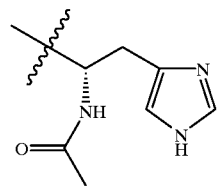

and n is an integer from 0 to 6. Preferably n is 0, 1 or 2.

Nucleosides and nucleotides of the present invention contain the modified pyrimidine as set forth above in Structure I. In addition, the modified nucleosides and nucleotides comprise a ribose sugar. The ribose can be hydroxylated or non-hydroxylated at the 2'-position. In a preferred embodiment, the hydroxyl group at the 2'-position of the ribose is lacking and the sugar moiety is a dexoyribose. In accordance with this preferred embodiment, a modified nucleoside/nucleotide of this invention has the structure II, below

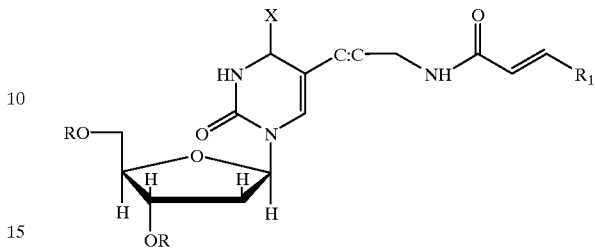

where X, C:C and $R_1$ are as defined above with regard to Structure I and each R is independently a cation or

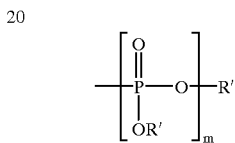

wherein each R' is independently absent or a cation and m is 1, 2, or 3. The cation of R and R' is preferably a monovalent cation such as hydrogen or an alkali metal salt such as sodium (Na), potassium (K) or lithium (Li).

Figure 6:
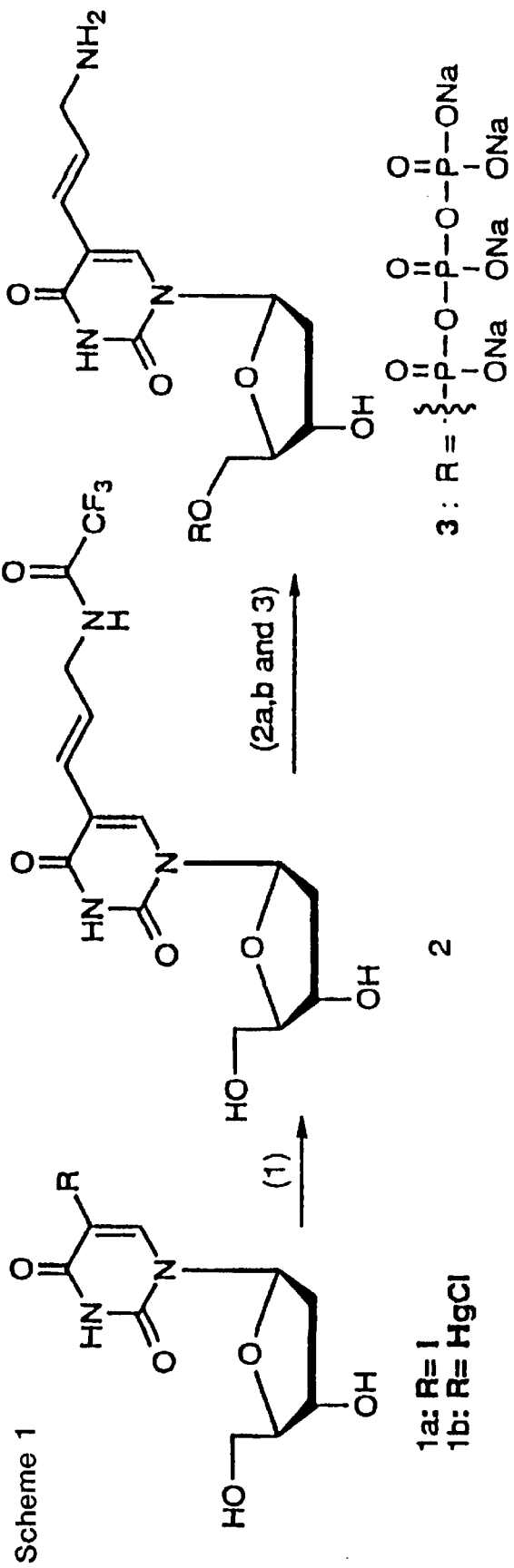
FIG. 6 shows a synthetic scheme for making a nucleotide triphosphate precursor

A modified nucleotide of the present invention can be made using a variety of synthetic procedures (See Scheme I, FIG. 6). A synthetic process begins with the synthesis of C-5(3-aminopropenyl)-2'deoxyuridine triphosphate or C-5 (3-aminopropenyl)-2'deoxycytosine triphosphate from known compounds. Scheme I, FIG. 6 shows the synthesis of C-5(3-aminopropenyl)-2'deoxyuridine triphosphate from known compound 2. A palladium catalyzed route starting from commercially available 5-iododeoxyuridine was found to be preferable to the earlier synthetic scheme of Cook et al. (A. F. Cook, E. Vuocolo, C. L. Brakel, *Nucleic Acids Res.* 1988, 16, 4077–95) starting with 5-chloromercuri-2' deoxyuridine, though both provided 2 in similar yields. Optimization of the synthesis of 2 and its conversion to the corresponding 5'-triphosphate using the methodology of Kovács and Ötvös (T. Kovacs, L. Otvos, *Tetrahedron Lett.* 1988, 29, 4525–8.) followed by deprotection of the amine provided 3 isolated on a 100 mg scale with analytical purity. Compound 3 was synthesized previously from deoxyuridine triphosphate (dUTP), however, problems with contaminating byproducts and the expense of dUTP as a starting material posed serious obstacles for this synthetic route (P. R. Langer, A. A. Waldrop, D. C. Ward, *Proc. Natl. Acad. Sci. U. S. A.* 1981, 78, 6633–7). A detailed description of the synthesis of Compounds 2 and 3 can be found hereinafter in the Examples. Compound 3 was then used as the starting material for preparation of modified deoxyuridine nucleotides using standard techniques well known in the art. Those modified deoxyuridine nucleotides are shown in Scheme 2, FIG. 7. Detailed descriptions of the preparation of numerous modified nucleotides can be found hereinafter in the Examples.

In a related aspect, the present invention provides an enzymatic DNA molecule that comprises a modified nucleotide as set forth above. The DNA molecule can contain a plurality of modified nucleotides. A DNA molecule of this invention can be a single stranded or double stranded molecule. Where the DNA molecule is double stranded, the modified nucleotide(s) can be included in one or both strands.

A DNA molecule containing a modified nucleotide as set forth above can be made using standard procedures well known in the art such as solid phase phosphoramidite chemistry. All that is needed is to use a modified nucleotide of this invention in the synthetic scheme. A modified nucleotide of this invention can also be incorporated into a DNA molecule using enzymes such as polymerases and reverse transcriptases. A reaction mixture for making a DNA molecule comprises one or more modified nucleotides of this invention together with dATP, (1GTP, dTTP and dCTP. The modified nucleotides can be in addition to or replace dTTP and/or dCTP.

D. Methods of Engineering Enzymatic DNA Molecules

The present invention also contemplates methods of producing nucleic acid molecules having a predetermined activity. In one preferred embodiment, the nucleic acid molecule is an enzymatic DNA molecule. In another variation, the desired activity is a catalytic activity.

In one embodiment, the present invention contemplates methods of synthesizing enzymatic DNA molecules that may then be "engineered" to catalyze a specific or predetermined reaction. Methods of preparing enzymatic DNA molecules are described herein below in the Examples. In other embodiments, an enzymatic DNA molecule of the present invention may be engineered to bind small molecules or ligands, such as adenosine triphosphate (ATP). (See, e.g., Sassanfar, et al., Nature 364: 550–553 (1993).)

In another embodiment, the present invention contemplates that a population of enzymatic DNA molecules may be subjected to mutagenizing conditions to produce a diverse population of mutant enzymatic DNA molecules (which may alternatively be called "deoxyribozymes"). Thereafter, enzymatic DNA molecules having desired characteristics are selected and/or separated from the population and are subsequently amplified.

Alternatively, mutations may be introduced in the enzymatic DNA molecule by altering the length of the recognition domains of the enzymatic DNA molecule. The recognition domains of the enzymatic DNA molecule associate with a complementary sequence of bases within a substrate nucleic acid sequence. Methods of altering the length of the recognition domains are known in the art and include PCR, for example; useful techniques are described further in the Examples below.

Alteration of the length of the recognition domains of an enzymatic DNA molecule may have a desirable effect on the binding specificity of the enzymatic DNA molecule. For example, an increase in the length of the recognition domains may increase binding specificity between the enzymatic DNA molecule and the complementary base sequences of an oligonucleotide in a substrate, or may enhance recognition of a particular sequence in a hybrid substrate. In addition, an increase in the length of the recognition domains may also increase the affinity with which it binds to substrate. In various embodiments, these altered recognition domains in the enzymatic DNA molecule confer increased binding specificity and affinity between the enzymatic DNA molecule and its substrate.

It has recently been noted that certain oligonucleotides are able to recognize and bind molecules other than oligonucleotides with complementary sequences. These oligonucleotides are often given the name "aptamers". For example, Ellington and Szostak describe RNA molecules that are able to bind a variety of organic dyes (Nature 346: 818–822 (1990)), while Bock, et al. describe ssDNA molecules that bind human thrombin (Nature 355: 564–566 (1992)). Similarly, Jellinek, et al. describe RNA ligands to basic fibroblast growth factor (PNAS USA 90: 11227–11231 (1993)). Thus, it is further contemplated herein that the catalytically active DNA enzymes of the present invention may be engineered according to the within-described methods to display a variety of capabilities associated with aptamers.

One of skill in the art should thus appreciate that the enzymatic DNA molecules of this invention can be altered at any nucleotide sequence, such as the recognition domains, by various methods disclosed herein, including PCR and 3SR. For example, additional nucleotides can be added to the 5' end of the enzymatic DNA molecule by including additional nucleotides in the primers.

Enzymatic DNA molecules of the present invention may also be prepared or engineered in a more non-random fashion via use of methods such as site-directed mutagenesis. For example, site-directed mutagenesis may be carried out essentially as described in Morinaga, et al., Biotechnology 2: 636 (1984), modified as described herein, for application to deoxyribozymes. Useful methods of engineering enzymatic DNA molecules are further described in the Examples below.

In one disclosed embodiment, an enzymatic DNA molecule of the present invention comprises a conserved core flanked by two substrate binding (or recognition) domains or sequences that interact with the substrate through base-pairing interactions. In various embodiments, the conserved core comprises one or more conserved domains or sequences. In another variation, an enzymatic DNA molecule further comprises a "spacer" region (or sequence) between the regions (or sequences) involved in base pairing. In still another variation, the conserved core is "interrupted" at various intervals by one or more less-conserved variable or "spacer" nucleotides.

In various embodiments, the population of enzymatic DNA molecules is made up of at least 2 different types of deoxyribozyme molecules. For example, in one variation, the molecules have differing sequences. In another variation, the deoxyribozymes are nucleic acid molecules having a nucleic acid sequence defining a recognition domain that is contiguous or adjacent to the 5'-terminus of the nucleotide sequence. In various alternative embodiments, enzymatic DNA molecules of the present invention may further comprise one or more spacer regions located 3'-terminal to the recognition domains, one or more loops located 3'-terminal to the recognition domains and/or spacer regions. In other variations, a deoxyribozyme of the present invention may comprise one or more regions which are capable of hybridizing to other regions of the same molecule. Other characteristics of enzymatic DNA molecules produced according to the presently-disclosed methods are described elsewhere herein.

In other embodiments, mutagenizing conditions include conditions that introduce either defined or random nucleotide substitutions within an enzymatic DNA molecule. Examples of typical mutagenizing conditions include conditions disclosed in other parts of this specification and the methods described by Joyce et al., Nucl. Acids Res. 17: 711–722 (1989); Joyce, Gene 82: 83–87(1989); and Beaudry and Joyce, Science 257: 635–41 (1992).

In still other embodiments, a diverse population of mutant enzymatic nucleic acid molecules of the present invention is one that contains at least 2 nucleic acid molecules that do not have the exact same nucleotide sequence. In other variations, from such a diverse population, an enzymatic DNA molecule or other enzymatic nucleic acid having a predetermined activity is then selected on the basis of its ability to perform the predetermined activity. In various embodiments, the predetermined activity comprises, without limitation, enhanced catalytic activity, decreased $K_M$, enhanced substrate binding ability, altered substrate specificity, and the like.

Other parameters which may be considered aspects of enzyme performance include catalytic activity or capacity, substrate binding ability, enzyme turnover rate, enzyme sensitivity to feedback mechanisms, and the like. In certain aspects, substrate specificity may be considered an aspect of enzyme performance, particularly in situations in which an enzyme is able to recognize and bind two or more competing substrates, each of which affects the enzymes' performance with respect to the other substrate(s).

Substrate specificity, as used herein, may refer to the specificity of an enzymatic nucleic acid molecule as described herein for a particular substrate, such as one comprising ribonucleotides only, deoxyribonucleotides only, or a composite of both. Substrate molecules may also contain nucleotide analogs. In various embodiments, an enzymatic nucleic acid molecule of the present invention may preferentially bind to a particular region of a hybrid or non-hybrid substrate.

The term or parameter identified herein as "substrate specificity" may also include sequence specificity; i.e., an enzymatic nucleic acid molecule of the present invention may "recognize" and bind to a nucleic acid substrate having a particular nucleic acid sequence. For example, if the substrate recognition domains of an enzymatic nucleic acid molecule of the present invention will only bind to substrate molecules having a series of one or two ribonucleotides (e.g., rA) in a row, then the enzymatic nucleic acid molecule will tend not to recognize or bind nucleic acid substrate molecules lacking such a sequence.

With regard to the selection process, in various embodiments, selecting includes any means of physically separating the mutant enzymatic nucleic acids having a predetermined activity from the diverse population of mutant enzymatic nucleic acids. Often, selecting comprises separation by size, by the presence of a catalytic activity, or by hybridizing the mutant nucleic acid to another nucleic acid, to a peptide, or some other molecule that is either in solution or attached to a solid matrix.

In various embodiments, the predetermined activity is such that the mutant enzymatic nucleic acid having the predetermined activity becomes labelled in some fashion by virtue of the activity. For example, the predetermined activity may be an enzymatic DNA molecule activity whereby the activity of the mutant enzymatic nucleic acid upon its substrate causes the mutant enzymatic nucleic acid to become covalently linked to it. The mutant enzymatic nucleic acid is then selected by virtue of the covalent linkage.

In other embodiments, selecting a mutant enzymatic nucleic acid having a predetermined activity includes amplification of the mutant enzymatic nucleic acid (see, e.g., Joyce, *Gene* 82: 83–87 (1989); Beaudry and Joyce, *Science* 257: 635–41 (1992)). Other methods of selecting an enzymatic nucleic acid molecule having a predetermined characteristic or activity are described in the Examples section.

E. Compositions

The invention also contemplates compositions containing one or more types or populations of enzymatic DNA molecules of the present invention; e.g., different types or populations may recognize and cleave different nucleotide sequences. Compositions may further include a ribonucleic acid-containing substrate. Compositions according to the present invention may further comprise lead ion, magnesium ion, or other divalent or monovalent cations, as discussed herein.

Preferably, the enzymatic DNA molecule is present at a concentration of about 0.05 $\mu$M to about 2 $\mu$M. Typically, the enzymatic DNA molecule is present at a concentration ratio of enzymatic DNA molecule to substrate of from about 1:5 to about 1:50. More preferably, the enzymatic DNA molecule is present in the composition at a concentration of about 0.1 $\mu$M to about 1 $\mu$M. Even more preferably, compositions contain the enzymatic DNA molecule at a concentration of about 0.1 $\mu$M to about 0.5 $\mu$M. Preferably, the substrate is present in the composition at a concentration of about 0.5 $\mu$M to about 1000 $\mu$M. One skilled in the art will understand that there are many sources of nucleic acid-containing substrates including naturally-occurring and synthetic sources. Sources of suitable substrates include, without limitation, a variety of viral and retroviral agents, including HIV-1, HIV-2, HTLV-I, and HTLV-II.

Other suitable substrates include, without limitation, viral and retroviral agents including those comprising or produced by picornaviruses, hepadnaviridae (e.g., HBV HCV), papillomaviruses (e.g., HPV), gammaherpesvirinae (e.g., EBV), lymphocryptoviruses, leukemia viruses (e.g., HTLV-I and -II), flaviviruses, togaviruses, herpesviruses (including alphaherpesviruses and betaherpesviruses), cytomegaloviruses (CMV), influenza viruses, and viruses and retrovirilses contributing to immunodeficiency diseases and syndromes (e.g., HIV-1 and -2). In addition, suitable substrates include viral and retroviral agents which infect non-human primates, including, without limitation, the simian and feline immunodeficiency viruses and bovine leukemia viruses.

Magnesium ion, lead ion, or another suitable monovalent or divalent cation, as described previously, may also be present in the composition, at a concentration of about 1–100 mM. More preferably, the preselected ion is present in the composition at a concentration of about 2 mM to about 50 mM, with a concentration of about 5 mM being particularly preferred. One skilled in the art will understand that the ion concentration is only constrained by the limits of solubility of it source (e.g. magnesium) in aqueous solution and a desire to have the enzymatic DNA molecule present in the same composition in an active conformation.

The invention also contemplates compositions containing an enzymatic DNA molecule of the present invention, hybrid deoxyribonucleotide-ribonucleotide molecules, and magnesium or lead ion in concentrations as described hereinabove. As noted previously, other monovalent or divalent ions (e.g., $Ca^{2+}$) may be used in place of magnesium.

Also contemplated by the present invention are compositions containing an enzymatic DNA molecule of the present invention, nucleic acid-containing substrate (e.g. RNA), and a preselected ion at a concentration of greater than about 1 millimolar, wherein said substrate is greater in length than the recognition domains present on the enzymatic DNA molecule.

In one variation, a composition comprises an enzymatic DNA molecule-substrate complex, wherein base pairing between an enzymatic DNA molecule and its substrate is contiguous. In another embodiment, base pairing between an enzymatic DNA molecule and its substrate is interrupted by one or more noncomplementary pairs.

In a variety of alternative embodiments, a composition of the present invention may further comprise a monovalent cation, a divalent cation, both, or neither.

In another variation, an enzymatic DNA molecule of the present invention is capable of functioning efficiently in the presence or absence of a divalent cation. In one variation, a divalent cation is present and comprises $Pb^{2+}$, $Mg^{2+}$, $Mn^{2+}$, $Zn^{2+}$, or $Ca^{2+}$. Alternatively, an enzymatic DNA molecule of the present invention is capable of functioning efficiently in the presence or absence of divalent cations. It is anticipated that cation concentrations similar to those described herein for $Pb^{2+}$ will be useful as disclosed herein.

Optionally, monovalent cations may also be present in addition to, or as "alternatives" for, divalent cations. For example, monovalent cations such as sodium ($Na^+$) or potassium ($K^+$) may be present, either as dissociated ions or in the form of dissociable compounds such as NaCl or KCl.

In one embodiment, the concentration of monovalent cation present in the composition ranges from 0–1.0 M. In another embodiment, a monovalent cation is present in a concentration ranging from about 0–200 mM. In other embodiments, monovalent cations are present in a concentration ranging from about 1–100 mM. Alternatively, the concentration of monovalent cations ranges from about 2 mM–50 mM. In still other embodiments, the concentration ranges from about 2 mM–25 mM.

F. Methods of Using Enzymatic DNA Molecules

The methods of using enzymatic DNA molecules as disclosed herein are legion. As discussed previously, molecules capable of cleaving the bonds linking neighboring nucleic acids (e.g., phosphoester bonds) have numerous uses encompassing a wide variety of applications. For example, enzymatic DNA molecules having the within-disclosed capabilities, structures, and/or functions are useful in pharmaceutical and medical products (e.g., for wound debridement, clot dissolution, etc.), as well as in household items (e.g., detergents, dental hygiene products, meat tenderizers). Industrial utility of the within-disclosed compounds, compositions and methods is also contemplated and well within the scope of the present invention.

The present invention also describes useful methods for cleaving any single-stranded, looped, partially or fully double-stranded nucleic acid; the majority of these methods employ the novel enzymatically active nucleic acid molecules of the present invention. In various embodiments, the single-stranded nucleic acid segment or portion of the substrate (or the entire substrate itself) comprises DNA, modified DNA, RNA, modified RNA, or composites thereof. The nucleic acid substrate must only be single-stranded at or near the substrate cleavage sequence so that an enzymatic nucleic acid molecule of the present invention can hybridize to the substrate cleavage sequence by virtue of the enzyme's recognition sequence.

A nucleic acid substrate that can be cleaved by a method of this invention may be chemically synthesized or enzymatically produced, or it may be isolated from various sources such as phages, viruses, prokaryotic cells, or eukaryotic cells, including animal cells, plant cells, eukaryotic cells, yeast cells and bacterial cells. Chemically synthesized single-stranded nucleic acids are commercially available from many sources including, without limitation, Research Genetics (Huntsville, Ala.).

RNA substrates may also be synthesized using an Applied Biosystems (Foster City, Calif.) oligonucleotide synthesizer according to the manufacture's instructions. Single-stranded phages are also sources of nucleic acid substrates. (See, e.g., Messing et al., *PNAS USA* 74: 3642–3646 (1977), and Yanisch-Perron et al., *Gene* 33: 103–119 (1985).) Bacterial cells containing single-stranded phages would also be a ready source of suitable single-stranded nucleic acid.

Single-stranded RNA cleavable by a method of the present invention could be provided by any of the RNA viruses such as the picornaviruses, togaviruses, orthomyxoviruses, paramyxoviruses, rhabdoviruses, coronaviruses, arenaviruses or retroviruses. As noted previously, a wide variety of prokaryotic and eukaryotic cells may also be excellent sources of suitable nucleic acid substrates.

The methods of this invention may be used on single-stranded nucleic acids or single-stranded portions of looped or double-stranded nucleic acids that are present inside a cell, including eucaryotic, procaryotic, plant, animal, yeast or bacterial cells. Under these conditions an enzymatic nucleic acid molecule (e.g., an enzymatic DNA molecule or deoxyribozyme) of the present invention could act as an anti-viral agent or a regulator of gene expression. Examples of such uses of enzymatic DNA molecules of the present invention are described further hereinbelow.

In the majority of methods of the present invention, cleavage of single-stranded nucleic acids occurs at the 3'-terminus of a predetermined base sequence. This predetermined base sequence or substrate cleavage sequence typically contains from 1 to about 10 nucleotides. In other preferred embodiments, an enzymatic DNA molecule of the present invention is able to recognize nucleotides either upstream, or upstream and downstream of the cleavage site. In various embodiments, an enzymatic DNA molecule is able to recognize about 2–10 nucleotides upstream of the cleavage site; in other embodiments, an enzymatic DNA molecule is able to recognize about 2–10 nucleotides upstream and about 2–10 nucleotides downstream of the cleavage site. Other preferred embodiments contemplate an enzymatic DNA molecule that is capable of recognizing a nucleotide sequence up to about 30 nucleotides in length, with a length up to about 20 nucleotides being even more preferred.

The within-disclosed methods allow cleavage at any nucleotide sequence by altering the nucleotide sequence of the recognition domains of the enzymatic DNA molecule. This allows cleavage of single-stranded nucleic acid in the absence of a restriction endonuclease site at that position.

An enzymatic DNA molecule of the present invention may be separated from the remainder of the single-stranded nucleic acid substrate by site-specific hydrolysis at the appropriate cleavage site. Separation of the enzymatic DNA molecule from the substrate allows the enzymatic DNA molecule to carry out another cleavage reaction.

Generally, the nucleic acid substrate is treated under appropriate nucleic acid cleaving conditions—preferably, physiologic conditions—with an effective amount of an enzymatic DNA molecule of the present invention. If the nucleic acid substrate comprises DNA, cleaving conditions may include the presence of a divalent cation at a concentration of about 2–10 mM.

An effective amount of an enzymatic DNA molecule is the amount required to cleave a predetermined base sequence present within the single-stranded RNA. Preferably, the enzymatic DNA molecule is present at a molar ratio of DNA molecule to substrate cleavage sites of 1 to 20. This ratio may vary depending on the length of treating and efficiency of the particular enzymatic DNA molecule under the particular RNA cleavage conditions employed.

Treating typically involves admixing, in aqueous solution, the RNA-containing substrate and the enzyme to form a cleavage admixture, and then maintaining the admixture thus formed under RNA cleaving conditions for a time period sufficient for the enzymatic DNA molecule to cleave the RNA substrate at any of the predetermined nucleotide sequences present in the RNA. In various embodiments, a source of ions is also provided—i.e. monovalent or divalent cations, or both.

In one embodiment of the present invention, the amount of time necessary for the enzymatic DNA molecule to cleave the single-stranded nucleic acid has been predetermined. The amount of time is from about 1 minute to about 24 hours and will vary depending upon the concentration of the reactants, and the temperature of the reaction. Usually, this time period is from about 10 minutes to about 2 hours such that the enzymatic DNA molecule cleaves the single-stranded nucleic acid at any of the predetermined nucleotide sequences present.

The invention further contemplates that the nucleic acid cleaving conditions include the presence of a source of divalent cations (e.g., PbOAc) at a concentration of about 2–100 mM. Typically, the nucleic acid cleaving conditions include divalent cation at a concentration of about 2 mM to about 10 mM, with a concentration of about 5 mM being particularly preferred.

The optimal cationic concentration to include in the nucleic acid cleaving conditions can be easily determined by determining the amount of single-stranded nucleic acid cleaved at a given cation concentration. One skilled in the art will understand that the optimal concentration may vary depending on the particular enzymatic DNA molecule employed.

The present invention further contemplates that the nucleic acid cleaving conditions are at from about pH 6.0 to about pH 9.0. In one preferred embodiment, the pH ranges from about pH 6.5 to pH 8.0. In another preferred embodiment, the pH emulates physiological conditions, i.e., the pH is about 7.0–7.8, with a pH of about 7.5 being particularly preferred.

One skilled in the art will appreciate that the methods of the present invention will work over a wide pH range so long as the pH used for nucleic acid cleaving is such that the enzymatic DNA molecule is able to remain in an active conformation. An enzymatic DNA molecule in an active conformation is easily detected by its ability to cleave single-stranded nucleic acid at a predetermined nucleotide sequence.

In various embodiments, the nucleic acid cleaving conditions also include a variety of temperature ranges; as noted previously, temperature ranges consistent with physiological conditions are especially preferred. In one embodiment, the temperature ranges from about 15° C. to about 60° C. In another variation, the nucleic acid cleaving conditions are from about 30° C. to about 56° C. The temperature of the nucleic acid cleaving conditions are constrained only by the desired cleavage rate and the stability of that particular enzymatic DNA molecule at that particular temperature. In yet another variation, nucleic acid cleavage conditions include a temperature from about 35° C. to about 50° C. In a preferred embodiment, nucleic acid cleavage conditions comprise a temperature range of about 37° C. to about 42° C.

In various methods, the present invention contemplates nucleic acid cleaving conditions including the presence of a polyamine. Polyamines useful for practicing the present invention include spermidine, putrescine, spermine and the like. In one variation, the polyamine is spermidine and it is present at a concentration of about 0.01 mM to about 10 mM. In another variation, the polyamine is present at a concentration of about 1 mM to about 10 mM. Nucleic acid cleavage conditions may also include the presence of polyamine at a concentration of about 2: mM to about 5 mM. In various preferred embodiments, the polyamine is spermidine.

G. Vectors

The present invention also features expression vectors including a nucleic acid segment encoding an enzymatic DNA molecule of the present invention situated within the vector, preferably in a manner which allows expression of that enzymatic DNA molecule within a target cell (e.g., a plant or animal cell).

Thus, in general, a vector according to the present invention preferably includes a plasmid, cosmid, phagemid, virus, or phage vector. Preferably, suitable vectors comprise single-stranded DNA (ssDNA)—e.g., circular phagemid ssDNA. It should also be appreciated that useful vectors according to the present invention need not be circular.

In one variation, nucleotide sequences flanking each of the additional enzymatic DNA molecule-encoding sequences are preferably provided, which sequences may be recognized by the first enzymatic DNA molecule. The intervening or flanking sequences preferably comprise at least 1 nucleotide:; more preferably, intervening or flanking sequences are about 2–20 nucleotides in length, with sequences of about 5–10 nucleotides in length being particularly preferred.

The addition of polynucleotide tails may also be useful to protect the 3' end of an enzymatic DNA molecule according to the present invention. These may be provided by attaching a polymeric sequence by employing the enzyme terminal transferase.

A vector according to the present invention includes two or more enzymatic DNA molecules. In one embodiment, a first enzymatic DNA molecule has intramolecular cleaving activity and is able to recognize and cleave nucleotide sequences to release other enzymatic DNA sequences; i.e., it is able to function to "release" other enzymatic DNA molecules from the vector. For example, a vector is preferably constructed so that when the first enzymatic DNA molecule is expressed, that first molecule is able to cleave nucleotide sequences flanking additional nucleotide sequences encoding a second enzymatic DNA molecule, a third enzymatic DNA molecule, and so forth. Presuming said first enzymatic DNA molecule (i.e., the "releasing" molecule) is able to cleave oligonucleotide sequences intramolecularly, the additional (e.g. second, third, and so on) enzymatic DNA molecules (i.e., the "released" molecules) need not possess characteristics identical to the "releasing" molecule. Indeed, in various preferred embodiments, the "released" (i.e. second, third, etc.) enzymatic DNA molecule has amide bond-cleaving activity, while the first ("releasing") enzymatic DNA molecule has nuclease activity.

Alternatively, the first enzymatic DNA molecule may be encoded on a separate vector from the second enzymatic DNA molecule(s) and may have intermolecular cleaving activity. As noted herein, the first enzymatic DNA molecule can be a self-cleaving enzymatic DNA molecule (e.g., a deoxyribozyme), and the second enzymatic DNA molecule may be any desired type of enzymatic DNA molecule (e.g., a deoxyribozyme). When a vector is caused to express RNA from these nucleic acid sequences, that RNA has the ability under appropriate conditions to cleave each of the flanking regions, thereby releasing one or more copies of the second enzymatic DNA molecule. If desired, several different second enzymatic DNA molecules can be placed in the same cell or carrier to produce different deoxyribozymes.

Methods of isolating and purifying enzymatic DNA molecules of the present invention are also contemplated. In addition to the methods described herein, various purification methods (e.g. those using HPLC) and chromatographic isolation techniques are available in the art. See, e.g., the methods described in published international application no. WO 93/23569, the disclosures of which are incorporated herein by reference.

It should also be understood that various combinations of the embodiments described herein are included within the scope of the present invention. Other features and advantages of the present invention will be apparent from the descriptions hereinabove, from the Examples to follow, and from the claims.

EXAMPLES

The following examples illustrate, but do not limit, the present invention.

Example 1

In Vitro Evolution of Enzymatic DNA Molecules: An Overview

In vitro selection and in vitro evolution techniques allow new catalysts to be isolated without a priori knowledge of their composition or structure. Such methods have been used to obtain RNA enzymes with novel catalytic properties. For example, ribozymes that undergo autolytic cleavage with lead cation have been derived from a randomized pool of tRNA$^{Phe}$ molecules (Pan and Uhlenbeck, *Biochemistry* 31: 3887–3895 (1992)). Group I ribozyme variants have been isolated that can cleave DNA (Beaudry and Joyce, *Science* 257: 635–641 (1992)) or that have altered metal dependence (Lehman and Joyce, *Nature* 361: 182–185 (1993)). Starting with a pool of random RNA sequences, molecules have been obtained that catalyze a polymerase-like reaction (Bartel and Szostak, *Science* 261: 1411–14–18 (1993)). In the present example, refinement of specific catalytic properties of an evolved enzyme via alteration of the selection constraints during an in vitro evolution procedure is described.

Darwinian evolution requires the repeated operation of three processes: (a) introduction of genetic variation; (b) selection of individuals on the basis of some fitness criterion; and (c) amplification of the selected individuals. Each of these processes can be realized in vitro (Joyce, *Gene* 82: 83 (1989)). A gene can be mutagenized by chemical modification, incorporation of randomized mutagenic oligodeoxynucleotides, or inaccurate copying by a polymerase. (See, e.g., Cadwell and Joyce, in *PCR Methods and Applications* 2: 28–33 (1992); Cadwell and Joyce, *PCR Methods and Applications* 3 (*Suppl.*): S136–S140 (1994); Chu, et al., *Virology* 98: 168 (1979); Shortle, et al., *Meth. Enzymol.* 100: 457 (1983); Myers, et al., *Science* 229: 242 (1985); Matteucci, et al., *Nucleic Acids Res.* 11: 3113 (1983); Wells, et al., *Gene* 34: 315 (1985); McNeil, et al., *Mol. Cell. Biol.* 5: 3545 (1985); Hutchison, et al., *PNAS USA* 83: 710 (1986); Derbyshire, et al., *Gene* 46: 145 (1986); Zakour, et al., *Nature* 295: 708 (1982); Lehtovaara, et al., *Protein Eng.* 2: 63 (1988); Leung, et al., *Technique* 1: 11 (1989); Zhou, et al., *Nucl. Acids Res.* 19: 6052 (1991).)

The gene product can be selected, for example, by its ability to bind a ligand or to carry out a chemical reaction. (See, e.g., Joyce, *Id.* (1989); Robertson and Joyce, *Nature* 344: 467 (1990); Tuerk, et al., *Science* 249: 505 (1990).) The gene that corresponds to the selected gene product can be amplified by a reciprocal primer method, such as the polymerase chain reaction (PCR). (See, e.g., Saiki, et al., *Science* 230: 1350–54 (1985); Saiki, et al., *Science* 239: 487–491 (1988).)

Alternatively, nucleic acid amplification may be carried out using self-sustained sequence replication (3SR). (See, e.g., Guatelli, et al., *PNAS USA* 87: 1874 (1990), the disclosures of which are incorporated by reference herein.) According to the 3SR method, target nucleic acid sequences may be amplified (replicated) exponentially in vitro under isothermal conditions by using three enzymatic activities essential to retroviral replication: (1) reverse transcriptase, (2) RNase H, and (3) a DNA-dependent RNA polymerase. By mimicking the retroviral strategy of RNA replication by means of cDNA intermediates, this reaction accumulates c(DNA and RNA copies of the original target.

In summary, if one is contemplating the evolution of a population of enzymatic DNA molecules, a continuous series of reverse transcription and transcription reactions replicates an RNA target sequence by means of CDNA intermediates. The crucial elements of this design are (a) the oligonucleotide primers both specify the target and contain 5' extensions encoding the T7 RNA polymerase binding site, so that the resultant cDNAs are competent transcription templates; (b) CDNA synthesis can proceed to completion of both strands due to the degradation of template RNA in the intermediate RNA-DNA hybrid by RNase H; and (c) the reaction products (CDNA and RNA) can function as templates for subsequent steps, enabling exponential replication.

If one is evolving enzymatic DNA molecules, various critical elements of this design are somewhat different, as disclosed in these Examples. For instance, (1) the oligonucleotide primers specify the target and are preferably "marked" or labeled in some fashion—e.g., via biotinylation—so the resultant competent template strands are easily identified; and (2) the in vitro selection procedure used preferably depends upon the identification of the most favorable release mechanism.

A major obstacle to realizing Darwinian evolution in vitro is the need to integrate mutation and amplification, both of which are genotype-related, with selection, which is phenotype-related. In the case of nucleic acid enzymes, for which genotype and phenotype are embodied in the same molecule, the task is simplified.

A. Design of Enzymatic DNA Molecules

It is well known that single-stranded DNA can assume interesting tertiary structures. The structure of a "tDNA", for example, closely resembles that of the corresponding tRNA. (See Paquette, et al., *Eur. J. Biochem.* 189: 259–265 (1990).) Furthermore, it has been possible to replace as many as 31 of 35 ribonucleotides within a hammerhead ribozyme, while retaining at least some catalytic activity. (See Perreault, et al., *Nature* 344: 565–567 (1990); Williams, et al., *Proc. Natl. Acad. Sci. USA* 89: 918–921 (1992); Yang, et al., *Biochemistry* 31: 5005–5009 (1992).

In vitro selection techniques have been applied to large populations of random-sequence DNAs, leading to the recovery of specific DNA "aptamers" that bind a target ligand with high affinity (Bock, et al., *Nature* 355: 564–566 (1992); Ellington & Szostak, *Nature* 355: 850–852 (1992); Wyatt & Ecker, *PNAS USA* 91: 1356–1360 (1994)). Recently, two groups can-ed out the first NMR structural determination of an aptamer, a 15 mer DNA that forms a G-quartet structure and binds the protein thrombin with high affinity (Wang, et al., *Biochemistry* 32: 1899–1904 (1993); Macaya, et al., *PNAS USA* 90: 3745–3749 (1993)). These findings were corroborated by an X-ray crystallographic analysis (Padmanabhan, et al., *J. Biol. Chem.* 268: 17651–17654 (1993)).

The ability to bind a substrate molecule with high affinity and specificity is a prerequisite of a good enzyme. In addition, an enzyme must make use of well-positioned functional groups, either within itself or a cofactor, to promote a particular chemical transformation. Furthermore, the enzyme must remain unchanged over the course of the reaction and be capable of operating with catalytic turnover. Some would add the requirement that it be an informational macromolecule, comprised of subunits whose specific ordering is responsible for catalytic activity. While these criteria are open to debate on both semantic and chemical grounds, they serve to distinguish phenomena of chemical rate enhancement that range from simple solvent effects to biological enzymes operating at the limit of substrate diffusion (Albery & Knowles, Biochemistry 15: 5631–5640 (1976)).

As described in greater detail hereinbelow, we sought to develop a general method for rapidly obtaining DNA catalysts and DNA enzymes, starting from random sequences. As an initial target, we chose a reaction that we felt was well within the capability of DNA: the hydrolytic cleavage of an RNA phosphodiester, assisted by a divalent metal cofactor. This is the same reaction that is carried out by a variety of naturally-occurring RNA enzymes, including the hammerhead and hairpin motifs. (See, e.g., Forster A. C. & Symons R. H., Cell 49: 2:11–220 (1987); Uhlenbeck, Nature 328: 596–600 (1987); Hampel & Tritz, Biochemistry 28: 4929–4933 (1989)).

It has recently been shown that, beginning with a randomized library of tRNA molecules, one can obtain ribozymes that have $Pb^{2+}$-dependent, site-specific RNA phosphoesterase activity at neutral pH (Pan & Uhlenbeck, Biochemistry 31: 3887–3895 (1992); Pan & Uhlenbeck, Nature 358: 560–563 (19)92)). This is analogous to the fortuitous self-cleavage reaction of yeast tRNA$^{Phe}$ (Dirheimer & Werner, Biochimie 54: 127–144 (1972)), which depends on specific coordination of a $Pb^{2+}$ ion at a defined site within the tRNA. (See Rubin & Sundaralingam, J. Biomol. Struct. Dyn. 1: 639–646 (1983); Brown, et al., Biochemistry 24: 4785–4801 (1985).)

As disclosed herein, our goals included the development of DNAs that could carry out $Pb^{2+}$-dependent cleavage of a particular RNA phosphoester, initially presented within a short leader sequence attached to the 5' end of the DNA, and ultimately located within a separate molecule that could be cleaved in an intermolecular fashion with rapid catalytic turnover. These goals were successfully achieved, as described further below.

No assumptions were made as to how the DNA would interact with the target phosphoester and surrounding nucleotides. Beginning with a pool of approximately $10^{14}$ random 50 mer sequences, in vitro selection was allowed to run its course. After five rounds of selection carried out over four days, the population as a whole had attained the ability to cleave the target phosphoester in the presence of 1 mM $Pb^{2+}$ at a rate of about 0.2 $min^{-1}$. This is an approximately $10^5$-fold increase compared to the spontaneous rate of cleavage under the same reaction conditions.

Individuals were isolated from the population, sequenced, and assayed for catalytic activity. Based on this information, the reaction was converted to an intermolecular format and then simplified to allow site-specific cleavage of a 19 mer substrate by a 38 mer DNA enzyme, in a reaction that proceeds with a turnover rate of 1 $min^{-1}$ at 23° C. and pH 7.0 in the presence of 1 mM 13bOAc.

B. In Vitro Selection Scheme

A starting pool of approximately $10^{14}$ single-stranded DNA molecules was generated, all of which contain a 5' biotin moiety, followed successively by a fixed domain that includes a single ribonucleotide, a potential catalytic domain comprised of 50 random deoxyribonucleotides, and a second fixed domain that lay at the 3' terminus (FIG. 1).

The pool was constructed by a nested PCR (polymerase chain reaction) technique, beginning with synthetic DNA that contained 50 random nucleotides flanked by primer binding sites. The nested PCR primer was a 5'-biotinylated synthetic oligodeoxynucleotide with a 3'-terminal adenosine ribonucleotide. Ribonucleotide-terminated oligonucleotides efficiently prime template-directed elongation in the context of the PCR (L. E. Orgel, personal communication), in this case giving rise to an extension product that contains a single embedded ribonucleotide.

FIG. 1 illustrates a selective amplification scheme for isolation of DNAs that cleave a target RNA phosphoester. Double-stranded DNA containing a stretch of 50 random nucleotides is amplified via PCR, employing a 5'-biotinylated DNA primer (e.g., primer 3-3a or 3b) terminated at the 3' end by an adenosine ribonucleotide (represented by the symbol "N" or "rA", wherein both N and rA represent an adenosine ribonucleotide). This primer is extended by Taq polymerase to yield a DNA product that contains a single embedded ribonucleotide. The resulting double-stranded DNA is immobilized on a streptavidin matrix and the unbiotinylated DNA strand is removed by washing with 0.2 N NaOH. After re-equilibrating the column with a buffered solution, the column is washed with the same solution with added 1 mM PbOAc. DNAs that undergo $Pb^{2+}$-dependent self-cleavage are released from the column, collected in the eluant, and amplified by PCR. The PCR products are then used to initiate the next round of selective amplification.

The PCR products were passed over a streptavidin affinity matrix, resulting in noncovalent attachment of the 5'-biotinylated strand of the duplex DNA. The nonbiotinylated strand was removed by brief washing with 0.2 N NaOH, and the bound strand was equilibrated in a buffer containing 0.5 M NaCl, 0.5 M KCl, 50 mM $MgCl_2$, and 50 mM HEPES (pH 7.0) at 23° C. Next, 1 mM PbOAc was provided in the same buffer, allowing $Pb^{2+}$-dependent cleavage to occur at the target phosphoester, thereby releasing a subset of the DNAs from the streptavidin matrix. In principle, an individual DNA might facilitate its own release by various means, such as disruption of the interaction between biotin and streptavidin or cleavage of one of the deoxyribonucleotide linkages. It was felt that cleavage of the ribonucleoside 3'-O—P bond would be the most likely mechanism for release, based on the relative lability of this linkage, and that $Pb^{2+}$-dependent hydrolytic cleavage would allow release to occur most rapidly. In principle, however, the in vitro selection procedure should identify the most favorable release mechanism as well as those individuals best able to carry out that mechanism.

DNA molecules released from the matrix upon addition of $Pb^{2+}$ were collected in the eluant, concentrated by precipitation with ethanol, and subjected to nested PCR amplification. As in the construction of the starting pool of molecules, the first PCR amplification utilized primers that flank the random region (primers 1 and 2) and the second utilized a 5'-biotinylated primer (primer 3b) that has a 3'-terminal riboadenylate, thereby reintroducing the target RNA phosphoester. The entire selective amplification procedure requires 3–4 hours to perform.

The molecules are purified in three ways during each round of this procedure: first, following PCR amplification, by extracting twice with phenol and once with chloroform/ isoamyl alcohol, then precipitating with ethanol; second, following attachment of the DNA to streptavidin, by washing away all the nonbiotinylated molecules under strongly denaturing conditions; and third, following elution with $Pb^{2+}$, by precipitating with ethanol. There is no gel electrophoresis purification step, and thus no selection pressure constraining the molecules to a particular length.

C. Selection of Catalytic DNA

We carried out five successive rounds of in vitro selection, progressively decreasing the reaction time following addition of $Pb^{2+}$ in order to progressively increase the stringency of selection. During rounds 1 though 3, the reaction time was 1 hour; during round 4, it was 20 minutes; and during round 5, it was 1 minute. The starting pool of single-stranded DNAs, together with the population of molecules obtained after each round of selection, was assayed for self-cleavage activity under conditions identical to those employed during in vitro selection.

For this assay, the molecules were prepared with a $5'$-$^{32}P$ rather than a 5'-biotin moiety, allowing detection of both the starting material and the 5' cleavage product. Following a 5-minute incubation, there was no detectable activity in the initial pool (G0) or in the population obtained after the first and second rounds of selection. DNAs obtained after the third round (G3) exhibited a modest level of activity and this activity increased steadily, reaching approximately 50% self-cleavage for the DNAs obtained after the fifth round of selection (G5). Cleavage was detected only at the target phosphoester, even after long incubation times. This activity was lost if $Pb^{2+}$ was omitted from the reaction mixture. Reaction mixtures contained 50 mM $MgCl_2$, 0.5 M NaCl, 0.5 M KCl, 50 mM HEPES (pH 7.0 at 23° C.), and 3 nM [5'-$^{32}P$]-labeled DNA, incubated at 23° C. for 5 min in either the presence or absence of 1 mM PbOAc.

The 28-nucleotide 5' cleavage product (Clv) preferably has the sequence 5'-GGGACGAATTCTAATACGACTCACTATN-3' (SEQ ID NO 5), wherein "N" represents adenosine ribonucleotide with an additional 2', 3'-cyclic phosphate on the 3' end (SEQ ID NO 5). In alternative embodiments, "N" represents adenosine ribonucleotide with an additional 2' or 3' phosphate on the 3' end of the molecule.

Any given "Pre" sampling will contain a wide variety of precursor DNAs, and each sampling will likely differ from previous and subsequent samplings. The "G1" through "G5" lanes contain "Pre" bands that are increasingly enriched for catalytic DNA molecules, but still contain a large number of different DNA sequences (i.e., differing in the 50 nucleotide randomized domain). A sample of these different sequences from "G5 Pre" DNA is provided in FIG. 2.

Figure 3:
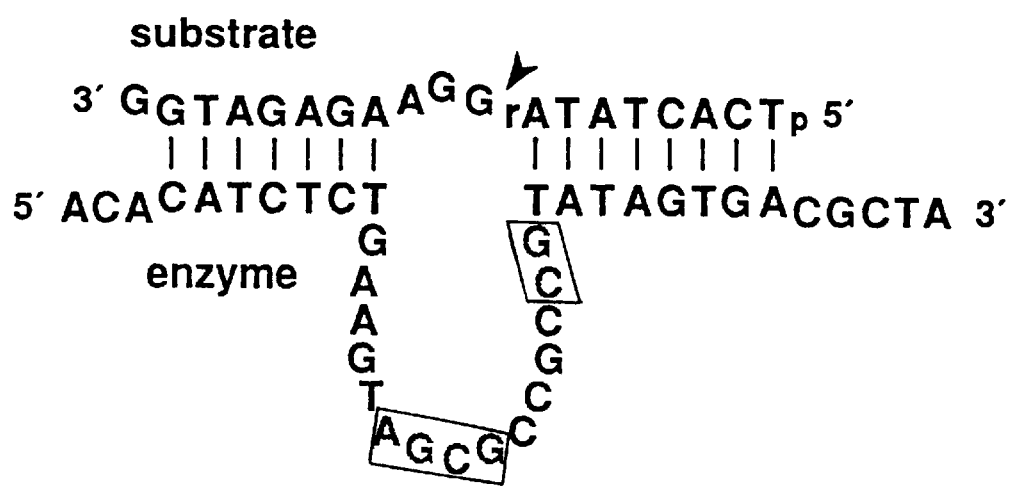
FIG. 3 is a diagrammatic representation of the complex formed between the 19 mer substrate (5'-TCACTATrAGGAAGAGATGG-3', SEQ ID NO 2) and 38 mer DNA enzyme (5'-ACACATCTCTGAAGTAGCGCC GCCGTATAGTGACGCTA-3', SEQ ID NO 3). The substrate contains a single adenosine ribonucleotide ("rA", adjacent to the arrow), flanked by deoxyribonucleotides. The synthetic DNA enzyme is a 38-nucleotide portion of the most frequently occurring variant shown in FIG. 2. Highly-conserved nucleotides located within the putative catalytic domain are "boxed". As illustrated, one conserved sequence is "AGCG", while another is "CG" (reading in the 5'→3' direction).

Shotgun cloning techniques were employed to isolate individuals from the G5 population; the complete nucleotide sequences of 20 of these subclones were then determined (see FIG. 3). (Also see, e.g., Cadwell and Joyce, in *PCR Methods and Applications* 2: 28–33 (1992); Cadwell and Joyce, *PCR Methods and Applications* 3 (*Suppl.*): S136–S140 (1994).) Of the 20 sequences, five were unique, two occurred twice, one occurred three times, and one occurred eight times. All of the individual variants share common sequence elements within the 50-nucleotide region that had been randomized in the starting pool of DNA. They all contain two presumed template regions, one with complementarity to a stretch of nucleotides that lies just upstream from the cleavage site and the other with complementarity to nucleotides that lie at least four nucleotides downstream. Between these two presumed template regions lies a variable domain of 1–11 nucleotides, followed by the fixed sequence 5'-AGCG-3', then a second variable domain of 3–8 nucleotides, and finally the fixed sequence 5'-CG-3' or 5'-CGA-3'. Nucleotides that lie outside of the two presumed template regions are highly variable in both sequence and length. In all of the sequenced subclones, the region corresponding to the 50 initially-randomized nucleotides remains a total of 50 nucleotides in length.

Figures 1, 5:
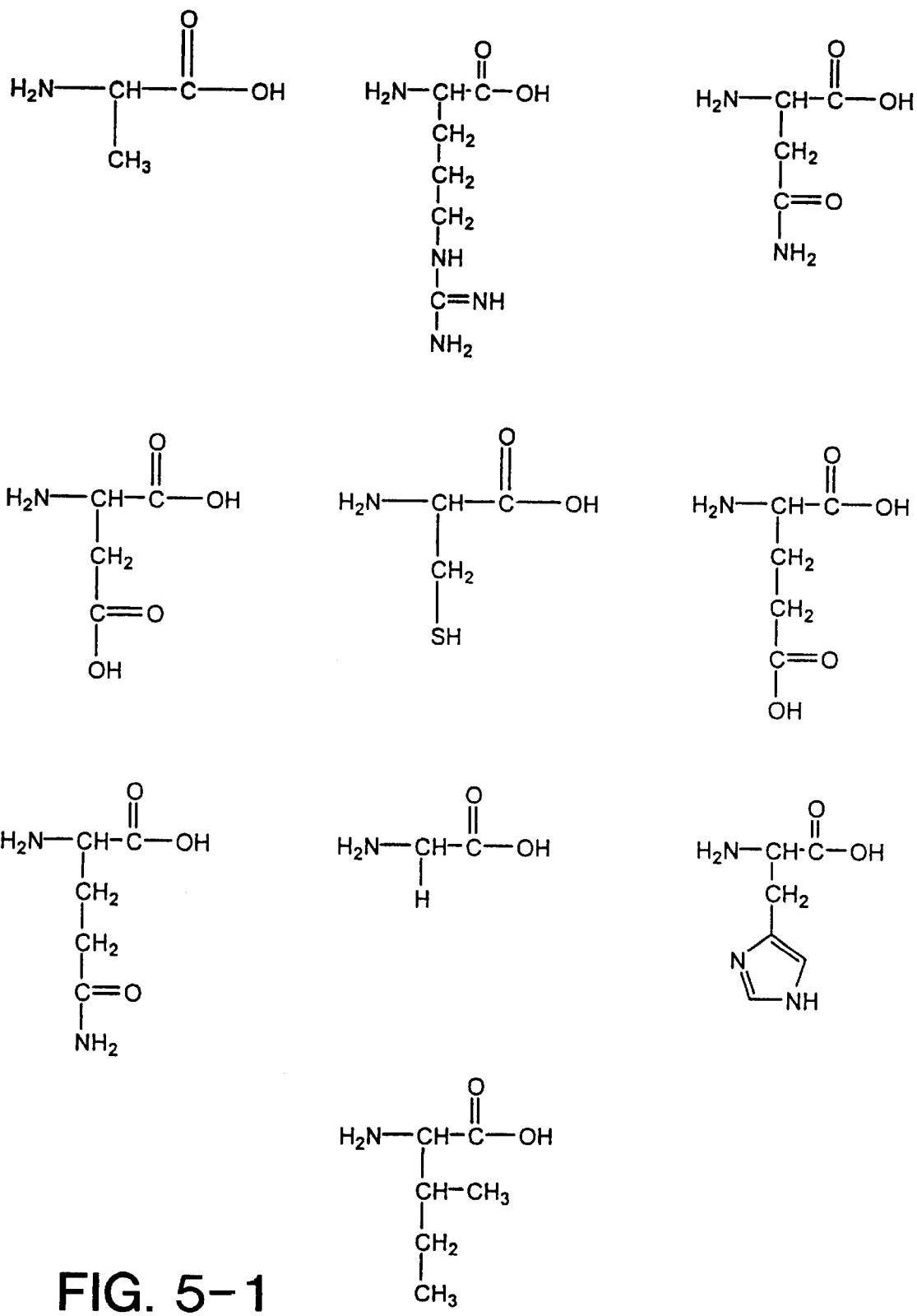
Figures 2, 5:
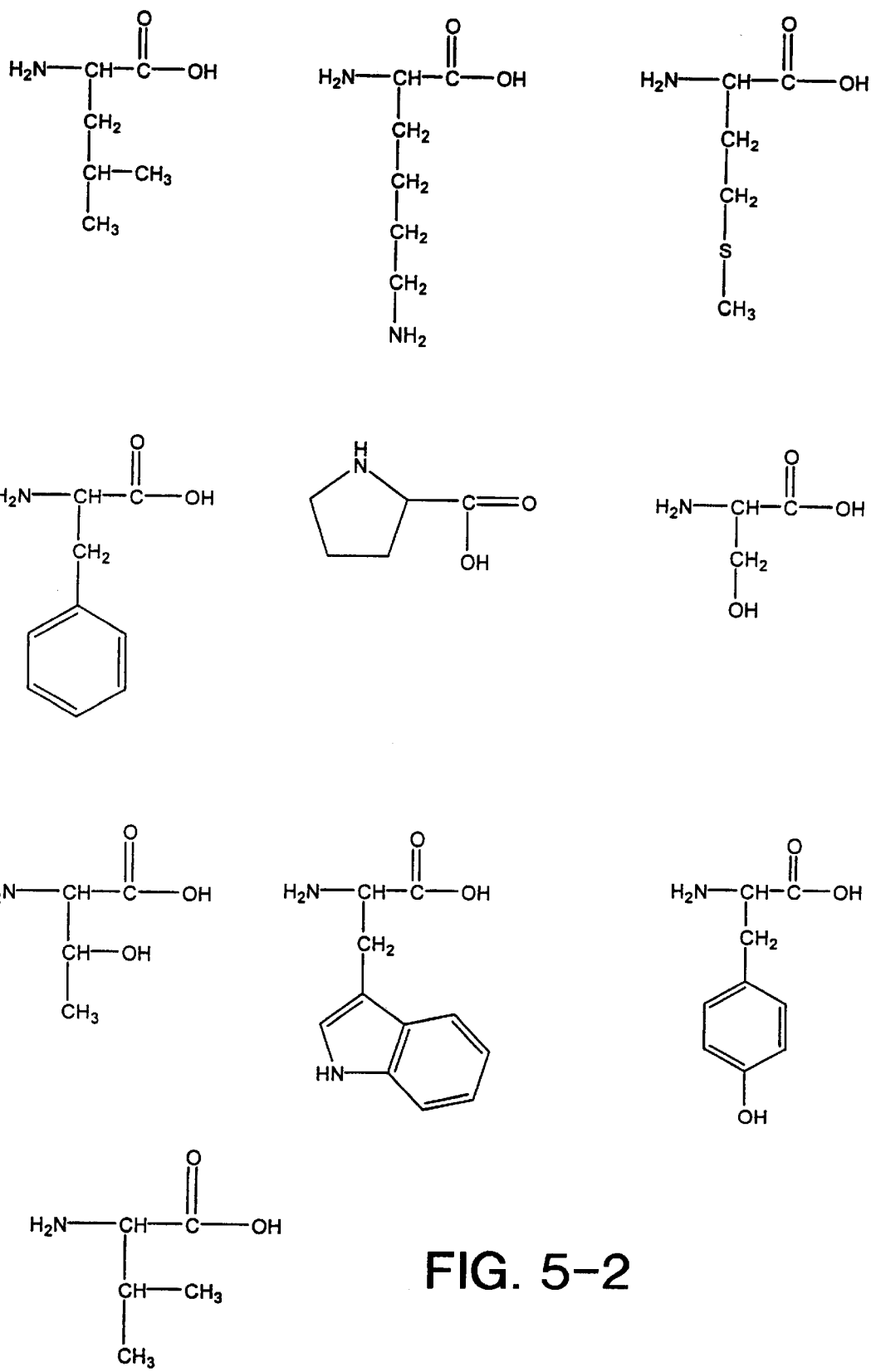

FIG. 2 illustrates the sequence alignment of individual variants isolated from the population after five rounds of selection. The fixed substrate domain (5'-GGGACGAATTCTAATACGACTCACTATrAGGAAGA GATGGCGAC-3', or 5'-GGGACGAATTCTAATA CGACTCACTATNGGAAGAGATGGCGAC-3', where N represents adenosine ribonucleotide) (SEQ ID NO 13) is shown at the top, with the target riboadenylate identified with an inverted triangle. Substrate nucleotides that are commonly involved in presumed base-pairing interactions are indicated by a vertical bar. Sequences corresponding to the 50 initially-randomized nucleotides are aligned antiparallel to the substrate domain. All of the variants are 3'-terminated by the fixed sequence 5'-CGGTAAGCTTGGCAC-3' (SEQ ID NO 1) ("primer site"; not shown). Nucleotides within the initially-randomized region that are presumed to form base pairs with the substrate domain are indicated on the right and left sides of the Figure; the putative base-pair-forming (or substrate binding) regions of the enzymatic DNA molecules are individually boxed in each sequence shown. The highly-conserved nucleotides within the putative catalytic domain are illustrated in the two boxed columns.

While it is anticipated that additional data will be helpful in constructing a meaningful secondary structural model of the catalytic domain, we note that, like the hammerhead and hairpin ribozymes, the catalytic domain of our enzymatic DNA molecules appears to contain a conserved core flanked by two substrate binding regions (or recognition domains) that interact with the substrate through base-pairing interactions. Similar to the hammerhead and hairpin ribozymes, the catalytic DNAs also appear to require a short stretch of unpaired substrate nucleotides—in this case 5'-GGA-3'—between the two regions that are involved in base pairing.

It was also interesting to note that each of the nine distinct variants exhibited a different pattern of presumed complementarity with the substrate domain. In some cases, base pairing was contiguous, while in others it was interrupted by one or more noncomplementary pairs. The general tendency seems to be to form tighter interaction with the nucleotides that lie upstream from the cleavage site compared to those that lie downstream. Binding studies and site-directed mutagenesis analysis should enable us to gain further insights and to further substantiate this conjecture.

In order to gain further insight into the sequence requirements for catalytic function, the self-cleavage activity of six of the nine variants was tested and evaluated under the within-described selection conditions. Not surprisingly, the sequence that occurred in eight of the 20 subclones proved to be the most reactive, with a first-order rate constant of 1.4 $min^{-1}$. All of the studied variants were active in the self-cleavage assay and all gave rise to a single 5'-labeled product corresponding to cleavage at the target RNA phosphoester.

The dominant subclone was further analyzed under a variety of reaction conditions. Its self-cleavage activity was dependent on $Pb^{2+}$ but was unaffected if $Mg^{2+}$ was omitted from the reaction mixture. There was a requirement for a monovalent cation as well, which can be met by either $Na^+$ or $K^+$. The reaction rate increased linearly with increasing concentration of monovalent cation over the range of 0–1.0 M (r=0.998). Other variables that might affect the reaction, such as pH, temperature, and the presence of other divalent metals, are in the process of being evaluated.

Example 2

Materials and Methods

A. Oligonucleotides and Oligonucleotide Analogues

Synthetic DNAs and DNA analogues were purchased from Operon Technologies. The 19-nucleotide substrate, 5'-pTCACTATrAGGAAGAGATGG-3' (SEQ ID NO 2) (or 5'-pTCACTATNGGAAGAGATGG-3' (SEQ ID NO 7), wherein "N" represents adenosine ribonucleotide) (SEQ ID NO 7), was prepared by reverse-transcriptase catalyzed extension of 5'-pTCACTATrA-3' (or 5'-pTCACTATN-3', wherein "N" represents adenosine ribonucleotide), as previously described (Breaker, Banerji, & Joyce, *Biochemistry* 33: 11980–11986 (1994)), using the template 5'-CCATCTCTTCCTATAGTGAGTCCGGCTGCA-3' (SEQ ID NO 9). Primer 3, 5'-GGGACGAATTCTAATACGACTCACTATrA-3' (SEQ ID NO 6) (or 5'-GGGACGAATTCTAATACGACTCACTATN-3' (SEQ ID NO 5), wherein "N" represents adenosine ribonucleotide) (SEQ ID NO 6), was either 5'-labeled with [γ-$^{32}$P]ATP and T4 polynucleotide kinase (primer 3a) or 5'-thiophosphorylated with [γ-S]ATP and T4 polynucleotide kinase and subsequently biotinylated with N-iodoacetyl-N'-biotinylhexylenediamine (primer 3b).

B. DNA Pool Preparation

The starting pool of DNA was prepared by PCR using the synthetic oligomer 5'-GTGCCAAGCTTACCG-X$_{50}$-GTCGCCATCTCrTCC-3' (SEQ ID NO 4), where X is an equimolar mixture of G, A, T and C. A 2-ml PCR, containing 500 pmoles of the randomized oligomer, 1,000 pmoles primer 1 (5'-GTGCCAAGCTTACCG-3', SEQ ID NO 10), 500 pmoles primer 2 (5'-CTGCAGAATTCTAATACGACT CACTATAGGAAGAGATGGCGAC-3', SEQ ID NO 11), 500 pmoles primer 3b, 10 μCi [α-$^{32}$P]dATP, and 0.2 U μl$^{-1}$ Taq DNA polymerase, was incubated in the presence of 50 mM KCl, 1.5 mM $MgCl_2$, 10 mM Tris-HCl (pH 8.3 at 23° C.), 0.01% gelatin, and 0.2 mM of each dNTP for 1 min at 92° C., 1 min at 50° C., and 2 min at 72° C., then 5 cycles of 1 min at 92° C., 1 min at 50° C., and 1 min at 72° C. The resulting mixture was extracted twice with phenol and once with chloroform/isoamyl alcohol, and the DNA was isolated by precipitation with ethanol.

C. In Vitro Selection

The starting pool of DNA was resuspended in 500 μL of buffer A (1 M NaCl and 50 mM HEPES (pH 7.0 at 23° C.)) and was passed repeatedly over a streptavidin column (AffiniTip Strep 20, Genosys, The Woodlands, Tex.). The column was washed with five 100 μl volumes of buffer A, followed by five 100 μl volumes of 0.2 N NaOH, then equilibrated with five 100 μl volumes of buffer B (0.5 M NaCl, 0.5 M KCl, 50 mM $MgCl_2$, and 50 mM HEPES (pH 7.0 at 23° C.)). The immobilized single-stranded DNA was eluted over the course ol 1 hr with three 20 μl volumes of buffer B with added 1 mM PbOAc. The entire immobilization and elution process was conducted at 23° C. The eluant was collected in an equal volume of buffer C (50 mM HEPES (pH 7.0 at 23° C.) and 80 mM EDTA) and the DNA was precipitated with ethanol.

The resulting DNA was amplified in a 100 μL PCR containing 20 pmoles primer 1, 20 pmoles primer 2, 0.05 U μl$^{-1}$ Taq polymerase, 50 mM KCl, 1.5 mM $MgCl_2$, 10 mM Tris-HCl (pH 8.3 at 23° C.), 0.01% gelatin, and 0.2 mM of each dNTP for 30 cycles of 10 sec at 92° C., 30 sec at 50° C., and 30 sec at 72° C. The reaction products were extracted twice with phenol and once with chloroform/isoamyl alcohol, and the DNA was recovered by precipitation with ethanol. Approximately 4 pmoles of the amplified DNA was added to a second, nested PCR containing 100 pmoles primer 1, 100 pmoles primer 3b, 20 μCi [α-$^{32}$P]dATP, and 0.1 U μl$^{-1}$ Taq polymerase, in a total volume of 200 μL that was amplified for 10 cycles of 1 min at 92° C., 1 min at 50° C., and 1 min at 72° C. The PCR products were once more extracted and precipitated, and the resulting DNA was resuspended in 50/L buffer A, then used to begin the next round of selection.

The second and third rounds were carried out as above, except that the nested PCR at the end of the third round was performed in a 100 μl volume. During the fourth round, the elution time following addition of $Pb^{2+}$ was reduced to 20 min (two 20 μL elution volumes) and only half of the recovered DNA was used in the first PCR, which involved only 15 temperature cycles. During the fifth round, the elution time was reduced to 1 min (two 20 μL elution volumes) and only one-fourth of the recovered DNA was used in the first PCR, which involved 15 temperature cycles. DNA obtained after the fifth round of selection was subcloned and sequenced, as described previously (Tsang & Joyce, *Biochemistry* 33: 5966–5973 (1994)).

D. Kinetic Analysis of Catalytic DNAs

Populations of DNA and various subcloned individuals were prepared with a 5'-$^{32}$P label by asymmetric PCR in a 25 μl reaction mixture containing 10 pmoles primer 3a, 0.5 pmoles input DNA, and 0.1 U μl$^{-1}$ Taq polymerase, under conditions as described above, for 10 cycles of 1 min at 92° C., 1 min at 50° C., and 1 min at 72° C. The resulting [5'-$^{32}$P]-labeled amplification products were purified by electrophoresis in a 10% polyacrylamide/8 M gel.

Self-cleavage assays were carried out following preincubation of the DNA in buffer B for 10 min. Reactions were initiated by addition of PbOAc to 1 mM final concentration and were terminated by addition of an equal volume of buffer C. Reaction products were separated by electrophoresis in a 10% polyacrylamide/8 M gel. Kinetic assays under multiple-turnover conditions were carried out in buffer B that included 50 μg ml$^{-1}$ BSA to prevent adherence of material to the vessel walls. Substrate and enzyme molecules were preincubated separately for 5 min in reaction buffer that lacked $Pb^{2+}$, then combined, and the reaction was initiated by addition of PbOAc to a final concentration of 1 mM.

Example 3

Evolution of Deoxyribozymes That Cleave Intermolecularly

A. Conversion to an Intermolecular Format

Based on the variable pattern of presumed base-pairing interactions between the catalytic and substrate domains of the studied variants, it was felt that it would be reasonably straightforward to convert the DNA-catalyzed reaction to an intermolecular format. In doing so, we wished to simplify the two substrate-binding regions of the catalyst so that each would form an uninterrupted stretch of 7–8 base pairs with the substrate. In addition, we wished to provide a mini mal substrate, limited to the two base-pairing regions and the intervening sequence 5'-GGA-3' (FIG. 3).

FIG. 3 is a diagrammatic representation of the complex formed between the 19 mer substrate and 38 mer DNA enzyme. The substrate contains a single adenosine ribonucleotide ("rA" or "N", adjacent to the arrow), flanked by deoxyribonucleotides. The synthetic DNA enzyme is a 38-nucleotide portion of the most frequently occurring variant shown in FIG. 2. Highly-conserved nucleotides located within the putative catalytic domain are "boxed". As illustrated, one conserved sequence is "AGCG", while another is "CG" (reading in the 5'→3' direction). Initial rates of cleavage were determined for reactions involving 5 nM DNA enzyme and either 0.125, 0.5, 1, 2, or 4 µM substrate.

In designing the catalytic domain, we relied heavily on the composition of the most reactive variant, truncating by two nucleotides at the 5' end and 11 nucleotides at the 3' end. The 15 nucleotides that lay between the two template regions were left unchanged and a single nucleotide was inserted into the 3' template region to form a continuous stretch of nucleotides capable of forming base pairs with the substrate. The substrate was simplified to the sequence 5'-TCACTATrA•GGAAGAGATGG-3' (or 5'-TCACTATN•GGAAGAGATGG-3', (SEQ ID NO: 12) wherein "N" represents adenosine ribonucleotide) (SEQ ID NO 12), where the underlined nucleotides correspond to the two regions involved in base pairing with the catalytic DNA molecule.

The simplified reaction system, employing a 38 mer catalytic DNA molecule (catalyst) comprised entirely of deoxyribonucleotides and a 19 mer substrate containing a single ribonucleotide embedded within an otherwise all-DNA sequence, allows efficient DNA-catalyzed phosphoester cleavage with rapid turnover. Over a 90-minute incubation in the presence of 0.01 µM catalyst and 1 µM substrate, 46% of the substrate is cleaved, corresponding to 46 turnovers of the catalyst. A preliminary kinetic analysis of this reaction was carried out, evaluated under multiple-turnover conditions. The DNA catalyst exhibits Michaelis-Menten kinetics, with values for $k_{cat}$ and $K_m$ of 1 min$^{-1}$ and 2 µM, respectively. The value for $K_m$ is considerably greater than the expected dissociation constant between catalyst and substrate based on Watson-Crick interactions. The substrate was incubated under identical reaction conditions (but in the absence of the catalyst); a value for $k_{uncat}$ of $4^{X}10^{-6}$ min$^{-1}$ was obtained. This is consistent with the reported value of $5^{X}10^{-3}$ min$^{-1}$ for hydrolysis of the more labile 1-nitrophenyl-1,2-propanediol in the presence of 0.5 mM $Pb^{2+}$ at pH 7.0 and 37° C. (Breslow & Huang, *PNAS USA* 88: 4080–4083 (1991)).

It is now presumed that the phosphoester cleavage reaction proceeds via a hydrolytic mechanism involving attack by the ribonucleoside 2'-hydroxyl on the vicinal phosphate, generating a 5' product with a terminal 2' (3')-cyclic phosphate and 3' product with a terminal 5'-hydroxyl. In support of this mechanism, the 3'-cleavage product is efficiently phosphorylated with T4 polynucleotide kinase and [γ-$^{32}$P] ATP, consistent with the availability of a free 5'-hydroxyl.

B. Discussion

After five rounds of in vitro selection, a population of single-stranded DNA molecules that catalyze efficient $Pb^{2+}$-dependent cleavage of a target RNA phosphoester was obtained. Based on the common features of representative individuals isolated from this population, a simplified version of both the catalytic and substrate domains was constructed, leading to a demonstration of rapid catalytic turnover in an intermolecular context. Thus the 38 mer catalytic domain provides an example of a DNA enzyme, or what might be termed a "deoxyribozyme".

Referring to this molecule as an enzyme, based on the fact that it is an informational macromolecule capable of accelerating a chemical transformation in a reaction that proceeds with rapid turnover and obeys Michaelis-Menten kinetics, may not satisfy everyone's notion of what constitutes an enzyme. Some might insist that an enzyme, by definition, must be a polypeptide. If, however, one accepts the notion of an RNA enzyme, then it seems reasonable to adopt a similar view concerning DNA enzymes. Considering how quickly we were able to generate this molecule from a pool of random-sequence DNAs, we expect that many other examples of synthetic DNA enzymes will appear in the near future.

The $Pb^{2+}$-dependent cleavage of an RNA phosphoester was chosen as an initial target for DNA catalysis because it is a straightforward reaction that simply requires the proper positioning of a coordinated $Pb^{2+}$-hydroxyl to facilitate deprotonation of the 2' hydroxyl that lies adjacent to the cleavage site. (See, e.g., Pan, et al., in *The RNA World*, Gesteland & Atkins (eds.), pp. 271–302, Cord Spring Harbor Laboratory Press, Cold Spring Harbor, N.Y. (1993).) $Pb^{2+}$ is known to coordinate to the N7 position of purines, the O6 position of guanine, the O4 position of uracil, and the N3 position of cytosine (Brown, et al., *Nature* 303: 543–546 (1993)). Thus, the differences in sugar composition and conformation of DNA compared to RNA seemed unlikely to prevent DNA from forming a well-defined $Pb^{2+}$-binding pocket.

A substrate that contains a single ribonucleotide within an otherwise all-DNA sequence was chosen because it provided a uniquely favored site for cleavage and insured that any resulting catalytic activity would be attributable solely to DNA. Substrate recognition appears to depend on two regions of base-pairing interactions between the catalyst and substrate. However, the unpaired substrate nucleotides, 5'-GGA-3', that lie between these two regions may play an important role in substrate recognition, metal coordination, or other aspects of catalytic function.

It is further anticipated that an all-RNA molecule, other RNA-DNA composites, and molecules containing one or more nucleotide analogs may be acceptable substrates. As disclosed herein, the within-described in vitro evolution procedures may successfully be used to generate enzymatic DNA molecules having the desired specificities; further analyses along these lines are presently underway.

In addition, studies to determine whether the presumed base-pairing interactions between enzyme and substrate are generalizable with respect to sequence are in progress, using the presently-described methods. The within-disclosed $Pb^{2+}$-dependent deoxyribozymes may also be considered model compounds for exploring the structural and enzymatic properties of DNA.

The methods employed in the present disclosure for the rapid development of DNA catalysts will have considerable generality, allowing us to utilize other cofactors to trigger the cleavage of a target linkage attached to a potential catalytic domain. In this regard, the development of $Mg^{2+}$-dependent DNA enzymes that specifically cleave target RNAs under physiological conditions is of interest. Such a molecule will provide an alternative to traditional antisense and ribozyme approaches for the specific inactivation of target mRNAs.

DNA thus joins RNA and protein on the list of biological macromolecules that are capable of exhibiting enzymatic activity. The full extent of DNA's catalytic abilities remains to be explored, but these explorations should proceed rapidly based on in vitro selection methods such as those employed in this study.

DNA enzymes offer several important advantages compared to other macromolecular catalysts. First, they are easy to prepare, in an era when most laboratories have access to an automated DNA synthesizer and the cost of DNA phosphoramidites has become quite modest. Second, they are very stable compounds, especially compared to RNA, thus facilitating their use in biophysical studies. Third, we expect that they can be adapted to therapeutic applications that at present make use of antisense DNAs that lack RNA-cleavage activity. In vitro selection could be carried out with DNA analogues, including compounds that are nuclease resistant such as phosphorothioate-containing DNA, so long as these analogues can be prepared in the form of a deoxynucleoside 5'-triphosphate and are accepted as a substrate by a DNA-dependent DNA polymerase. Finally, DNA enzymes offer a new window on our understanding of the macromolecular basis of catalytic function. It will be interesting, for example, to carry out comparative analyses of protein-, RNA-, and DNA-based enzymes that catalyze the same chemical transformation.

Example 4

Other Families of Catalytic DNAs

A starting pool of DNA was prepared by PCR essentially as described in Example 2.B. above, except that the starting pool of DNA comprised molecules containing 40 random nucleotides. Thus, the starting pool of DNA described herein was prepared by PCR using the synthetic oligomer 5'GGG ACG AAT TCT AAT ACG ACT CAC TAT rA GG AAG AGA TGG CGA CAT CTC $N_{40}$GT GAC GGT AAG CTT GGC AC 3' (SEQ ID NO 23), where N is an equimolar mixture of G, A, T and C, and where the DNA molecules were selected for the ability to cleave the phosphoester following the target rA. (See FIG. 4A, also.)

Selective amplification was carried out in the presence of either $Pb^{2+}$, $Zn^{2+}$, $Mn^{2+}$, or $Mg^{2+}$, thereby generating at least four "families" of catalytic DNA molecules. Catalytic DNA molecules demonstrating specific activity were generated in the presence of a variety of cations. At present, the order of reactivity is observed to be $Pb^{2+}$>$Zn^{2+}$>$Mn^{2+}$>$Mg^{2+}$, mirroring the $pK_a$ of the corresponding metal-hydroxide.

After either five (G5) or six (G6) rounds of selective amplification in the presence of the preselected divalent cation, the desired endonuclease activity was obtained. The following description of selective amplification in the presence of $Mg^{2+}$ is intended to be exemplary.

Six rounds of in vitro selective amplification were carried out, following the method described in Example 2 hereinabove, except that the divalent metal used was 1 mM $Mg^{2+}$ rather than 1 mM $Pb^{2+}$. (See also Breaker and Joyce, *Chem. & Biol.* 1: 223–229 (1994), incorporated by reference herein, which describes essentially the same procedure.)

Individual clones were isolated following the sixth round, and the nucleotide sequence of 24 of these clones was determined. All of the sequences began with: 5' GGG ACG AAT TCT AAT ACG ACT CAC TAT rA GG AAG AGA TGG CGA CA (SEQ ID NO 23 from position 1 to 44) and ended with: CGG TAA GCT TGG CAC 3' (SEQ ID NO 23 from position 93 to 107).

The segment in the middle, corresponding to TCTC $N_{40}$ GTGA (SEQ ID NO 23 from position 45 to 92) in the starting pool, varied as follows:

(13) CCG CCC ACC TCT TTT ACG AGC CTG TAC GAA ATA GTG CTC TTG TTA GTA T (SEQ ID NO 24)

(5) TCT CTT CAG CGA TGC ACG CTT GTT TTA ATG TTG CAC CCA TGT TAG TGA (SEQ ID NO 25)

(2) TCT CAT CAG CGA TTG AAC CAC TTG GTG GAC AGA CCC ATG TTA GTG A (SEQ ID NO 26)

(1) CCG CCC ACC TCT TTT ACG AGC CTG TAC GAA ATA GTG TTC TTG TTA GTA T (SEQ ID NO 27)

(1) CCG CCC ACC TCT TTT ACG AGC CTG TAC GAA ATA GTG CTC TCG TTA GTA T (SEQ ID NO 28)

(1) TCT CAG ACT TAG TCC ATC ACA CTC TGT GCA TAT GCC TGC TTG ATG TGA (SEQ ID NO 29)

(1) -CT CTC ATC TGC TAG CAC GCT CGA ATA GTG TCA GTC GAT GTGA (SEQ ID NO 30).

The initial number in parentheses indicates the number of clones having that particular sequence. Note that some mutations (highlighted in bold type) occurred at nucleotide positions other than those that were randomized initially.

The second sequence listed above (i.e., SEQ ID NO 25), which occurred in 5 of 24 clones, was chosen as a lead compound for further study. Its cleavage activity was measured in the presence of a 1 mM concentration of various divalent metals and 1 M NaCl at pH 7.0 and 23° C.:

| metal | $k_{obs}$ (min$^{-1}$) |
|---|---|
| none | n.d. |
| $Mg^{2+}$ | $2.3 \times 10^{-3}$ |
| $Mn^{2+}$ | $6.8 \times 10^{-3}$ |
| $Zn^{2+}$ | $4.2 \times 10^{-2}$ |
| $Pb^{2+}$ | $1.1 \times 10^{-2}$ |

Thus, the lead compound is active in the presence of all four divalent metals, even though it was selected for activity in the presence of $Mg^{2+}$. Conversely, DNA molecules that were selected for activity in the presence of $Mn^{2+}$, $Zn^{2+}$, or $Pb^{2+}$ did not show any activity in the presence of $Mg^{2+}$.

In addition, the population of DNAs obtained after six rounds of in vitro selection in the presence of $Mg^{2+}$, when prepared as all-phosphorothioate-containing DNA analogues, showed $Mg^{2+}$-dependent cleavage activity at an observed rate of $\sim 10^{-3}$ min$^{-1}$. The phosphorothioate-containing analogues were prepared enzymatically so as to have an $R_P$ configuration at each stereocenter. Such compounds are relatively resistant to degradation by cellular nucleases compared to unmodified DNA.

The lead compound was re-randomized at 40 nucleotide positions (underlined), introducing mutations at a frequency of 15% (5% probability of each of the three possible base substitutions). The re-randomized population was subjected to seven additional rounds of in vitro selection. During the last four rounds, molecules that were reactive in the presence of 1 mM $Pb^{2+}$ were removed from the population before the remainder were challenged to react in the presence of 1 mM $Mg^{2+}$. Individual clones were isolated following the seventh round and the nucleotide sequence of 14 of these clones was determined. All of the sequences began with: 5'GGG ACG AAT TCT AAT ACG ACT CAC TAT rA GG AAG AGA TGG CGA CAT CTC (SEQ ID NO 23, from position 1 to 48), and ended with: GTG ACG GTA AGC TTG GCA C 3' (SEQ ID NO 23, from position 89 to 107).

The segment in the middle, corresponding to the 40 partially-randomized positions ($N_{40}$, SEQ ID NO 23, from position 49 to 88), varied as follows:

(4) TAC AGC GAT TCA CCC TTG TTT AAG GGT TAC ACC CAT GTT A (SEQ ID NO 31)

(2) ATC AGC GAT TAA CGC TTG TTT CAA TGT TAC ACC CAT GTT A (SEQ ID NO 32)

(2) TTC AGC GAT TAA CGC TTA TTT TAG CGT TAC ACC CAT GTT A (SEQ ID NO 33)

(1) ATC AGC GAT TCA CCC TTG TTT TAA GGT TGC ACC CAT GTT A (SEQ ID NO 34)

(1) ATC AGC GAT TCA CCC TTG TTT AAG CGT TAC ACC CAT GTT G (SEQ ID NO 35)

(1) ATC AGC GAT TCA CCC TTG TTT TAA GGT TAC ACC CAT GTT A (SEQ ID NO 36)

(1) ATC AGC GAT TAA CGC TTA TTT TAG CGT TAC ACC CAT GTT A (SEQ ID NO 37)

(1) ATC AGC GAT TAA CGC TTG TTT TAG TGT TGC ACC CAT GTT A (SEQ ID NO 38)

(1) ATC AGC GAT TAA CGC TTA TTT TAG CAT TAC ACC CAT GTT A (SEQ ID NO 39).

The number in parentheses indicates the number of clones having that particular sequence. Nucleotides shown in bold are those that differ compared to the lead compound.

Formal analysis of the cleavage activity of these clones is ongoing. The population as a whole exhibits $Mg^{2+}$-dependent cleavage activity at an observed rate of $\sim 10^{-2}$ $min^{-1}$, with a comparable level of activity in the presence of $Pb^{2+}$.

Figure 4A:
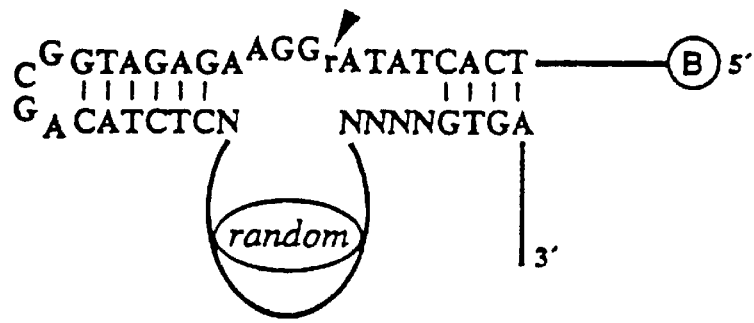
FIGS. 4A and 4B provide two-dimensional illustrations of a "progenitor" catalytic DNA molecule and one of several catalytic DNA molecules obtained via the selective amplification methods disclosed herein, respectively.
Figure 4B:
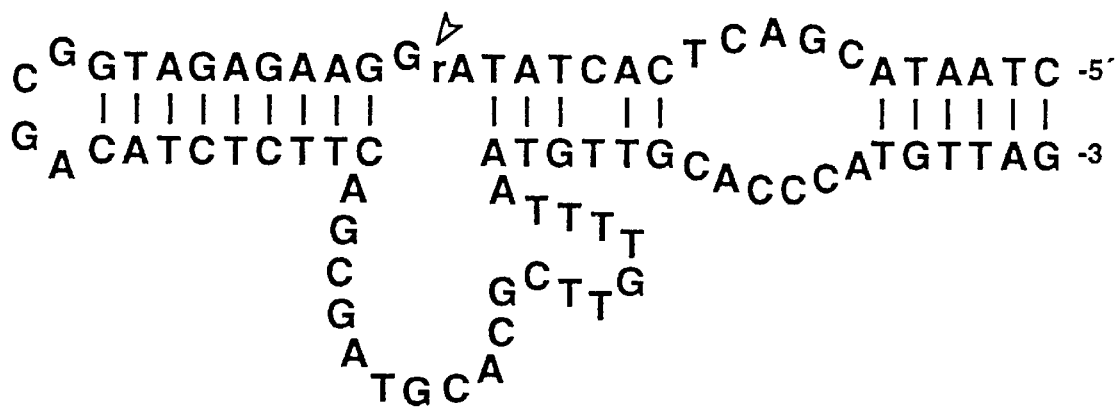

FIGS. 4A and 4B provide two-dimensional illustrations of a "progenitor" catalytic DNA molecule and one of several catalytic DNA molecules obtained via the selective amplification methods disclosed herein, respectively. FIG. 4A illustrates an exemplary molecule from the starting pool, showing the overall configuration of the molecules represented by SEQ ID NO 23. As illustrated, various complementary nucleotides flank the random ($X_{40}$) region.

FIG. 4B is a diagrammatic representation of one of the $Mg^{2+}$-dependent catalytic DNA molecules (or "DNAzymes") generated via the within-described procedures. The location of the ribonucleotide in the substrate nucleic acid is indicated via the arrow. (The illustrated molecule includes the sequence identified herein as SEQ ID NO 25, as well as "beginning" and "ending" sequences of SEQ ID NO 23.)

Endonuclease activity is continuing to be enhanced in each of the aforementioned "families" via in vitro evolution, as disclosed herein, so it is anticipated that enzymatic DNA molecules of increasingly desirable specificities may be generated successfully using the within-disclosed guidelines.

Example 5

DNAs Containing Modified Nucleotides

A DNA molecule containing a modified nucleotide as set forth above can be made using standard procedures well known in the art such as solid phase phosphoramidite chemistry. All that is needed is to use a modified nucleotide of this invention in the synthetic scheme. A modified nucleotide of this invention can also be incorporated into a DNA molecule using enzymes such as polymerases and reverse transcriptases. A reaction mixture for making a DNA molecule comprises one or more modified nucleotides of this invention together with dATP, dGTP, dTTP and dCTP. The modified nucleotides can be in addition to or replace dTTP and/or dCTP.

By way of example, Compound 3 from Scheme 1., FIG. 6, acted as a substrate in place of deoxythymidine triphosphate, dTTP, for thermostable DNA polymerases using typical PCR conditions. Commercially available thermostable DNA polymerases from five organisms were studied; Taq from Thermus aquaticus, Vent from Thermococcus litoralis, Pfu from Pyrococcus furiosus, and rTh from Thennus thennophilus. PCR assays with compound 3 demonstrated its incorporation into the 519 base pair product only with rTh polymerase. Several derivatives of 3 have been shown to be substrates for E. coli DNA polymerase and useful in nick translation and random primed synthesis when they replace dTTP. Homogeneous incorporation of these derivatives in PCR is not possible due to chain termination, see 11c for discussion of derivatives in PCR: a) M. Shimkus, J. Levy, T. Herman, Proc. Natl. Acad. Sci. U.S.A. 1985, 82, 2593–7; b) B. L. Iverson, P. B. Dervan, J. Am. Chem. Soc. 1987, 109, 1241–3. and ref. 10; c) H. Yu, J. Chao, D. Patek, R. Mujumdar, A. S. Waggoner, Nucleic Acids Res. 1994, 22, 3226–32. Successful PCR with this template requires incorporation of 246 modified bases including a single stretch of 8 contiguous thymidines.

Figure 7:
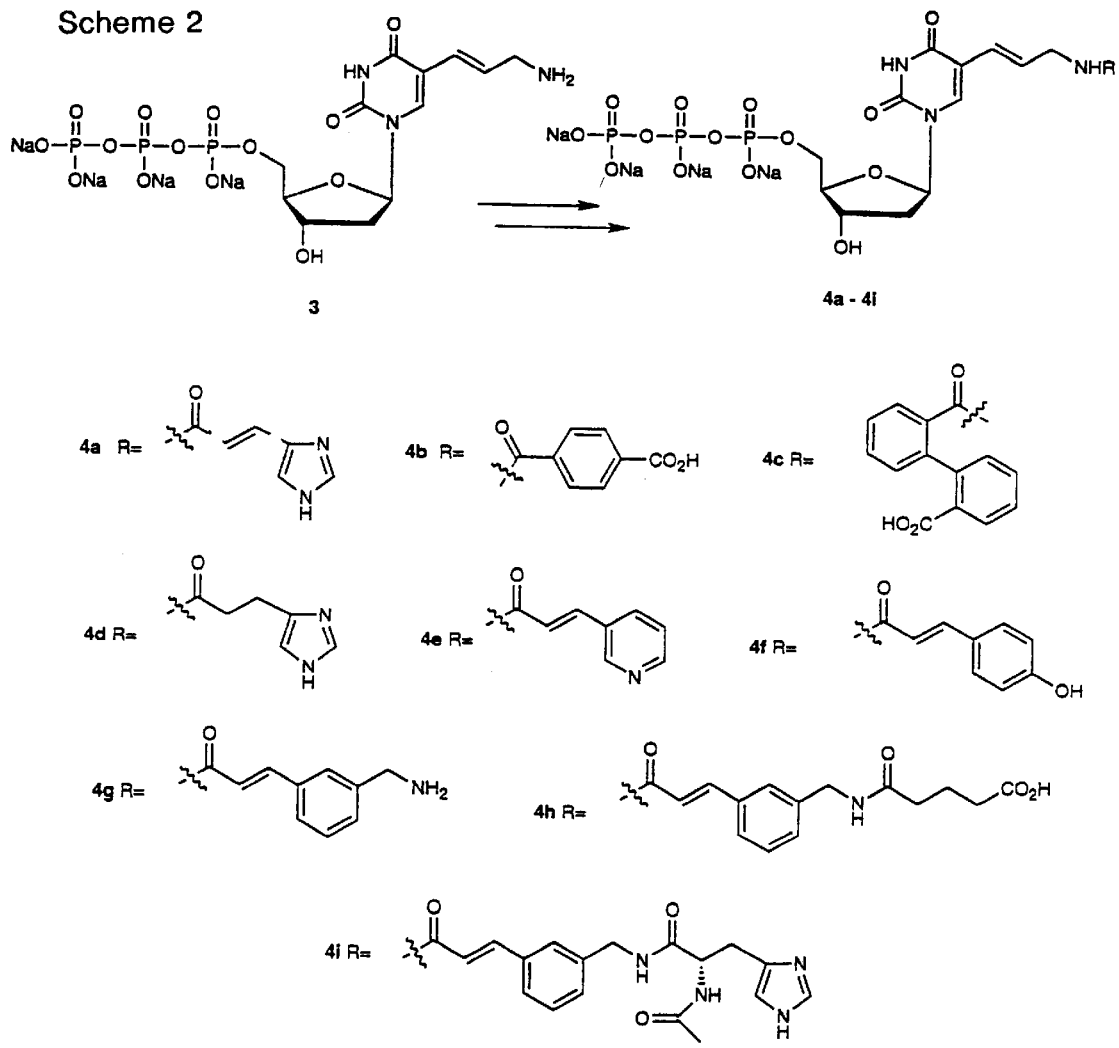
FIG. 7 shows a generalized synthetic scheme for making modified deoxyuridines.

Compound 3 was derivatized with three different N-hydroxysuccinimide esters to prepare Compounds 4a–c (Scheme 2 FIG. 7). Compound 4a, an 4-imidazole acrylic acid derivative, proved to be an excellent substrate for all the polymerases tested producing an amount of PCR product similar to that obtained with dTTP. Further study of substrates 4b and 4c with variation of $Mg^{+2}$ (15 to 30 mM) and analog concentrations (200 to 800 mM) failed to define conditions that allowed for incorporation of these modified bases. To study the structural feature of 4a that allowed for it to be recognized as a good substrate for the polymerases, Compound 4d, a reduced analog of 4a, was synthesized. No conditions could be defined with any of the polymerases that allowed for PCR with 4d suggesting that the rigid and extended a,b-unsaturated arm of the 4-imidazole acrylic acid provided for its activity. To test this structure-activity relationship, 4e–4g maintaining the a,b-unsaturated linker arm common to 4a, were also prepared (Scheme 2, FIG. 7). Compounds 4e–4g were substrates for all the polymerases tested. Compound 4g, with a free amino group, was used as a template for the synthesis of Compounds 4h and 4i. Analog 4h was a good substrate for all thermostable polymerases tested while 4i was a substrate only for rTh polymerase.

Evidence that the modified dUTP's are indeed incorporated into the PCR products is provided in the substantial mobility shift obtained for the modified DNA products that is indicative of both the mass increase associated with the modified base as well as the charge of the DNA product. DNA incorporating analog 4g, which should possess of full positive charge at neutral pH, migrated slower than DNA incorporating 4h that has an increased mass and negative charge at neutral pH. The role of the extended linker arm is apparent in comparing the efficiency of incorporation of 3 with 4g, were both carry a primary amine. The larger derivative 4g bears the extended linker arm and is a robust substrate for PCR as compared to 3.

Reverse transcriptases may also be utilized in conjunction with PCR in in vitro selection schemes of DNA enzymes. We tested the ability of Compounds 3 and 4a–i to act as substrates of Superscript II reverse transcriptase (Gibco/BRL) and determined that all but 4c and 4h were substrates in template directed synthesis assays. The specificity of this reverse transcriptase is broader and not predictive of the structural requirements of the thermostable polymerases.

PCR products obtained using modified dUTP's were cloned and sequenced. PCR products incorporating modified nucleotide analogs were cloned into the vector pCR2.1TOPO using the topoisomerase-activated vector provided from the manufacturer (Invitrogen). The fidelity of incorporation of the modified dUTP's was indistinguishable from that observed with dTTP incorporation in the control reactions. The key criteria for the use of a modified dNTP in an in vitro selection methodology is its ability to serve as a substrate for thermostable polymerases and the resulting product to serve as a template for multiple cycles of PCR amplification. These criteria were met with Compounds 3, 4a and 4e–i.

Analogs 4g and 4h provide for the first examples of the incorporation of cationic and anionic nucleotide analogs into DNA by PCR, dramatically altering its electrostatic properties. With the exception of 4e, the analogs may be regarded as functional equivalents of the amino acids lysine, 3 and 4g; histidine, 4a and 4i; tyrosine, 4f; and aspartic and glutamic acid, 4h. The successful incorporation of L-histidine in analog 4i supports the possibility of incorporation of other natural amino acids as well as small peptides. All the analogs provide new potential for hydrophobic binding interactions that are essential for folding and pocket formation in protein enzymes as well as for $pK_a$ perturbations of functional groups.

A. Synthesis of 5-(3-trifluroacetylaminopropenyl) -2'-deoxyuridine (Compound 2)

5-(3-Trifluroacetylaminopropenyl)-2'-deoxyuridine 2 was first synthesized by Cook and his coworkers[8] from 5-chloromercuri-2'-deoxyuridine 1b. We synthesized 2 from commercially available 5-iodo-2'-deoxyuridine using a similar procedure. A suspension of 5-iodo-2'-deoxyuridine 1a (3.5 g, 10 mmol) in sodium acetate buffer (0.1 M, pH 5.2) was treated with trifluroacetyl allylamide (13 g, 88 mmol) followed by a solution of sodium tetrachloropalladate (2.5 g in 5 ml water). The mixture was stirred at rt for 18 hrs and then filtered through celite. The filtrate was concentrated and extracted several times with ethyl acetate. The combined organic layers were dried over anhydrous magnesium sulfate. The solvent was evaporated to dryness and the product purified by column chromatography on silica gel using ethyl acetate as eluent, 1.7 g (44%) of deoxyuridine derivative 2 was obtained. $^1$H-NMR (CD$_3$OD): 8.11 (s, br, 1H) C-6 H; 6.45 (m, 1H) and 6.16 (m, 2H) vinylic protons and H-1'; 4.32 (m, 1H) H-3'; 3.8, (m, 3H) allylic CH$_2$ and H-4'; 3.75–3.60 (m, 2H) CH$_2$-5',5"; 2.17 (m, 2H) H-2',2".

B. Synthesis of C-5(3-aminopropenyl)-2-deoxyuridinetriphosphate (Compound 3)

Allylamine-deoxyuridine 2 (126 mg, 0.33 mmol) was stirred in dry trimethylphosphate (0.75 ml) with proton sponge (100 mg, 0.47 mmol) at 0° C. Phosphorous oxychloride(99.9% Aldrich, 35 1) was added and the mixture was stirred at 0–4 C. After 2.5 hrs, a solution of tri-n-butylammonium pyrophosphate in anhydrous DMF (0.5 M, 3 ml) and n-tributylamine (0.3 ml) was quickly added to the reaction mixture at 0 C. After 1 min, an aqueous solution of triethylammonium bicarbonate (0.2 M) was poured into the mixture. After evaporation, the residue was treated with aqueous ammonia (2 ml), and stirred overnight at rt. After evaporation of the ammonia, the residue was purified on DEAE-Sephadex A-25 column chromatography using triethylammonium bicarbonate buffer (0.2–0.5 M, pH 7.5). The final purification was achieved by reverse phase HPLC using the gradient 0–3% acetonitrile in 50 mM triethylammoniumbicarbonate buffer over 30 min to give 110 mg (54%) of triphosphate 3. $^1$H-NMR (D$_2$O): 8.17 (s, br, 1H) C-6 H; 6.58–6.54 (d, 1H) and 6.48–6.40 (m, 1H), 6.35 (t, 1H) vinylic protons and H-1'; 4.66 (m, 1H) H-3'; 4.26–4.2 (m, 3H) 5', 5"CH, and H-4'; 3.70 (d, 2H) allylic CH$_2$; 2.41 (m, 2H) H-2',2". $^{13}$C-NMR (D$_2$O): 166.67; 153.35; 141.0 ; 128.74; 124.7; 114.00; 88.27; 87.90; 72.7; 67.66; 43.60; 41.98. $^{31}$P-NMR (D$_2$O): −9.42 (d); −10.73 (d); −21.38 (t). MS (Electrospray): m/z 589 [M+H$^+$]; 611 [M+Na$^+$]; 633[M+2Na$^+$−2H$^+$]. Anal. calcd for C$_{12}$H$_{16}$N$_3$Na$_4$O$_{14}$P$_3$: C, 23.58; H, 2.64; N, 6.88. Found: C, 23.75; H, 2.81; N, 7.00.

General synthesis of modified dUTPs 4a, 4d, 4e, and 4f

Allylamine- dUTP 3 (30 mg, 50 mol) was treated with a slight excess of the corresponding N-hydroxysuccinimide ester in 0.1 M sodium borate buffer and DMF (1:1) at rt and stirred for 10–20 hrs. After completion of the reaction (as monitored on TLC using ammonia, water and isopropanol, 2:1:1), the mixture was evaporated to dryness. The triphosphates were purified by reverse phase HPLC. $^1$H nuclear magnetic resonance ($^1$H-NMR) spectra were recorded on a Fourier Transform 400-MHz, (100-MHz for $^{13}$C-NMR, 161.9 MHz for $^{31}$P-NMR) spectrometer and are reported in parts per million (ppm). All modified dUTPs were purified using preparative RP-HPLC; Waters PrepPak 500 column, C-18, 300 Å poresize, 15 mm particle size, 4.7×30 cm, flow rate 80 ml/min. For all modified dUTPs, the triethylammonium counterion was converted to the sodium ion using the standard procedure.

Modified dUTP imidazole deoxyuridylate (Im-dU)4a: 26 mg (73 %). $^1$H-NMR (D$_2$O): (7.94(s, br, 1H) H-6; 7.86 (s, br, 1H) and 7.42 (m, 2H), 6.6 (d, 1H) imidazole-H and vinylic protons; 6.44 (m, 1H) and 6.35–6.30 (m, 2H) allylamine vinylic protons and H-1'; 4.64 (s, br, 1H) H-3'; 4.20–4.19 (d, br, 3H) 5', 5"CH$_2$ and H-4'; 4.01 (d, 2H) allylic CH$_2$; 2.38 (m, 2H) H-2',2". $^{13}$C-NMR (D$_2$O): (170.75; 166.45; 153.09; 140.25; 133.16; 129.75; 124.52; 114.57; 114.50; 87.96; 87.83; 87.75; 73.08; 72.78; 67.88; 44.19; 41.07; 32.70. $^{31}$P-NMR CD$_2$O): (−0.36 (d); −10.94 (d); −21.43 (t). MS (Electrospray): m/z 709 [M+H$^+$]; 731 [M+Na$^+$]; 753 [M+2Na$^+$−H$^+$]; 775 [M+3Na$^+$−2H$^+$]. Anal. calcd for C$_{18}$H$_{20}$N$_5$Na$_4$O$_{15}$P$_3$: C, 29.57; H, 2.76; N, 9.58. Found: C, 29.15; H, 2.85; N, 9.42.

Modified dUTP 4d: 24 mg (67%). $^1$-NMR (D$_2$O): (8.3 (s, 1H) imidazole; 7.93 (s, br, 1H) H-6; 7.1 (s, 1H) imidazole, 6.32 (m, 2H) and 6.15 (d, 1H) vinyl protons and H-1'; 4.64 (s, br, 1H) H-3'; 4.20–4.19 (d, br, 3H) 5', 5"CH$_2$ and H-4'; 3.8 (m, 2H) allylic CH$_2$; 2.99 (t, 2H) and 2.67 (t, 2H) 2CH$_2$; 2.38 (m, 2H) H-2',2". $^{13}$C-NMR (D$_2$O): (182.0; 177.54; 176.0; 166.67; 153.35; 140.23 ; 129.93; 124.24; 1 14.88; 88.15; 88.06; 87.86; 73.2; 67.79; 51.26; 43.59; 41.35; 37.74. $^{31}$P-NMR (D$_2$O): (−0.45 (d); −11.00 (d); −21.92 (t). MS (Electrospray): m/z 711 [M+H$^+$]; 733 [M+Na$^+$]; 755 [M+2Na$^+$−H$^+$]; 777 [M+Na$^+$−2H$^+$]. Anal. calcd for C$_{18}$H$_{22}$N$_5$Na$_4$O$_{15}$P$_3$: C, 29.48; H, 3.02; N, 9.55. Found: C, 29.80; H, 3.11; N, 9.63

Modified dUTP 4e: 24 mg (65%). $^1$H-NMR (D$_2$O): (8.7 (s, br, 1H), 8.47 (s, br, 1H), 8.12 (d, 1H) pyridyl; 7.93 (s, br, 1H) H-6; 7.43 (m, 2H) pyridyl and acrylyl-H, 6.79 (d, 16 Hz, 1H) acrylyl-H; 6.48 (m, 1H) and 6.35–6.27 (m, 2H) allylamine vinylic protons and H-1'; 4.77 (s, br, 1H) H-3'; 4.22–4.18 (d, br, 3H) 5', 5"CH$_2$ and H-4'; 4.04 (s, br, 2H) allylic CH$_2$; 2.35 (m, 2H) H-2',2". $^{13}$C-NMR (D$_2$O): ( 169.99; 166.56; 153.14; 140.42; 139.44; 138.05; 129.61; 125.02; 124.73; 114.57; 87.90; 87.91; 87.85; 72.77; 67.73; 44.24; 43.59; 41.11. $^{31}$P-NMR (D$_2$O): (−0.45 (d); −11.00 (d); −21.92 (t). Anal. calcd for C$_{18}$H$_{22}$N$_5$Na$_4$O$_{15}$P$_3$H$_2$O: C, 31.60; H, 3.04; N, 7.37. Found: C, 31.95; H, 3.11; N, 7.78.

Modified dUTP 4f: 24 mg (62%). $^1$H-NMR (D$_2$O): (7.92 (s, 1H) H-6; 7.55 (d, br, 2H) phenyl; 7.46 (d, 16 Hz, 1H) vinyl-H. 6.89 (d, 1H) phenyl; 6.55 (d, 16 Hz, 1H) vinyl-H; 6.5–6.28 (m, 3H) allylamine vinylic protons and H-1'; 4.64 (s, br, 1H) H-3'; 4.20–4.19 (d, br, 3H) 5', 5"CH$_2$ and H-4'; 4.01 (m, 2H) allylic CH$_2$; 2.38 (m, 2H) H-2',2". $^{13}$C-NMR (D$_2$O): (171.08; 166.44; 166.36; 160.13; 153.06; 143.25; 140.19; 132.35; 129.82; 128.96; 124.46; 119.58; 118.43; 114.57; 88.02; 87.82; 87.73; 73.08; 67.93; 44.22; 40.94. $^{31}$P-NMR (D$_2$O): (−0.45 (d); −11.00 (d); −21.92 (t). MS (Electrospray): m/z 691 [M+Na$^+$]; 667 [M+H$^+$]. Anal. calcd for C$_{21}$H$_{22}$N$_3$Na$_4$O$_{16}$P$_3$: C, 33.31; H, 2.93; N, 5.55. Found: C, 33.67; H, 3.12; N, 5.21.

Modified dUTP 4b: Allylamine dUTP 3 (30 mg, 50 (mol) was reacted with monomethylterephthalic acid-N-hydroxysuccinimide ester (70 mg, 250 (mol ) in 0.1 M sodium borate buffer and DMF (1:1) at rt for 12 hrs and the resulting methyl ester was hydrolyzed by adding IN sodium hydroxide to produce dUTP 4b. Excess sodium hydroxide was neutralized to pH 7 using 1N HCl at 0 (C. The reaction mixture was then evaporated to dryness and the residue was purified by reverse phase HPLC to give 22 mg (58 %) of dUTP 4b. $^1$H-NMR (D$_2$O): (7.90 (d, 2H) phenyl; 7.76 (s, br, 1H) H-6; 7.67 (d, 2H) phenyl; 6.23–6.14 (m, 3H) allylamine vinylic protons and H-'; 4.46 (s, br, 1H) H-3'; 4.03 (s, br, 3H) 5', 5"CH$_2$ and H-4'; 3.95 (s, br, 2H) allylic CH$_2$; 2.2 (m, 2H) H-2',2". $^{31}$P-NMR (D$_2$O): (−0.36 (d); −10.94 (d); −21.43 (t). MS (FT-MALDI): 759.9685; C$_{20}$H$_{24}$N$_3$Na$_4$O$_{17}$P$_3$ (calcd. 759.6975); 781.9481 [M+Na$^+$, calcd. 781.9061].

Modified dUTP 4c: Allylamine-dUTP 3 (30 mg, 50 (mol) was reacted with biphenic anhydride (56 mg, 250 (mol) in 0.1 M sodium borate buffer and DMF (1:1) at rt and stirred for 12 hrs. After completion, the reaction mixture was evaporated to dryness and residue was purified by reverse phase HPLC to give 29 mg (71%) of 4c. $^1$H-NMR (D$_2$O): (7.67 (s, 1H) H-6; 7.5–7.05 (m, 8H) biphenyl protons; 6.30 (t, 1H) H-1'; 5.9 (d, 1H) and 5.8 (m, 1H) allylamine vinylic protons; 4.63 (s, br, 1H) H-3'; 4.21 (s, br, 3H) 5', 5"CH$_2$ and H-4'; 3.9–3.3 (d, br, 2H) allylic amine CH$_2$; 2.42 (m, 2H) H-2',2". $^{31}$P-NMR (D$_2$O): (−0.36 (d); −10.94 (d); −21.43 (t). MS (FT-MALDI): 836.9997, C$_{26}$H$_{24}$N$_3$Na$_4$O$_{17}$P$_3$ (calcd. 834.9989).

Modified dUTP 4g: Allylamine-dUTP 3 (30 mg, 50 (mol) was reacted with 3-trifluroacetylamiomethyl-trans-cinnamic acid-N-hydroxysuccinimideester (100 mg, 250 (mol ) in 0.1 M sodium borate buffer and DMF (1 1) at rt for 24 hrs. The resulting reaction mixture was evaporated to dryness. The residue was added to conc. ammonia (1 mL). The reaction mixture was evaporated to dryness and the residue was purified by reverse phase HPLC to give 23 mg (60%) of 4g. $^1$H-NMR (D$_2$O): (8.05 (s, 1H) H-6; 7.53–7.40 (m, 5H) phenyl and cinnamic vinyl- H; 6.98 (d, 16 Hz, 1H) cinnamic vinyl-H; 6.43–6.32 (m, 3H) allylamine vinylic protons and H-1'; 4.71 (s, br, 1H) H-3'; 4.32–3.95 (m, 7H) 5', 5"CH$_2$, H-4", allylic CH$_2$, benzylic CH$_2$; 2.38 (m, 2H) H-2',2". $^{13}$C-NMR (D$_2$O): (170.49; 167.11; 153.58; 142.39; 140.20; 137.55; 132.57; 132.02; 131.66; 129.47; 129.41; 124.59; 123.48; 114.64; 87.96; 87.87; 87.74; 72.51; 67.62; 45.15; 44.00; 41.22. $^{31}$P-NMR (D$_2$O): (−0.5.36 (d); −10.9 (d); −21.16 (t). MS (Electrospray): m/z 683 [MH$^+$]; 705 [M+Na$^+$]; 727 [M+2Na$^+$−H$^+$]; 749 [M+3Na$^+$−2H$^+$]; 771 [M+4Na$^+$−3H$^+$].

Modified dUTP 4h: Benzylamine-dUTP 4g (38 mg, 50 (mol) was reacted with glutaric anhydride (57 mg , 0.5 mmol) in 0.1 M sodium borate buffer and DMF (1: 1) at rt for 12 hrs. After the completion of the reaction, the mixture was evaporated to dryness and the residue was purified by reverse phase HPLC to give 26 mg (60%) of 4g. $^1$H-NMR (D$_2$O): (7.90 (s, 1H) H-6; 7.57–7.31 (m, 5H) phenyl and cinnamic vinyl- H; 6.68 (d, 16 Hz, 1H) cinnamic vinyl-H, 6.47–6.28 (m, 3H) allylamine vinylic protons and H-1'; 4.67 (s, br, 1H) H-3'; 4.37 (m, 2H), 4.22 (m, 3H) 5', 5"CH$_2$,H-4'; 4.01 (d, br, 2H) allylic CH$_2$; 2.39 (m, 2H), 2.29 (m, 2H), 2.19 (m, 2H), 1.83 (m, 2H) 3XCH$_2$ for glutaric acid and H-2',2". $^{13}$C-NMR(D$_2$O): (184.99); 178.82; 170.83; 153.94; 143.27; 141.10; 140.39; 137.16; 131.79; 131.23; 129.68; 129.5; 124.79; 122.85; 114.71; 87.95; 87.86; 87.71; 72.67; 67.69; 51.31; 45.21; 44.23; 40.98; 39.20; 37.91; 24.91. $^{31}$P-NMR (D$_2$O): (−0.5.26 (d); −10.5 (d); −21.23 (t). MS (Electrospray): m/z 819 [M+Na$^+$]; 841 [M+2Na$^+$-H$^+$]; 863 [M+3Na$^+$−2H$^+$]; 885 [M+4Na$^+$−3H$^+$]. Anal. calcd for C$_{27}$H$_{31}$N$_4$Na$_4$O$_{18}$P$_3$: C, 36.67; H, 3.53; N, 6.33. Found: C, 36.37; H, 3.81; N, 6.10.

Modified dUTP 4i: N-Acetyl histidine was treated with N-hydroxysuccinimide (38 mg, 0.32 mmol) and 1,3-dicyclohexycarbodiimide (49 mg, 0.24 mmol) in DMF (3 ml) at rt. After 12 hrs, the reaction mixture was filtered and the filtrate was added to a solution of sodium borate and DMF (1:1) containing 4g (38 mg, 50 (mol). After 10 hrs at rt, the reaction mixture was evaporated to dryness and the residue was purified on reverse phase HPLC to give 32 mg (68%) of 4i. $^1$H-NMR ( D$_2$O): (7.93 (s, bs, 1H) H-6; 7.6–7.32 (m, 5H) phenyl and cinnamyl vinyl-H; 7.14 (d, br, 1H) imidazole-H; 6.75, 6.67 (d, br, 2H ) cinnamic vinyl-H and imidazole-H; 6.42–6.26 (d, 3H) allylamine vinylic protons and H-1'; 4.78 (s, br, H) H-3'; 4.23–4.03 (m, 8H) 5', 5"CH$_2$ and H-4', benzylic CH$_2$ and histidine -H; 3.00 (m, 2H) histidine —CH$_2$; 2.19 (m, 2H) H-2',2"; 2.02 (s, 3H) N-acetyl CH$_3$. $^{13}$C-NMR (D$_2$O): (176.54; 175.22; 170.81; 166.80; 153.30; 143.24; 140.83; 140.29; 137.17; 137.08; 131.62; 131.45; 129.79; 129.51; 128.99; 124.58; 122.89; 114.68; 87.96; 87.80; 87.71; 72.71; 72.39; 67.73; 56.54; 45.05; 44.13; 41.15; 30.82; 24.13. $^{31}$P-NMR (D$_2$O): (−5.39 (d); −10.41 (d); −20.82 (t). MS (FT-MALDI): 884.1474, C$_{30}$H$_{38}$N$_7$O$_{17}$P$_3$Na$^+$ (calcd 884.1435); 906.1301, C$_{30}$H$_{38}$N$_7$O$_{17}$P$_3$+2Na$^+$−H$^+$(calcd 906.1254).

Example 6

Reverse Transcriptase Study

Reverse transcriptase assays: Template-directed extension was performed by addition of 10 pmol template DNA 5'-GCT AAA AAA GCT GCT AAA AAG CTG CTA AAA GCT GCT AAA GCT AAG CTA GCT CCC TTT AGT GAG GGT TAA TTG C-3' (SEQ ID NO 40) to 10 pmol primer DNA 5'-GCA ATT AAC CCT CAC TAA AGG G-3' (SEQ ID NO 41) followed by Superscript II reverse transcriptase (Gibco, 200 units.(1$^{−1}$). The reaction (25 (1) contained 0.2 mM of dATP, dCTP, dGTP and 0.4 mM analog. Trace quantities of ((−$^{32}$P(-dATP was included to allow the extension efficiency to be monitored. All components except reverse transcriptase were combined, incubated at 90° C. and cooled to 37° C. to anneal the primer. The enzyme (600 units) was added and the reaction mixture was incubated at 37 (C. The DNA was precipitated in ethanol and then dissolved in gel-loading buffer containing urea and heated for 3 min at 90° C. After separation on a 10 % denaturing acrylamide gel, the samples were further analyzed with a PhosphorImager.

Example 7

Catalytic DNAs Containing Modified Nucleotides

In Vitro Selection. An initial library was generated by template-directed extension of 2 nmol of 5'-biotin-d (GGAAAAA)r(GUAACUAGAGAU)-d (GGAAGAGATGGCGAC)-3' (SEQ ID NO 42) on 3 nmol of 5'-GTGCCAAGCTTACCG-N$_{50}$-GTCGCCATCTCTTCC-3' (SEQ ID NO 43) (N=G, A, T, or C) in a 1-ml reaction mixture containing 10 units $\mu l^{-1}$ Superscript II reverse transcriptase (GIBCO/BRL), 3 mM $MgCl_2$, 75 mM KCl, 50 mM tris(hydroxymethyl) aminomethane (Tris; pH 8.3), and 0.25 mM each of dATP, dCTP, dGTP, and the imidazole-functionalized dUTP analogue (Sakthivel & Barbas, 1998). All components except reverse transcriptase were combined, incubated at 90° C. for 30 sec, then cooled to 37° C. over 5 min. Reverse transcriptase was added and the mixture was incubated at 37° C. for 1 hr, then quenched by addition of $Na_2EDTA$. Extension products were purified by denaturing polyacrylamide gel electrophoresis (PAGE), followed by elution at 4° C. for 16 hr.

The purified extension products (900 $\mu l$; ~1 nmol) were added to a 300-$\mu l$ solution containing 600 mM NaCl, 0.4 mM $Na_2EDTA$, and 200 mM N-(2-hydroxyethyl)-piperazine-N'-3-propanesulfonic acid (EPPS; pH 7.0), and immobilized on an affinity column containing 200 $\mu l$ of UltraLink™ Immobilized Streptavidin PLUS gel (Pierce), that had previously been equilibrated with three 200-$\mu l$ volumes of wash buffer (150 mM NaCl, 0.1 mM $Na_2EDTA$, and 50 mM EPPS (pH 7.0)). Following immobilization, the column was rinsed with five 200-$\mu l$ volumes of wash buffer, five 200-$\mu l$ volumes of ice-cold 0.1 N NaOH/150 mM NaCl, and five 200-$\mu l$ volumes of wash buffer at 37° C., then eluted at 37° C. over 1 hr with three 200-$\mu l$ aliquots of reaction buffer (10 $\mu M$ $Zn^{2+}$, 2 mM $MgCl_2$, 150 mM NaCl, 50 mM EPPS (pH 7.5)). Eluted molecules were ethanol precipitated in the presence of 100 pmols each of the primers 5'-biotin-GGAAGAGATGGCGAC-3' (SEQ ID NO 44) and 5'-GTGCCAAGCTTACCG-3' (SEQ ID NO 45), and PCR amplified in a 400-$\mu l$ volume (Breaker, et al., Chem. Biol. 2: 655–660 (1995)). The PCR products were brought to a final NaCl concentration of 150 mM, immobilized as above on a column containing 50 $\mu l$ of the streptavidin gel, rinsed with five 100-$\mu l$ volumes of wash buffer, and eluted with two 40-$\mu l$ volumes of 0.1 N NaOH/150 mM NaCl to recover the non-biotinylated strand. The isolated DNAs were ethanol precipitated and used as templates in a primer extension reaction to begin the next round of in vitro selection. Rounds 2–10 were carried out as above except that the reaction scale was reduced 20-fold during the extension step and 4-fold during PCR and the selection times were reduced to 30 min for round 8 and 1 min for rounds 9 and 10.

Beginning with the population of molecules obtained following the 10th round of selection, four different lineages were initiated, differing with respect to the level of mutagenesis and the concentration of $Zn^{2+}$. Random mutations was introduced by hypermutagenic PCR (Vartanian, et al., Nucleic Acids Res.24: 2627–2631 (1996)). Initial libraries for the four lineages were constructed by extension of the all-RNA primer 5'-GGAAAAAGUAACUAGAGAUGG AAGAGAUGGCGAC-3' (SEQ ID NO 46), using reverse transcriptase as a DNA-dependent DNA polymerase in the presence of either the mutagenized or non-mutagenized DNA templates. Single-stranded molecules were isolated by immobilizing the extension products on streptavidin columns as described above, rinsing with five 100-$\mu l$ volumes of wash buffer, incubating in a 40-$\mu l$ solution containing 8 M urea, 0.1 mM $Na_2EDTA$, and 50 mM EPPS (pH 7.0) at 90° C. for 2 min, and eluting from the column, followed by ethanol precipitation. The recovered molecules were resuspended in 15 $\mu l$ of $H_2O$, preincubated at 37° C. for 5 min, and allowed to react at 37° C. following addition of 5 $\mu l$ of a 4× reaction buffer containing either 4 or 40 $\mu M$ $Zn^{2+}$, 4 mM $Mg^{2+}$, 600 mM $Na^+$, and 200 mM EPPS (pH 7.0). Reaction times were decreased from 1 min for round 11 to 10 sec for round 16. Reacted molecules were isolated by PAGE in a 10% denaturing gel, eluted from the gel, and amplified by asymmetric PCR to begin the next round of selection.

Intramolecular Cleavage Reaction. Full-length precursor molecules corresponding to cloned individuals obtained following the 16th round of selection were prepared as described above for the populations after rounds 11–16. Cleavage was carried out at 37° C. following addition of 4× reaction buffer and quenched by addition of an equal volume of a mixture containing 8 M urea, 20% sucrose, 90 mM Tris-borate (pH 8.3), 10 mM $Na_2EDTA$, 0.05% xylene cyanol, 0.05% bromophenol blue, and 0.1% SDS. Reaction products were separated by PAGE in a 20%,o denaturing gel and analyzed using a Molecular Dynamics PhosphorImager.

Chemical Synthesis of Substrates and Enzymes. RNA substrates were prepared by chemical synthesis and deprotected as described previously (Wincott, et al., Nucleic Acids Res. 23: 2677–2684 (1995)). Deprotected substrates were purified by denaturing PAGE. Imidazole-containing DNA enzymes were synthesized using a Pharmacia Gene Assembler Special automated DNA/RNA synthesizer, employing an imidazole- functionalized-deoxyuridine phosphoramidite with a coupling time of 5 min. The molecules were deprotected according to standard protocols, desalted using a NAP-5 column (Pharmacia Biotech), purified by HPLC using a 301VHP575P anion exchange column (Vydac) and a gradient of 0.1–0.25 M NaCl, and 10 mM Tris (pH 8.0) over 30 min, and ethanol precipitated. Purification of imidazole-functionalized enzymes by PAGE was found to reduce catalytic activity, perhaps due to modification mediated by trace amounts of the gel polymerization catalyst.

Identification of Cleavage Products. A multiple-turnover reaction was carried out in a mixture containing 20 pmols enzyme, 200 pmols substrate, 10 $\mu l$ $ZnSO_4$, 1 mM $MgCl_2$, 150 mM NaCl, and 50 mM EPPS (pH 7.5), which was incubated at 37° C. for 15 min. Reaction products were desalted using a NAP-5 column and redissolved in 10 $\mu l$ of $H_2O$. 1 $\mu l$ of the aqueous solution was added to a mixture of 2,4,6-trihydroxyacetophenone, 2,3,4-trihydroxyacetophenone, and ammonium citrate in $H_2O$/AcN (1:1 v/v; Zhu, et al., Rapid Corn. Mass Spec. 10: 383–388 (1996)). Matrix-assisted laser desorption/ionization (MALDI) mass spectrometry experiments were performed on a PerSeptive Biosystems Voyager-DE, mass spectrometer with delayed extraction. Samples were irradiated with a nitrogen laser (Laser Science Inc.) Operated at 337 nm. Ions were accelerated with a deflection voltage of 20,000 V and differentiated according to their m/z ratio using a time-of-flight mass analyzer. Spectra were obtained in positive ion mode.

Kinetic Analysis. Unless otherwise stated, all reactions were carried out in the presence of 10 $\mu M$ $ZnSO_4$, 1 mM $MgCl_2$, 150 mM NaCl, and 50 mM EPPS (pH 7.5). The pH of the buffer solution was adjusted in reference to the final reaction mixture at 37° C. Reactions were initiated by combining separate solutions of enzyme and substrate, each containing the final concentration of buffer and salts at 37° C. Aliquots were removed from the reaction mixtures at various times and quenched by addition to an equal volume of a mixture containing 8 M urea, 20% sucrose, 90 mM Tris -borate (pH 8.3), 10 mM $Na_2EDTA$, 0.05% xylene cyanol, 0.05% bromophenol blue, and 0.1% SDS. Radiolabeled substrates and products were separated by denaturing PAGE and quantitated using a Molecular Dynamics PhosphorImager.

For reactions carried out under multiple-turnover (excess substrate) conditions, a value for $k_{obs}$ was obtained for each substrate concentration from a best-fit line, typically based on five data points obtained over the first 10%1 of the reaction. $k_{cat}$ and $K_M$ values were obtained from a best-fit curve to a substrate saturation plot of $k_{obs}$ versus [substrate], based on the equation $k_{obs}$=[substrate]$k_{cat}$/([substrate]+$K_M$). Observed rate constants for single-turnover (excess enzyme) reactions were obtained from a curve fitted to a plot of fraction reacted versus time, based on the equation y=x(1−$e^{-kt}$), where v is the fraction reacted at time t, x is the fraction reacted at time i=∞, and k is the observed rate constant. Kinetic values typically exhibited <20% variation for identical experiments performed on different days.

$Zn^{2+}$ and pH Dependence. The dependence of the catalytic rate on $Zn^{2+}$ concentration was measured under single-turnover conditions employing 100 nM enzyme, 1 nM [5'-$^{32}$P]-labeled substrate, 1–100 μM $ZnCl_2$, 1 mM $MgCl_2$, 150 mM NaCl, and 50 mM EPPS (pH 7.5) at 37° C. The dependence on pH was measured under single-turnover reaction conditions employing either 100 or 400 nM enzyme, 1 nM [5'-$^{32}$P]-labeled substrate, 10 MM $ZnCl_2$, 1 mM $MgCl_2$, 150 mM NaCl, and 50 mM buffer (pH 5.9–8.2) at 37° C. The pH range for reactions buffered by 2-[N-morpholino]-ethanesulfonic acid (MES) was 5.9–6.7, by 1,4-piperazinediethanesulfonic acid (PIPES) was 6.6–7.6, and by EPPS was 7.5–8.2.

Figure 8A:
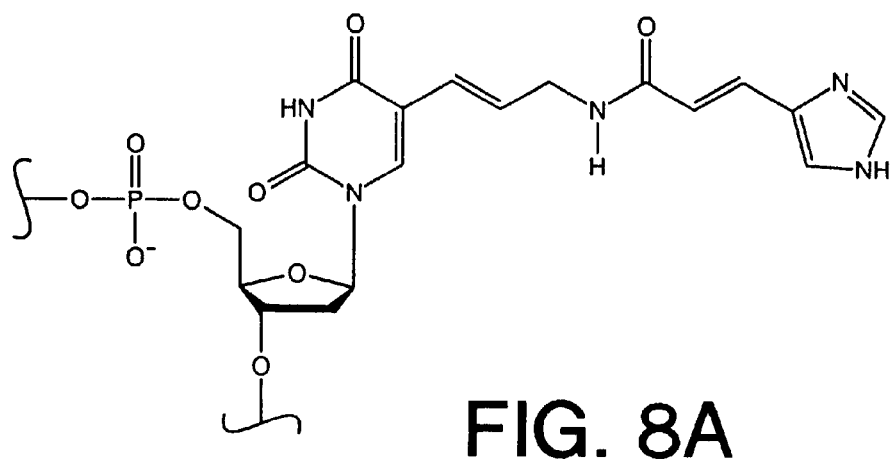
FIGS. 8A–8B show in vitro selection of imidazole-functionalized RNA-cleaving DNAs. (a) Chemical structure of the C5-imidazole-deoxyuridine analogue that was incorporated in place of thymidine. (b) Library of imidazone-containing DNA molecules. Each molecule contained a 5' biotin (encircled B), 12 target ribonucleotides (sequence shown), (SEQ ID NO 47) and 50 random sequence deoxy-nucleotides ($N_{50}$). Ten rounds of selective amplification yielded molecules that underwent phosphoester cleavage at one of three positions within the target ribonucleotide region (arrows). After 16 rounds of selective amplification, molecules underwent cleavage only at the position following the tenth target ribonucleotide (large arrow).
Figure 8B:
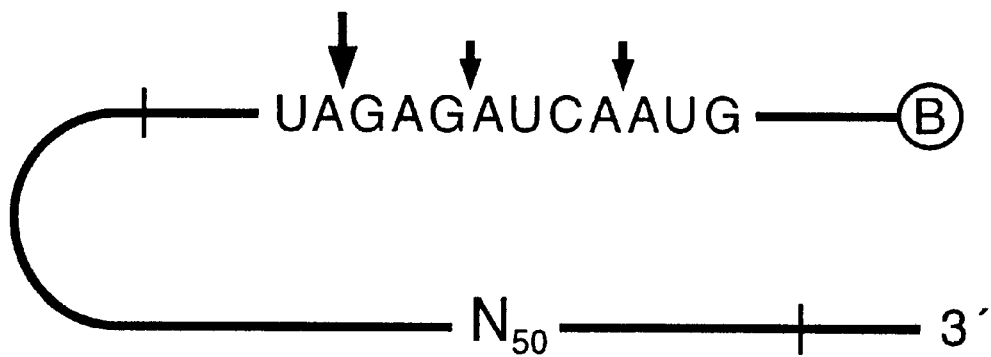

A library of approximately $10^{15}$ different imidazole-containing DNA molecules was constructed, replacing thymidylate with the C5-imidazole derivative of deoxyuridylate shown in FIG. 8a. The imidazole-containing analogue was incorporated as a deoxynucleoside 5'-triphosphate by a primer extension reaction employing reverse transcriptase as a DNA-dependent DNA polymerase. The primer contained a 5' biotin moiety, followed (in a 5' to 3' direction) by a short oligodeoxynucleotide spacer and 12 potentially cleavable ribonucleotides. It was hybridized to a DNA template that contained a primer binding site, followed (in a 3' to 5' direction) 50 random oligodeoxynucleotides and 15 nucleotides of fixed sequence (FIG. 8b). The resulting double-stranded molecules were attached to a streptavidin solid support and the non-biotinylated strand was removed by brief washing with 0.1 N NaOH. The remaining imidazole-enhanced single-stranded DNA molecules were challenged to cleave one of the phosphodiester linkages within the attached RNA substrate, thereby becoming detached from the solid support. The reaction conditions were chosen to resemble those inside a living cell, employing 10 μM $Zn^{2+}$, 2 mM $Mg^{2+}$, and 150 mM $Na^+$ at pH 7.5 and 37° C. The released molecules were recovered and amplified by PCR, using the fixed regions surrounding the random region as primer binding sites. The PCR products were used to construct a new population that was enriched with catalytically active molecules.

A total of 16 rounds of selective amplification were performed to obtain the best catalysts. During the first seven rounds, the reaction time was one hr. In order to increase the stringency of selection, the reaction time was decreased to 30 min for round 8 and to 1 min for rounds 9 and 10. Individual molecules were isolated from the population by shotgun cloning following the 8th and 10th rounds and were sequenced. Several distinct families were found to occur among the cloned individuals, each appearing to have been derived from a single founder molecule. The catalytic activity of various cloned individuals was assayed, revealing three preferred cleavage sites within the 12-nucleotide RNA substrate domain (FIG. 8b). Some, but not all, of the cloned individuals were able to cleave an attached RNA substrate that was surrounded by RNA rather than DNA sequences.

The population of molecules obtained following the 10th round of in vitro selection was divided into four lineages, two that were randomly mutagenized prior to the 11th and 14th rounds, and two that were not. Of the two mutagenized and two non-mutagenized lineages, one was allowed to react in the presence of 1 μM $Zn^{2+}$ and the other in the presence of 10 μM $Zn^{2+}$. Unlike during the first 10 rounds, when the molecules were required to cleave themselves off the solid support, the last six rounds were carried out in solution. The reacted molecules were selected on the basis of their increased electrophoretic mobility in a denaturing polyacrylamide gel compared to unreacted molecules.

Following the 16th round of in vitro selection, the population from each of the four lineages exhibited a strong preference for cleavage at a particular RNA phosphodiester (FIG. 8b). Cloning and sequencing revealed six distinct families, four that had been identified following the 10th round of selection, and two that appeared to be novel. A typical representative of each of these families is shown in FIG. 9. Each contains a region of high sequence similarity ~20 residues in length that is present at various locations within the previously-random domain. Preliminary kinetic analysis of representatives of each family demonstrated varying rates of cleavage of the attached RNA substrate.

Figure 10:
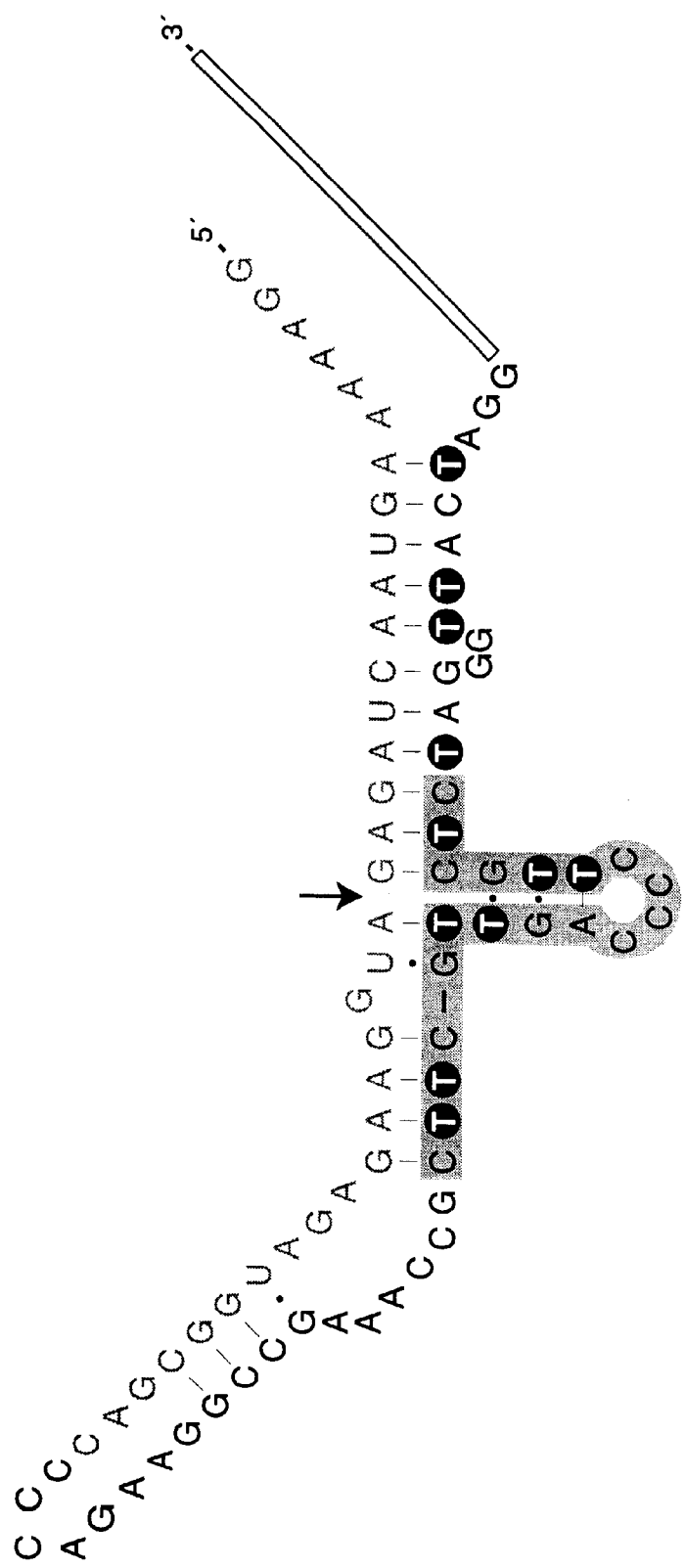
FIG. 10 shows the 16.2-11 clone in an intramolecular cleavage format. The gray letters at the 5' end of the molecule correspond to the 34 nucleotides of the attached RNA substrate. Black letters correspond to the 50 nucleotides of the previously-random region. Highlighted Ts correspond to imidazole-containing deoxyuridine residues. The region surrounded in gray corresponds to the minimal catalytic motif. The open rectangle represents the fixed primer binding region (SEQ ID NO 55).

Identification of the Catalytic Motif. The cloned individual that exhibited the highest level of catalytic activity was derived from the mutagenized lineage that was made to react in the presence of 10 μM $Zn^{2+}$. It is designated as "16.2-11", the 11th clone obtained from the second lineage after the 16th round of selection. Examination of its sequence suggested the presence of several Watson-Crick base-pairing interactions between the imidazole-functionalized DNA and nucleotides within the RNA substrate domain surrounding the cleavage site (FIG. 10). In addition, there appeared to be a short hairpin structure within the DNA, located close to the cleavage site and containing four imidazole-substituted deoxyuridine residues. The observation of sequence covariation among the cloned individuals provided some support for the putative hairpin.

Figure 11:
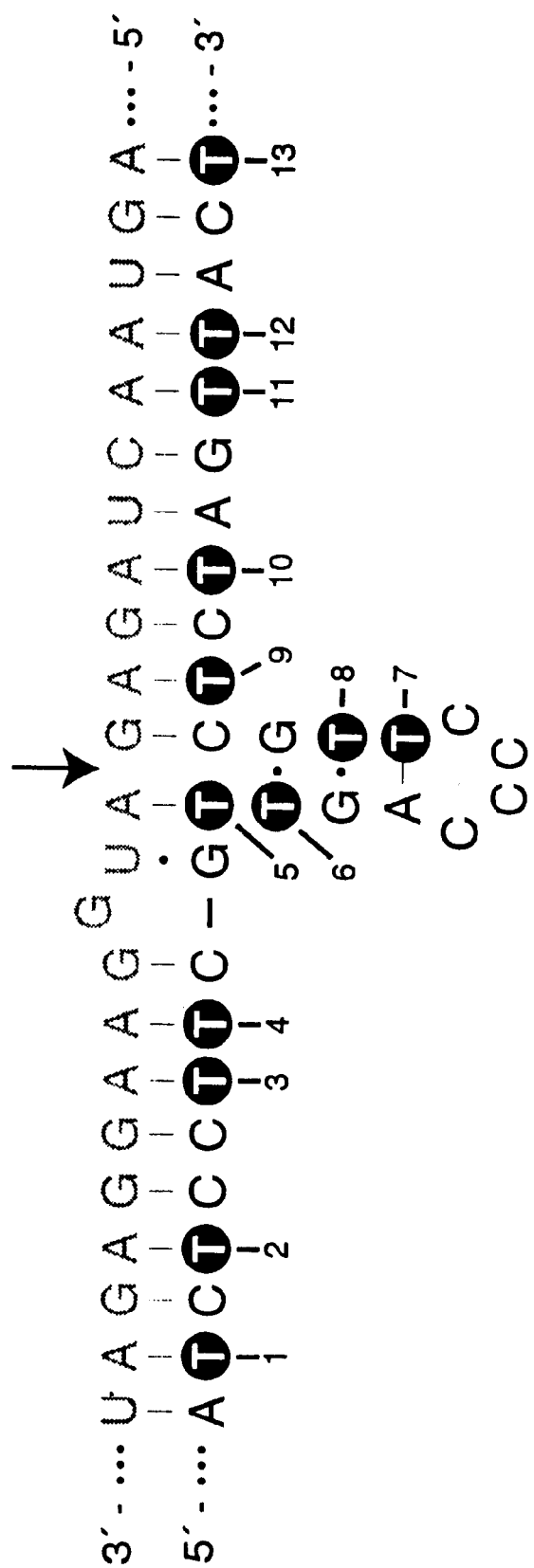
FIG. 11 shows the 16.2-11 enzyme with extended substrate-recognition domains. Highlighted Ts correspond to imidazole-containing, deoxyuridine residues. All imidazone-containing residues were found to be dispensable with the exception of numbers 5, 7 and 8 (SEQ ID NOS 56 and 57).

Deletion analyses were performed to define the minimal motif of the 16.2-11 catalyst and to test putative base-pairing interactions involving the DNA and RNA domains. A set of 3'-terminal deletion mutants was constructed by template-directed primer extension in the presence of dideoxy-CTP. These molecules was allowed to react in the presence of 10 μM $Zn^{2+}$ and the products were analyzed by PAGE. The catalytically non-essential nucleotides at the 3' end were determined by identifying the smallest 3'-truncated molecule that was still capable of catalyzing the rapid cleavage of the attached RNA substrate (FIG. 10). Similarly, the non-essential nucleotides at the 5' end were determined by the construction and analysis of a series of 5'-terminal deletion mutants. Taken together, these studies revealed that the ~20-nucleotide region of high sequence similarity alone was sufficient for robust catalytic activity in the intramolecular cleavage reaction. However, when the nucleotides within this region were prepared as a separate molecule and directed to cleave a separate RNA substrate, no cleavage was observed. The two putative substrate-recognition domains of the catalyst then were extended by 5 nucleotides in the 5' direction and 6 nucleotides in the 3' direction, and the resulting molecule was found to cleave the separate RNA substrate at a rate comparable to that of the intermolecular cleavage reaction (FIG. 11).

The 16.2-11 molecule with extended substrate-recognition domains contained 13 C5-imidazole-deoxyuridine residues. It seemed likely that many of these could be replaced by thymidine without reducing catalytic activity. Several different forms of the molecule were prepared by chemical synthesis, testing different combinations of either C5-imidazole-deoxyuridine or thymidine at the 13 positions. This analysis revealed that only three imidazole-containing residues were necessary for catalysis, all located close to the cleavage site (FIG. 11). Placing imidazole residues at any combination of two of these three positions resulted in no catalytic activity, while the molecule containing the three imidazole substitutions was as active as the fully-substituted molecule.

Substrate recognition by the imidazole-functionalized DNA enzyme appears to involve unusual base-pairing interactions on the 3' side of the substrate cleavage site. These include: 1) a Watson-Crick pair formed by an imidazole-deoxyurine of the enzyme and an adenine of the substrate located immediately downstream from the cleavage site; 2) a dG•rU "wobble" pair located at the next position downstream; 3) an unpaired guanidine of the substrate located one more position away (FIG. 11). In order to clarify the nature of these interactions, a series of variant enzymes and substrates were prepared by chemical synthesis and tested in the intermolecular cleavage reaction. This revealed that the dG•rU wobble pair could not be replaced by dG•rC, dA•rU, or dT•rU without a complete loss of catalytic activity. The unpaired rG could not be deleted or changed to rA, while the rG located at the next position downstream from the cleavage site could be changed to rA so long as the opposing nucleotide of the enzyme was changed to dT. All of the other putative base-pairing interactions between the enzyme and substrate were freely interchangeable so long as complementarity was maintained.

The 16.2-11 enzyme appears to form a three-helix junction involving the internal hairpin and the two substrate-recognition domains. The cleavage site is located at the junction, directly opposite the hairpin. The hairpin contains two wobble pairs and one Watson-Crick pair, closed by a loop of four deoxycytidine residues (FIG. 11). Changing the proximal wobble pair from dT•dG to dC•dG reduced activity, while changing it to dT•dA produced no significant change. Changing the dG•imidazole-dU pair to dA•imidazole-dU reduced activity slightly. Lengthening the stem by one base pair at the distal end reduced activity substantially. Changing the loop sequence from CCCC to GCAC, had no significant effect on activity. The latter sequence was found to occur in many of the selected clones (FIG. 9). However, changing the loop to the stable "triloop" sequence AAG abolished activity. In summary, the detailed composition of the internal hairpin has an important influence on the activity of the 16.2-11 enzyme.

Figure 12:
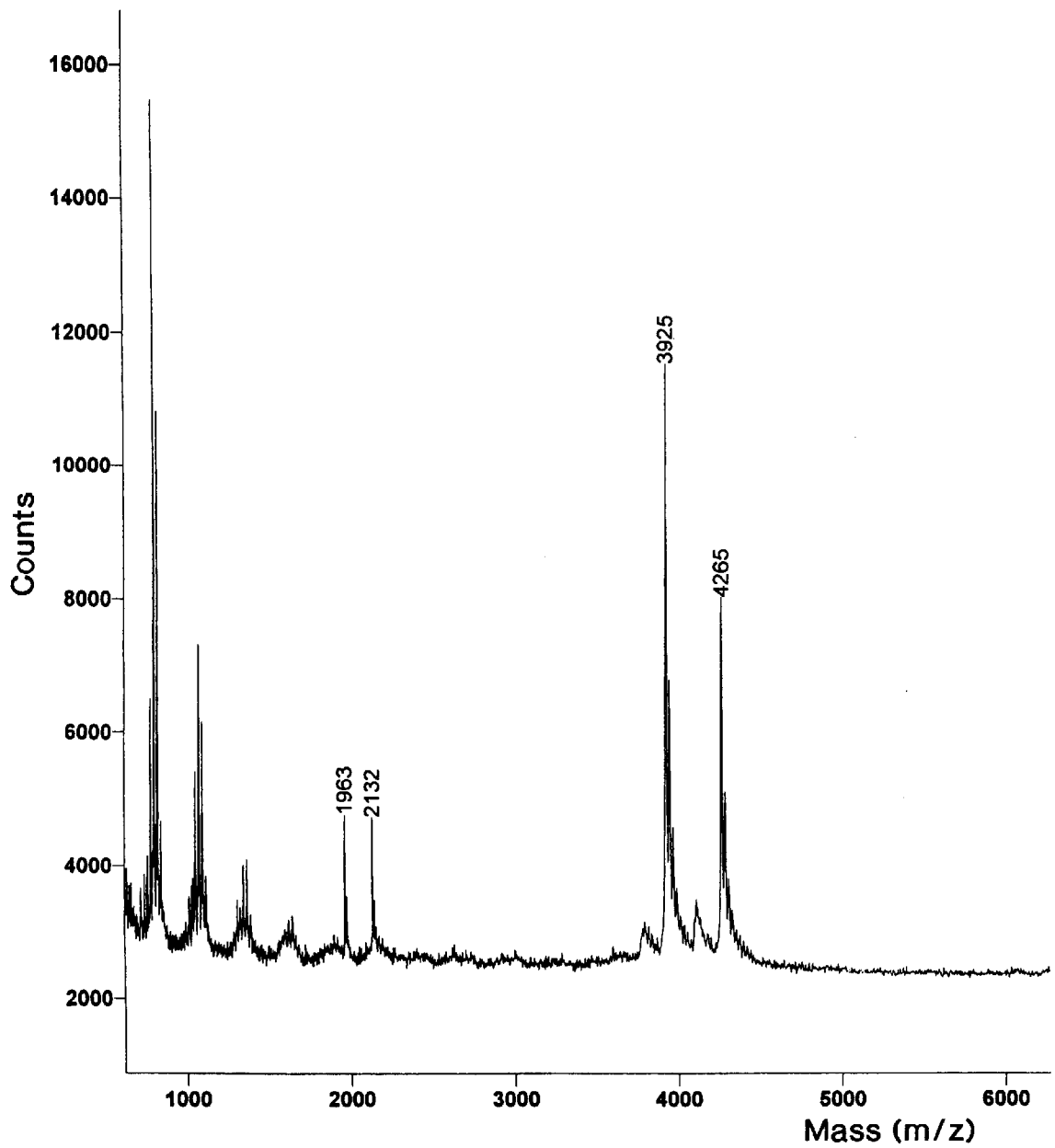
FIG. 12 shows MALDI mass spectrum of the products from a cleavage reaction catalyzed by the 16.2-11 imidazole-functionalized DNA enzyme.

Properties of the Imidazole-Functionalized DPNA Enzyme. The products of RNA cleavage by the 16.2-11 enzyme were analyzed by PAGE and MALDI mass spectrometry. The electrophoretic mobility of the 5<<cleavage product confirmed the presence of a terminal 2',3'-cyclic phosphate group, based on comparison to authentic material produced by partial alkaline hydrolysis of the substrate RNA. The mass of the 5' cleavage product corresponds to a molecule terminating in either a 2', 3', or 2',3'-cyclic phosphate and that of the 3' cleavage product corresponds to a molecule terminating in a 5' hydroxyl (FIG. 12).

The substrate generality of the imidazole-functionalized DNA enzyme was tested by employing an RNA substrate of entirely different sequence, with the exception of the unusually paired AUG sequence located immediately downstream from the cleavage site. The substrate-recognition domains of the enzyme were redesigned so that they were complementary to the new substrate and the catalytic activity of both this and the original form of the enzyme, each with their respective substrates, was compared (FIG. 12). The substrate-recognition domains were made sufficiently short that release of the cleaved products would not limit the rate of catalytic turnover. The enzymes were found to cleave their substrate with a nearly identical catalytic rate under multiple-turnover conditions. This suggests that the imidazole-functionalized DNA enzyme can be made to cleave a wide variety of RNA substrates, so long as the AUG sequence is present immediately downstream from the cleavage site.

The 16.2-11 enzyme, when directed to cleave either of the two RNA substrates, exhibits Michaelis-Menten saturation kinetics (FIG. 13). The values for $k_{cat}$ were 1.4 and 1.5 $min^{-1}$ and $K_m$ were 39 and 99 nM, for the original and altered substrate, respectively (measured in the presence of 10 $\mu$M $Zn^{2+}$, 1 mM $Mg^{2+}$, and 150 mM $Na^+$ at pH 7.5 and 37° C.). The catalytic rate enhancement is ~$10^7$-fold compared to the uncatalyzed reaction rate (Thompson, et al., Bioorg. Chem. 23: 471–481 (1995); Hertel, et al., PNAS USA 94: 8497–8502 (1997)).

Figure 14A:
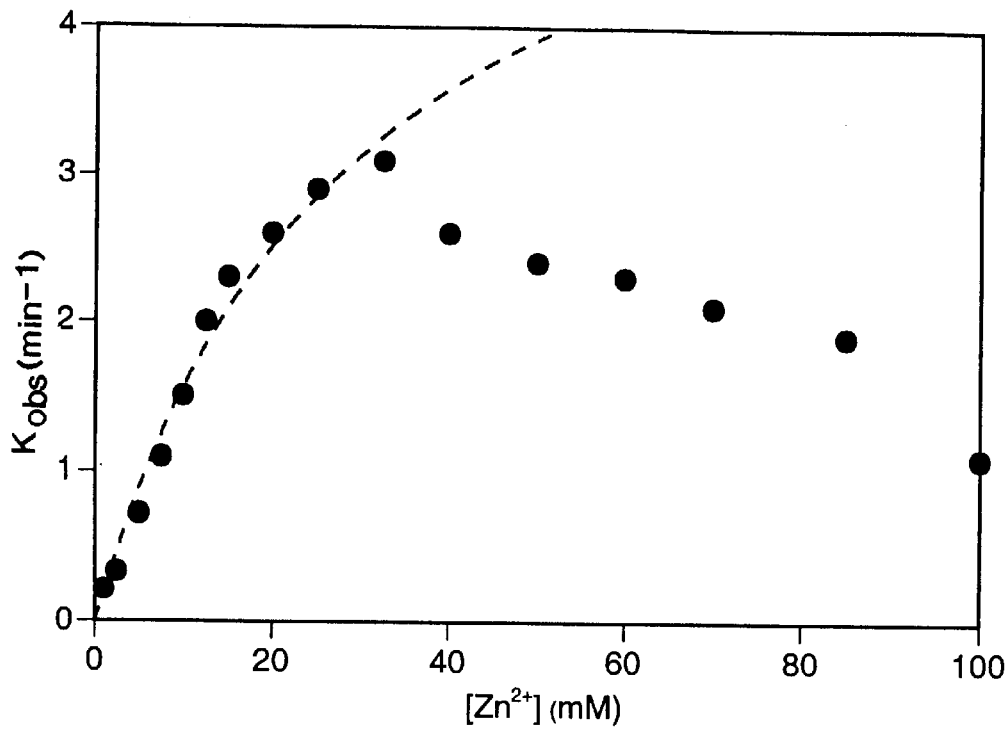
FIGS. 14A–14B show dependence of the rate of substrate cleavage on reaction conditions (a) $Zn^{2+}$ dependence of the reaction. Reactions were carried out in the presence of a variable concentration of $Zn^{2+}$, 1 mM $MgCl_2$, 150 mM NaCl, and 50 mM EPPS (pH 7.5) at 37° C. (b) pH dependence of the reaction. Reactions were carried out in the presence of 10 $\mu$M $ZnCl_2$, 1 mM $MgCl_2$, 150 mM NaCl, and a 50 mM concentration of either MES (triangles), PIPES (squares), or EPPS (circles) at 37° C.
Figure 14B:
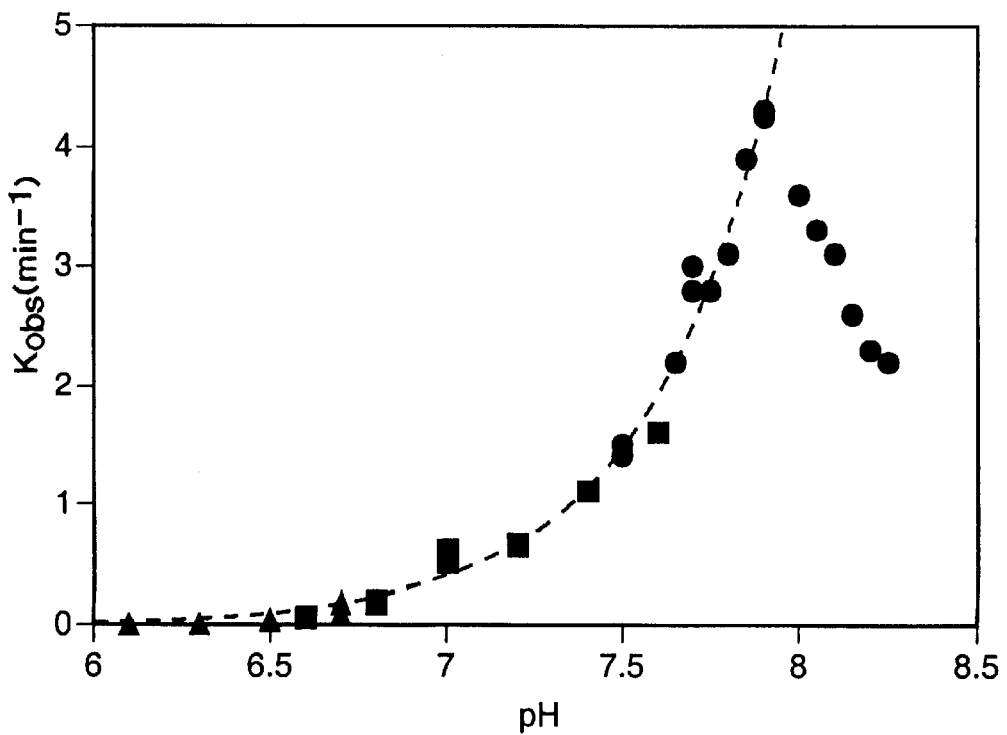

The catalytic rate was independent of the concentration of $Mg^{2+}$, or $Na^{2+}$, but was highly dependent on the concentration of $Zn^{2+}$ and on pH (FIG. 14). The catalytic rate increased with increasing $Zn^{2+}$ concentration, reaching a maximum of 3.1 $min^{-1}$ in the presence of 30 $\mu$M $Zn^{2+}$ at pH 7.5. Further increases in the concentration of $Zn^{2+}$ resulted in decreased catalytic activity, suggesting that $Zn^{2+}$ may be inhibitory when bound at one or more low affinity sites in the enzyme-substrate complex. The catalytic rate increased exponentially with increasing pH over the range of 5.9–7.9, reaching a maximum of 4.3 $min^{-1}$ at pH 7.9 in the presence of 10 $\mu$M $Zn^{2+}$ (FIG. 14b). Further increases in pH resulted in a steep drop in catalytic activity. These results indicate that the apparent $pK_a$ of a catalytically-essential group within the active site of the enzyme is $\geq$7.6. Because the pH-rate profile does not reach a level plateau before dropping off, the $pK_a$ cannot be determined accurately. The best-fit titration curve for the data up to pH 7.9 suggests that the $pK_a$ of the essential group is considerably greater than 7.6.

The 16.2-11 imidazole-functionalized DNA enzyme exhibits a unique set of functional properties. Like most nucleic acid enzymes, it recognizes its RNA substrate primarily through Watson-Crick base pairing. This makes it possible for the enzyme to cleave a variety of target RNAs through simple alteration of the substrate-recognition domains. Like many protein enzymes, the 16.2-11 DNA enzyme contains essential imidazole groups that are likely to be involved in catalysis. These imidazole substituents allow the enzyme to achieve a catalytic rate of >1 $min^{-1}$ in the presence of only micromolar concentrations of a divalent metal cation. Despite its small size of only ~28 nucleotides, the enzyme exhibits a catalytic rate enhancement of ~$10^7$-fold compared to the uncatalyzed reaction.

Figure 15A:
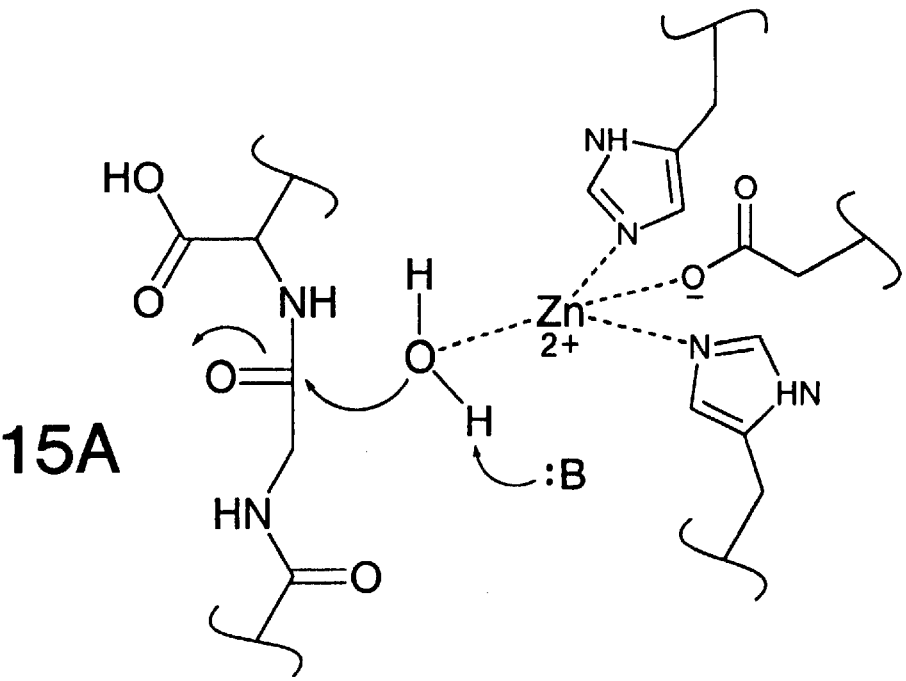
FIGS. 15A–15B show a comparison of the chemical mechanism for catalysis by (a) carboxypeptidase A with (b) a hypothetical mechanism for catalysis by the 16.2-11 imidazone-functionalized DNA enzyme.
Figure 15B:
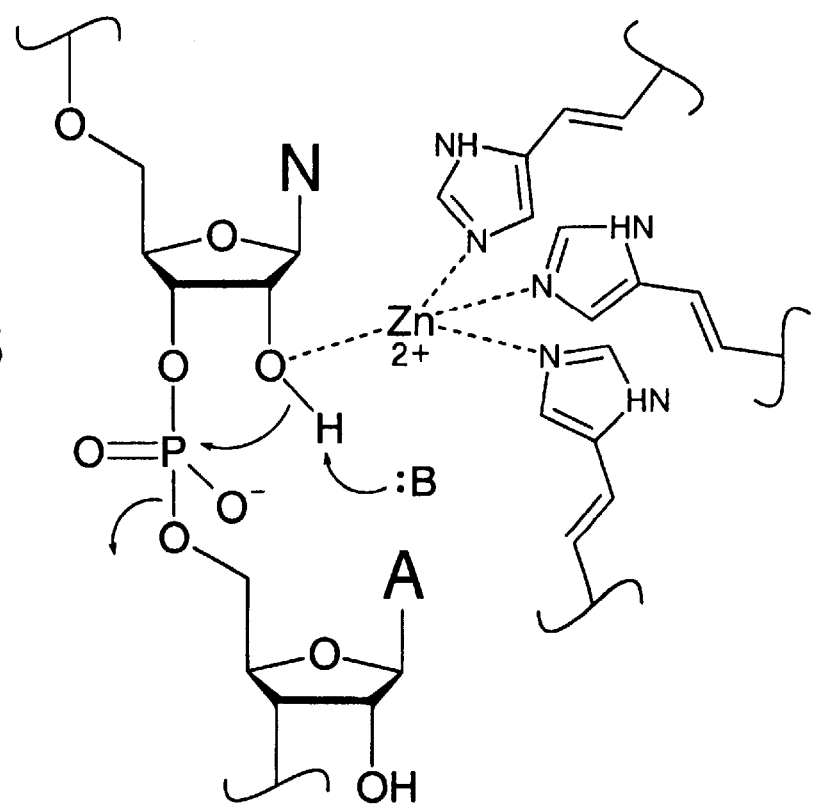

The chemical transformation catalyzed by the imidazole-functionalized DNA enzyme is identical to that catalyzed by many small nucleic acid enzymes and ribonuclease proteins. However, the detailed mechanism of the DNA-catalyzed reaction appears to be unique among known endoribonucleases. The dependence of the reaction on $Zn^{2+}$ concentration and pH suggests that the enzyme utilizes a tightly-bound $Zn^{2+}$ ion to activate the 2' hydroxyl group at the cleavage site for an attack on the adjacent phosphorus, resulting in RNA cleavage. These observations, together with the requirement for three imidazole-containing nucleotide analogues, suggest that one or more of the imidazole groups are involved in binding the $Zn^{2+}$ ion that participates in catalysis. In this way, the mechanism of the imidazole-functionalized DNA enzyme may be similar to that of certain $Zn^{2+}$-dependent protein enzymes such as carboxypeptidase A. These protein enzymes utilize imidazole and carboxylate side chains to bind and position a $Zn^{2+}$ ion that coordinates and activates a $H_2O$ molecule for nucleophilic attack (FIG. 22a; for review, see Lipscomb, et al., Chem. Rev. 96: 2375–2433 (1996)). A hypothetical mechanism for RNA cleavage by the 16.2-11 enzyme is shown in FIG. 15b. According to this mechanism, the $Zn^{2+}$ ion is coordinated by three imidazole groups of the enzyme, which would allow tight binding and precise positioning of the metal. The bound $Zn^{2+}$ could then coordinate to and activate the 2' hydroxyl group at the cleavage site for nucleophilic attack on the adjacent phosphorus atom (FIG. 15b).

It is possible that the three imidazole groups and the $Zn^{2+}$ ion(s) that are required for catalysis play a purely structural role. It is also possible that one or more imidazole groups play a direct role in catalysis, for example, by acting as a general base to help deprotonate the 2' hydroxyl at the cleavage site. The apparent $pK_a$ of a catalytically-essential group within the enzyme-substrate complex is $\geq 7.6$, which is considerably higher than would be expected for urocanic acid ($pK_a$=6.1; Zimmerman, et al., J. Am. Chem. Soc. 110: 5906–5908 (1998) or histidine ($pK_a$=: 6.4; Fersht, Enzyme Structure and Mechanism (1985)). There is precedent for substantial $pK_a$ shifts of functional groups within both proteins (Fersht, Enzyme Structure and Mechanism (1985) and structured RNAs (Connell, et al., Science 264: 1137–1141 (1994); Legault, et al., J. Am. Chem. Soc. 119: 6621–6628 (1997)). However, there is no evidence to support (or refute) the possibility that such a shift occurs within the 16.2-11 enzyme. Furthermore, the value of 7.6 is a lower limit for the apparent $pK_a$ of the catalytically-essential titratable group. Rather than invoke a dramatic upward shift in the $pK_a$ of an imidazole nitrogen, the pH-rate profile of the enzyme can be viewed as consistent with the titration of a $Zn^{2+}$-coordinated ribose 2'-hydroxyl (FIG. 15b) or $Zn^{2+}$-coordinated water that acts as a general base.

The catalytic rate enhancement of the 16.2-11 DNA enzyme compares favorably to that of nucleic acid enzymes of similar size. However, the enzyme's rate enhancement is 4–5 orders of magnitude lower than that of RNase A. This difference may be explained in part by the advantage of protein enzymes in achieving a higher density of functional groups near the active site (Narlikar, et al., Annu. Rev. Biochem. 66: 19–59 (1997)). This is due to the more flexible backbones and approximately four-fold smaller residues of proteins compared to nucleic acids. There are several catalytic residues at the active site of RNase A, including two histidines, a lysine, and an aspartate, that must function in concert to perform the cleavage reaction (Raines, Chem. Rev. 98: 1045–1065 (1998)). Nucleic acid enzymes, even those endowed with enhanced functionality, may not be able to equal protein enzymes in regard to functional group density.

The difference in rate enhancement between RNase A and the 16.2-11 enzyme may also be explained in part by the advantage of protein enzymes in forming a "rigid" active site (Narlikar, et al., Annu. Rev. Biochem. 66: 19–59 (1997)). Rigidity is important because it allows catalytic groups to be positioned with high effective concentration to stabilize the transition state of a reaction. A greater number of subunits may allow an enzyme to achieve a higher level of rigidity and catalytic rate. For example, the rate of RNA cleavage catalyzed by the 34-nucleotide hammerhead ribozyme is about 2 orders of magnitude slower than that of the 85-nucleotide HDV ribozyme (Tanner, et al., Curr. Biol. 4: 488–498 (1994)). Because protein enzymes have a greater diversity of functional groups and can explore more conformational alternatives compared to nucleic acid enzymes, they can achieve the same level of structural rigidity with fewer subunits. The DNA enzyme, not only has far fewer subunits than RNase A, but those subunits are more unwieldy in achieving structural rigidity.

Functional group density and structural rigidity may also be important factors in the DNA enzyme's affinity for the divalent metal cofactor. Although this affinity is much tighter than has been observed for other nucleic acid catalysts, it is weaker than that observed for some $Zn^{2+}$ peptidase proteins. These protein enzymes may be able to form relatively rigid pockets containing multiple ligands that are precisely positioned to coordinate the $Zn^{2+}$ ion (Lipscomb, et al., Chem. Rev. 96: 2375–2433 (1996)).

Although the catalytic rate and $Zn^{2+}$-binding affinity of the 16.2-11 enzyme are inferior to those of RNase A and carboxypeptidase A, respectively, they were more than adequate to meet the functional challenge imposed by the in vitro selection constraints. During the first seven rounds of selection, the enzyme was given one hour to complete the reaction in the presence of 10 $\mu M$ $Zn^{2+}$. Under these conditions, there was no pressure favoring the selection of a larger or faster enzyme. In addition, because small catalysts such as the 16.2-11 enzyme were present in higher copy number in the initial pool compared to larger motifs, the small catalysts had an intitial advantage. It is possible that an imidazole-functionalized DNA enzyme with a size and catalytic properties closer to those of RNase A and carboxypeptidase A could have been obtained if more stringent conditions were applied during the early rounds of in vitro selection.

The development of the 16.2-11 DNA enzyme demonstrates how the mechanistic properties of DNA and protein enzymes can be combined in a single molecule. This was accomplished using a nucleotide analogue containing a versatile catalytic group that often plays an important role in protein-based catalysis. Future studies may lead to the development of modified DNA enzymes that contain functional groups not found in proteins. The use of more than one nucleotide analogue may allow the development of catalysts enhanced with even greater functional diversity.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A catalytic DNA molecule that specifically cleaves a substrate nucleic acid at a defined cleavage site, said catalytic DNA molecule comprising at least one pyrimidine nucleotide of the structure below

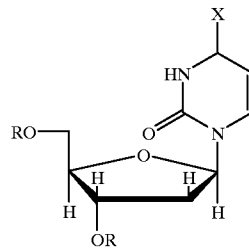

where X is $NH_2$ or O, C:C is a carbon-carbon double bond or a carbon-carbon triple bond, each R is independently a cation or

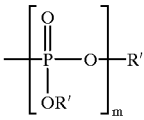

wherein each R' is absent or a cation and m is 1, 2 or 3, and $R_1$ is

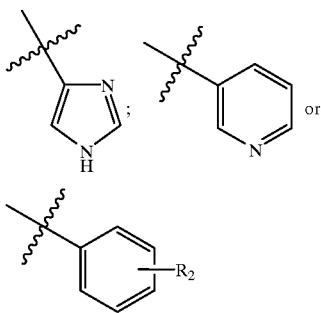

wherein $R_2$ is

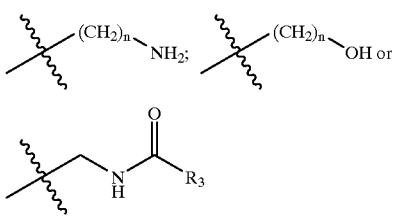

wherein $R_3$ is $(CH_2)_n COOH$ or

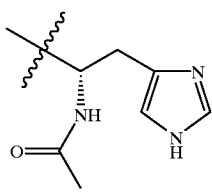

and n is an integer from 0 to 6.

2. The DNA molecule of claim 1 wherein n is 0, 1 or 2.

3. The DNA molecule of claim 1 wherein at least one R is a cation.

4. The DNA molecule of claim 3 wherein the cation is hydrogen or an alkali metal.

5. The DNA molecule of claim 4 wherein the alkali metal is sodium or potassium.

6. The DNA molecule of claim 1 where X is O and C:C is a carbon-carbon double bond.

7. The DNA molecule of claim 6 wherein R1 is

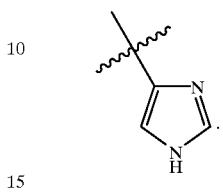

8. The catalytic DNA molecule of claim 1, wherein said defined cleavage site comprises a single-stranded nucleic acid.

9. The catalytic DNA molecule of claim 1, wherein said substrate comprises RNA, DNA, modified RNA, modified DNA, nucleotide analogs, or composites thereof.

10. The catalytic DNA molecule of claim 1, that catalyzes hydrolytic cleavage of a phosphoester bond at said cleavage site.

11. The catalytic DNA molecule of claim 1 that is single-stranded.

12. The catalytic DNA molecule of claim 1, wherein said substrate nucleic acid is attached to said catalytic DNA molecule.

13. The catalytic DNA molecule of claim 1, wherein said catalytic DNA molecule includes a conserved nucleotide core comprising one or more conserved nucleotide sequences.

14. The DNA molecule of claim 1 that comprises the nucleotide sequence 5'-GN(N/T)GRSCHCNNR-3' (SEQ ID NO 8) where N is imidazole-deoxyuridylate, R is A or G, S is C or G and H is A, C or T.

15. The DNA molecule of claim 14 wherein R is A.

16. The DNA molecule of claim 14 wherein S is G.

17. The DNA molecule of claim 14 wherein H is C.

18. The DNA molecule of claim 14 wherein S and H are both C.

* * * * *

UNITED STATES PATENT AND TRADEMARK OFFICE
CERTIFICATE OF CORRECTION

PATENT NO : 6,110,462
DATED : August 29, 2000
INVENTOR(S) : Barbas, et al.

It is certified that error appears in the above-identified patent and that said Letters Patent are hereby corrected as shown below:

In Column 1, line 4, please insert:

--This invention was made with government support under Contract Nos. CA27489 by the National Institutes of Health. The government has certain rights in the invention.--

Signed and Sealed this

Fifteenth Day of May, 2001

*Attest:*

NICHOLAS P. GODICI

*Attesting Officer*     *Acting Director of the United States Patent and Trademark Office*

SEQUENCE LISTING

<160> NUMBER OF SEQ ID NOS: 58

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:
      termination sequence

<400> SEQUENCE: 1
cggtaagctt ggcac                                                          15

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      termination sequence
<220> FEATURE:
<221> NAME/KEY: modified_base
<222> LOCATION: (8)
<223> OTHER INFORMATION: adenosine ribonucleotide

<400> SEQUENCE: 2
tcactatagg aagagatgg                                                      19

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:  DNA enzyme

<400> SEQUENCE: 3
acacatctct gaagtagcgc cgccgtatag tgacgcta                                 38

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:  oligomer
<220> FEATURE:
<221> NAME/KEY: misc_feature
<222> LOCATION: (16)
<223> OTHER INFORMATION: n = g, a, c or t

<400> SEQUENCE: 4
gtgccaagct taccgngtcg ccatctcttc c                                        31

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:  oligomer
<220> FEATURE:
<221> NAME/KEY: modified_base
<222> LOCATION: (28)
<223> OTHER INFORMATION: adenosine ribonucleotide

<400> SEQUENCE: 5
gggacgaatt ctaatacgac tcactata                                            28

```
<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (28)
<223> OTHER INFORMATION: adenosine ribonucleotide

<400> SEQUENCE: 6
gggacgaatt ctaatacgac tcactata                                          28

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (8)
<223> OTHER INFORMATION: adenosine ribonucleotide

<400> SEQUENCE: 7
tcactatagg aagagatgg                                                    19

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: substrate
<220> FEATURE:
<221> NAME/KEY: misc_feature
<222> LOCATION: (1)..(13)
<223> OTHER INFORMATION: N=imidazole-deoxyuridine

<400> SEQUENCE: 8
gnntgrschc nnr                                                          13

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: template

<400> SEQUENCE: 9
ccatctcttc ctatagtgag tccggctgca                                        30

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 10
gtgccaagct taccg                                                        15

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: primer
```

-continued

```
<400> SEQUENCE: 11
ctgcagaatt ctaatacgac tcactatagg aagagatggc gac                    43

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:  substrate
<220> FEATURE:
<221> NAME/KEY: modified_base
<222> LOCATION: (8)
<223> OTHER INFORMATION: adenosine ribonucleotide

<400> SEQUENCE: 12
tcactatagg aagagatgg                                               19

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence:  substrate
<220> FEATURE:
<221> NAME/KEY: modified_base
<222> LOCATION: (28)
<223> OTHER INFORMATION: adenosine ribonucleotide

<400> SEQUENCE: 13
gggacgaatt ctaatacgac tcactatagg aagagatggc gac                    43

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence:  DNA enzyme

<400> SEQUENCE: 14
tcacacatct ctgaagtagc gccgccgtat gtgacgctag gggttcgcct             50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence:  DNA enzyme

<400> SEQUENCE: 15 gggggggaacg ccgtaacaag ctctgaacta gcggttgcga tatagtcgta            50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence:  DNA enzyme

<400> SEQUENCE: 16
cgggactccg tagcccattg cttttttgcag cgtcaacgaa tagcgtatta            50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence:  DNA enzyme
```

<400> SEQUENCE: 17
ccaccatgtc ttctcgagcc gaaccgatag ttacgtcata cctcccgtat        50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 18
gccagattgc tgctaccagc ggtacgaaat agtgaagtgt tcgtgactat        50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 19
ataggccatg ctttggctag cggcaccgta tagtgtacct gcccttatcg        50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 20
tctgctctcc tctattctag cagtgcagcg aaatatgtcg aatagtcggt        50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 21
ttgcccagca tagtcggcag acgtggtgtt agcgacacga taggcccggt        50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 22
ttgctagctc ggctgaactt ctgtagcgca accgaaatag tgaggcttga        50

<210> SEQ ID NO 23
<211> LENGTH: 68
<212> TYPE: DNA
<213> ORGANISM: Artificial Sequence
<220> FEATURE:
<223> OTHER INFORMATION: Description of Artificial Sequence: oligomer
<220> FEATURE:
<221> NAME/KEY: misc_feature
<222> LOCATION: (49)
<223> OTHER INFORMATION: n = g, a, c or t

<400> SEQUENCE: 23

-continued

```
gggacgaatt ctaatacgac tcactatagg aagagatggc gacatctcng tgacggtaag      60
cttggcac                                                              68

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence:   DNA enzyme

<400> SEQUENCE: 24
ccgcccacct cttttacgag cctgtacgaa atagtgctct tgttagtat                 49

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence:   DNA enzyme

<400> SEQUENCE: 25
tctcttcagc gatgcacgct tgttttaatg ttgcacccat gttagtga                  48

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence:   DNA enzyme

<400> SEQUENCE: 26
tctcatcagc gattgaacca cttggtggac agacccatgt tagtga                    46

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence:   DNA enzyme

<400> SEQUENCE: 27
ccgcccacct cttttacgag cctgtacgaa atagtgttct tgttagtat                 49

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence:   DNA enzyme

<400> SEQUENCE: 28
ccgcccacct cttttacgag cctgtacgaa atagtgctct cgttagtat                 49

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence:   DNA enzyme

<400> SEQUENCE: 29
tctcagactt agtccatcac actctgtgca tatgcctgct tgatgtga                  48

<210> SEQ ID NO 30
<211> LENGTH: 42
```

-continued

```
<212> TYPE: DNA
<213> ORGANISM: Artificial Sequence
<220> FEATURE:
<223> OTHER INFORMATION: Description of Artificial Sequence: DNA enzyme

<400> SEQUENCE: 30
ctctcatctg ctagcacgct cgaatagtgt cagtcgatgt ga                          42

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: DNA enzyme

<400> SEQUENCE: 31
tacagcgatt caccettgtt taagggttac acccatgtta                             40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: DNA enzyme

<400> SEQUENCE: 32
atcagcgatt aacgcttgtt tcaatgttac acccatgtta                             40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: DNA enzyme

<400> SEQUENCE: 33
ttcagcgatt aacgcttatt ttagcgttac acccatgtta                             40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: DNA enzyme

<400> SEQUENCE: 34
atcagcgatt caccettgtt ttaaggttgc acccatgtta                             40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: DNA enzyme

<400> SEQUENCE: 35
atcagcgatt caccettgtt taagcgttac acccatgttg                             40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: DNA enzyme

<400> SEQUENCE: 36
```
atcagcgatt cacccttgtt ttaaggttac acccatgtta                                      40

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence:  DNA enzyme

<400> SEQUENCE: 37
atcagcgatt aacgcttatt ttagcgttac acccatgtta                                      40

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence:  DNA enzyme

<400> SEQUENCE: 38
atcagcgatt aacgcttgtt ttagtgttgc acccatgtta                                      40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence:  DNA enzyme

<400> SEQUENCE: 39
atcagcgatt aacgcttatt ttagcattac acccatgtta                                      40

<210> SEQ ID NO 40
<211> LENGTH: 73
<212> TYPE: DNA
<213> ORGANISM: Artificial Sequence
<220> FEATURE:
<223> OTHER INFORMATION: Description of Artificial Sequence:  template

<400> SEQUENCE: 40
gctaaaaaag ctgctaaaaa gctgctaaaa gctgctaaag ctaagctagc tccctttagt               60
gagggttaat tgc                                                                   73

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence:  primer

<400> SEQUENCE: 41
gcaattaacc ctcactaaag gg                                                         22

<210> SEQ ID NO 42
<211> LENGTH: 34
<212> TYPE: DNA
<213> ORGANISM: Artificial Sequence
<220> FEATURE:
<223> OTHER INFORMATION: Description of Combined DNA/RNA Molecule:
      template
<220> FEATURE:
<223> OTHER INFORMATION: Description of Artificial Sequence:  template

<400> SEQUENCE: 42
ggaaaaagua acuagagaug gaagagatgg cgac                                            34

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: template
<220> FEATURE:
<221> NAME/KEY: misc_feature
<222> LOCATION: (16)
<223> OTHER INFORMATION: n = g, a, c or t

<400> SEQUENCE: 43
gtgccaagct taccgngtcg ccatctcttc c                          31

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 44
ggaagagatg gcgac                                            15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 45
gtgccaagct taccg                                            15

<210> SEQ ID NO 46
<211> LENGTH: 34
<212> TYPE: RNA
<213> ORGANISM: Artificial Sequence
<220> FEATURE:
<223> OTHER INFORMATION: Description of Artificial Sequence: primer

<400> SEQUENCE: 46
ggaaaaagua acuagagaug gaagagaugg cgac                       34

<210> SEQ ID NO 47
<211> LENGTH: 12
<212> TYPE: RNA
<213> ORGANISM: Artificial Sequence
<220> FEATURE:
<223> OTHER INFORMATION: Description of Artificial Sequence: DNA enzyme
<220> FEATURE:
<221> NAME/KEY: misc_feature
<222> LOCATION: (1)..(12)
<223> OTHER INFORMATION: U at positions 2, 6 and 12 =
      C5-imidazole-deoxyuridine

<400> SEQUENCE: 47
guaacuagag au                                               12

<210> SEQ ID NO 48
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 48

-continued

```
cccgaggcac caatccttcg ttgagctctt actcggtgaa acggccgcta          50
```

<210> SEQ ID NO 49
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 49

```
cccagaaggc cgaaaccgct tcgttgaccc cttgctctag ggttactagg          50
```

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 50

```
gacagcaata tcttcgttga ccccttgctc tatatagcct tcaggccccc          50
```

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 51

```
cacacgggac gcatcggact tcgttgagca cttactctag ccgcgcccat          50
```

<210> SEQ ID NO 52
<211> LENGTH: 50
<212> TYPE: DNA
<213> ORGANISM: Artificial Sequence
<220> FEATURE:
<223> OTHER INFORMATION: Description of Artificial Sequence: DNA enzyme

<400> SEQUENCE: 52

```
ccacaccgta caccagctcg aggttgggca cctactctaa caccagcggt          50
```

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: DNA enzyme

<400> SEQUENCE: 53

```
gggacaaatt ggccattagc cgccttcgtt gagcacgcta cactaggccc a        51
```

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: DNA enzyme
<220> FEATURE:
<221> NAME/KEY: misc_feature
<222> LOCATION: (12)
<223> OTHER INFORMATION: n = g, a, c or t

<400> SEQUENCE: 54

```
cttcgttgag cncttactct a                                         21
```

-continued

```
<210> SEQ ID NO 55
<211> LENGTH: 84
<212> TYPE: DNA
<213> ORGANISM: Artificial Sequence
<220> FEATURE:
<223> OTHER INFORMATION: Description of Combined DNA/RNA Molecule:  DNA
      enzyme
<220> FEATURE:
<223> OTHER INFORMATION: Description of Artificial Sequence:  DNA enzyme
<220> FEATURE:
<221> NAME/KEY: misc_feature
<222> LOCATION: (54)..(81)
<223> OTHER INFORMATION: T=imidazole-deoxyuridine

<400> SEQUENCE: 55
ggaaaaagua acuagagaug gaagagaugg cgaccccaga aggccgaaac cgcttcgttg    60
accccttgct ctagggttac tagg                                          84

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence:  substrate

<400> SEQUENCE: 56
aguaacuaga gauggaagga gau                                           23

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence:  DNA enzyme
<220> FEATURE:
<221> NAME/KEY: misc_feature
<222> LOCATION: (1)..(32)
<223> OTHER INFORMATION: T=imidazole-deoxyuridine

<400> SEQUENCE: 57
atctccttcg ttgaccccctt gctctagtta ct                                32

<210> SEQ ID NO 58
<211> LENGTH: 18
<212> TYPE: RNA
<213> ORGANISM: Artificial Sequence

<400> SEQUENCE: 58
aguaccgaau gacgcagc                                                 18
```